(12) United States Patent
Shao et al.

(10) Patent No.: US 10,239,863 B2
(45) Date of Patent: Mar. 26, 2019

(54) FACTOR XIA INHIBITORS

(71) Applicant: Merck Sharp & Dohme Corp., Rahway, NJ (US)

(72) Inventors: Ning Shao, Watchung, NJ (US); Scott D. Edmondson, Clark, NJ (US); Santhosh Neelamkavil, Edison, NJ (US); Zhuyan Guo, Scotch Plains, NJ (US); Eric Mertz, Somerset, NJ (US); Yi Zang, Princeton Junction, NJ (US); Jiafang He, Dayton, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/789,088

(22) Filed: Oct. 20, 2017

(65) Prior Publication Data

US 2018/0179180 A1    Jun. 28, 2018

Related U.S. Application Data

(63) Continuation of application No. 15/027,086, filed as application No. PCT/US2014/059213 on Oct. 6, 2014, now abandoned.

(60) Provisional application No. 61/887,699, filed on Oct. 7, 2013.

(51) Int. Cl.
| | |
|---|---|
| *C07D 401/14* | (2006.01) |
| *C07D 401/10* | (2006.01) |
| *C07C 269/06* | (2006.01) |
| *C07D 413/14* | (2006.01) |
| *C07D 401/04* | (2006.01) |

(52) U.S. Cl.
CPC .......... *C07D 401/14* (2013.01); *C07C 269/06* (2013.01); *C07D 401/04* (2013.01); *C07D 401/10* (2013.01); *C07D 413/14* (2013.01)

(58) Field of Classification Search
CPC .................................................. C07D 401/14
USPC ....................................................... 514/234.2
See application file for complete search history.

(56) References Cited

U.S. PATENT DOCUMENTS

| | | |
|---|---|---|
| 2006/0211720 A1 | 9/2006 | Glunz et al. |
| 2009/0181983 A1 | 7/2009 | Corte |
| 2011/0021492 A1 | 1/2011 | Corte et al. |
| 2011/0028446 A1 | 2/2011 | Pinto et al. |
| 2011/0059958 A1 | 3/2011 | Nishida et al. |
| 2011/0135650 A1 | 6/2011 | Chackalamannil et al. |
| 2012/0041190 A1 | 2/2012 | Corte et al. |

FOREIGN PATENT DOCUMENTS

| | | |
|---|---|---|
| JP | 2005298628 | 10/2005 |
| WO | 2005014533 A2 | 5/2005 |
| WO | 2007070826 A1 | 6/2007 |
| WO | 2008157162 A1 | 12/2008 |
| WO | 2013056034 A1 | 4/2013 |
| WO | WO2013055984 A1 | 4/2013 |
| WO | WO2015047973 A1 | 4/2015 |

OTHER PUBLICATIONS

Extended European Search Report for 14851664.4, dated Feb. 20, 2017, 8 pages.
International Search Report for PCT/US14/59213 dated Jan. 7, 2015, 9 pages.

*Primary Examiner* — Taofiq A Solola
(74) *Attorney, Agent, or Firm* — Nicole M. Beeler; John C. Todaro

(57) ABSTRACT

The present invention provides a compound of Formula (I)

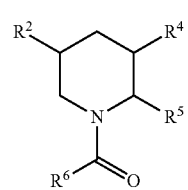

and pharmaceutical compositions comprising one or more said compounds, and methods for using said compounds for treating or preventing thromboses, embolisms, hypercoagulability or fibrotic changes. The compounds are selective Factor XIa inhibitors or dual inhibitors of Factor XIa and plasma kallikrein.

19 Claims, No Drawings

FACTOR XIA INHIBITORS

CROSS REFERENCE TO RELATED APPLICATIONS

This application is a continuation of U.S. application Ser. No. 15/027,086 filed on Apr. 4, 2016, which is a U.S. National Phase application under 35 U.S.C. § 371 of PCT Application No. PCT/US2014/059213 filed Oct. 6, 2014, which claims priority from U.S. Provisional Application Ser. No. 61/887,699, filed Oct. 7, 2013.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting Factor X is activated. The activated Factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting Factors V, VIII, IX, X, XI and XII and also prekallikrein, high molecular weight kininogen, calcium ions and phospholipids from platelets. The activation of Factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of Factor XII leads to a conformational change in the Factor XII molecule, thereby facilitating activation to proteolytic active Factor XII molecules (Factor XIIa and Factor XIIf). Factor XIIa (or XIIf) has a number of target proteins, including plasma prekallikrein and Factor XI. Active plasma kallikrein further activates Factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact ActivationPathway", Hemostasis and Thrombosis, pp. 103-122, Lippincott Williams & Wilkins (2001); Schmaier, A. H., "Contact Activation", Thrombosis and Hemorrhage, pp. 105-128 (1998)). The biological relevance of the contact activation system for thromboembolic 5 diseases is supported by the phenotype of Factor XII deficient mice. More specifically, Factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)). The fact that Factor XI is downstream from Factor XIIa, combined with the identical phenotype of the XII and XI deficient mice suggest that the contact activation system could play a major role in Factor XI activation in vivo. Plasma kallikrein is a zymogen of a trypsin-like serine protease and is present in plasma. The gene structure is similar to that of Factor XI. Overall, the amino acid sequence of plasma kallikrein has 58% homology to Factor XI. Proteolytic activation by Factor XIIa at an internal I 389-R390 bond yields a heavy chain (371 amino acids) and a light chain (248 amino acids). The active site of plasma kallikrein is contained in the light chain. The light chain of plasma kallikrein reacts with protease 15 inhibitors, including alpha 2 macroglobulin and Cl-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", Hemostasis and Thrombosis, pp. 103-122, Lippincott Williams & Wilkins (2001); Schmaier A. H., "Contact Activation", Thrombosis and Hemorrhage, pp. 105-128 (1998)).

Factor XIa inhibitor compounds are described in WO2013022814, WO 2013022814, WO 2013022818, WO 2013055984, WO2013056034, WO2013056060, WO2013118805. WO2013093484, WO2002042273, WO2002037937, WO2002060894, WO2003015715, WO2004002405, US20040180855, WO2004080971, WO2004094372, US20050228000, US20050282805, WO2005123680, US20090036438, US20120088758, US20060074103, WO2006062972, WO2006076246, US20060154915, US20090062287, US20060183771, WO2007070818, WO2007070816, WO2007070826, WO2008076805, WO2008157162, WO2009114677, WO2011100402, and WO2011100401.

SUMMARY OF THE INVENTION

The present invention relates to compounds of Formula I:

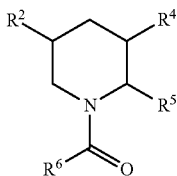

or pharmaceutically acceptable salts thereof. The compounds of Formula I are selective Factor XIa inhibitors or dual inhibitors of Factor XIa and plasma kallikrein, and as such may be useful in the treatment, inhibition or amelioration of one or more disease states that could benefit from inhibition of Factor XIa or plasma kallikrein, including thromboses, embolisms, hypercoagulability or fibrotic changes. The compounds of this invention could further be used in combination with other therapeutically effective agents, including but not limited to, other drugs useful for the treatment of thromboses, embolisms, hypercoagulability or fibrotic changes. The invention furthermore relates to processes for preparing compounds of Formula I, and pharmaceutical compositions which comprise compounds of Formula I and pharmaceutically acceptable salts thereof.

DETAILED DESCRIPTION OF THE INVENTION

The invention includes compounds of formula I

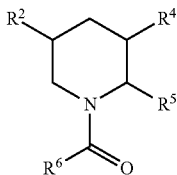

or a pharmaceutically acceptable salt thereof, wherein
$R^2$ is
1) aryl
2) $R^{21}$,
3) 4-7-membered saturated carbocycle,
4) —$OR^{21}$, or

5)

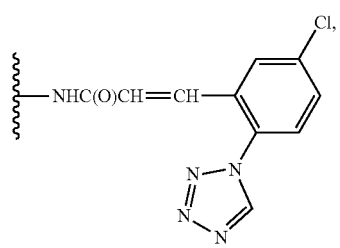

wherein $R^{21}$ is 4-7-membered unsaturated or saturated heterocycle containing one or two heteroatoms independently selected from N, O and S, wherein aryl is unsubstituted or monosubstituted with $CF_3$, and heterocycle is unsubstituted or monosubstituted with $NH_2$, $SO_2CH_3$ or $COCH_3$;
$R^6$ is
1) —CH=CH—$R^{63}$,
2) —$CH_2CH_2$—$R^{63}$,
3) 4-7 membered monocyclic saturated heterocycle having one or two heteroatoms independently selected from N, O and S,
4) $R^{62}$,
5) 7-9-membered bicyclic unsaturated carbocycle,
wherein wherein $R^{63}$ is aryl which is mono, di or trisubstituted with a substituent independently selected from halogen, $CF_3$ and tetrazole, saturated heterocycle is unsubstituted or substituted at the nitrogen atom with —C(NH)$NH_2$, and $R^{62}$ is unsaturated or saturated carbocycle unsubstituted or independently substituted with one or two of —$CH_2NH_2$, $NH_2$, $C(CH_3)_2NH_2$, $C_{1-6}$ alkyl, or $C_{3-8}$ cycloalkyl, or

6)

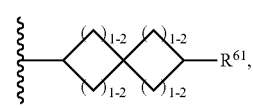

wherein $R^{61}$ is —$(CH_2)_{0-1}NH_2$;
$R^4$ is
1) —$CH_2OR^{41}$, wherein $R^{41}$ is hydrogen or —$Si(C_{1-6}$ alkyl)($C_{1-6}$ alkyl)($C_{1-6}$ alkyl),
2) aryl,
3) 3-7-membered monocyclic saturated carbocycle,
4) $C_{1-6}$ alkyl, or
5) —O—$R^{42}$, wherein $R^{42}$ is a 4-7-membered monocyclic saturated heterocycle having one or two heteroatoms independently selected from N, O and S,
wherein aryl is unsubstituted or substituted with one or two substituents independently selected from $CF_3$, halogen, $NH_2$, $OCF_3$, $C(O)NH_2$, $C_{1-6}$ alkyl or

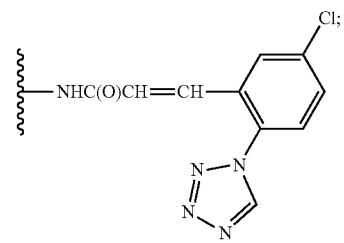

$R^5$ is
1) —C(O)$NHR^{51}$ wherein
$R^{51}$ is
a) 3-7-membered monocyclic saturated or unsaturated carbocycle,
b) 8-membered bicyclic saturated carbocycle, or
c) 9-membered bicyclic unsaturated heterocycle
wherein carbocycle is unsubstituted or substituted with one or two substituents independently selected from C(O)OC($C_{1-6}$ alkyl)($C_{1-6}$ alkyl)($C_{1-6}$ alkyl) or C(O)OH, and wherein heterocycle containing one or two heteroatoms selected from N, O and S, is unsubstituted or substituted with methyl,

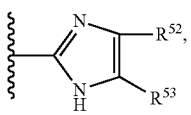

wherein
R$^{52}$ is
a) 3-7-membered monocyclic saturated or unsaturated carbocycle,
b) 6-membered unsaturated heterocycle containing 1 nitrogen atom, or
c) 9-membered bicyclic unsaturated heterocycle containing 1 or 2 heteroatoms, selected from N and O
wherein carbocycle is unsubstituted or substituted with with one or two substituents independently selected from CN, halogen, OC$_{1-6}$ alkyl, SO$_2$C$_{1-6}$ alkyl, CF$_3$, C(O)OC$_{1-6}$ alkyl, NH$_2$, NHC(O)OC$_{1-6}$ alkyl, NHC(O)C$_{1-6}$ alkyl, C(O)OC(CH$_3$)$_2$, C(O)OH, PO$_3$H$_2$, or PO$_3$(C$_{1-6}$ alkyl)$_2$, wherein heterocycle is unsubstituted or substituted with methyl, and wherein bicyclic heterocycle is unsubstituted or substituted with a =O, and
R$^{53}$ is hydrogen, halogen or C$_{1-6}$ alkyl, and

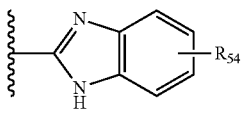

wherein
R$^{54}$ is hydrogen or halogen.
In one embodiment of the invention,
R$^2$ is
1) phenyl
2) R$^{21}$,
3) 5-6-membered saturated carbocycle,
4) —OR$^{21}$, or

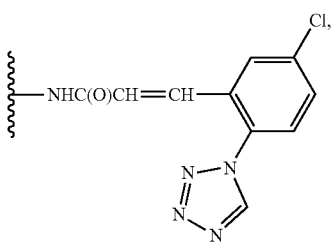

wherein R$^{21}$ is 5-6-membered saturated heterocycle containing one or two N heteroatoms,
wherein phenyl is unsubstituted or monosubstituted with CF$_3$, and saturated heterocycle is unsubstituted or monosubstituted with NH$_2$, SO$_2$CH$_3$ or COCH$_3$;
R$^6$ is
1) —CH=CH—R$^{63}$, or
2) R$^{62}$,
wherein R$^{63}$ is phenyl wherein R$^{63}$ is aryl which is mono, di or trisubstituted with a substituent independently selected from halogen, CF$_3$ and tetrazole, and R$^{62}$ is unsaturated carbocycle unsubstituted or substituted with one or two substituents independently selected from —CH$_2$NH$_2$, NH$_2$, C(CH$_3$)$_2$NH$_2$, C$_{1-6}$ alkyl, or C$_{3-8}$ cycloalkyl;
R$^4$ is
1) phenyl, or
2) cyclohexyl,
3) C$_{1-6}$ alkyl, or
4) —OR$^{42}$, wherein R$^{42}$ is a 6-membered monocyclic saturated heterocycle having one or two N atoms,
wherein phenyl is unsubstituted or substituted with one or two substituents independently selected from CF$_3$, halogen, NH$_2$, OCF$_3$, C(O)NH$_2$, C$_{1-6}$ alkyl or

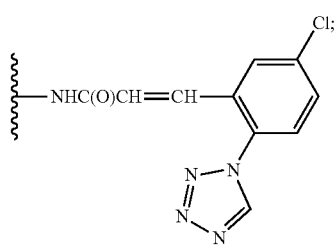

R$^5$ is
—C(O)NHR$^{51}$ wherein
R$^{51}$ is
a) 3-7-membered monocyclic saturated or unsaturated carbocycle,
b) 8-membered bicyclic saturated carbocycle, or
c) 9-membered bicyclic unsaturated heterocycle,
wherein carbocycle is unsubstituted or substituted with with one or two substituents independently selected from C(O)OC(C$_{1-6}$ alkyl)(C$_{1-6}$ alkyl) or C(O)OH, wherein heterocycle contains one or two heteroatoms selected from N, O and S, and wherein heterocycle is unsubstituted or substituted with methyl.
In another embodiment of the invention, R$^4$ is
1) phenyl,
2) cyclohexyl,
3) methyl or ethyl, or
4) —O—R$^{42}$, wherein R$^{42}$ is piperidinyl,
wherein phenyl is unsubstituted or substituted with one or two substituents independently selected from CF$_3$, halogen, NH$_2$, OCF$_3$, C(O)NH$_2$, C$_{1-6}$ alkyl or

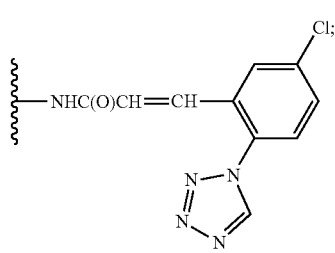

In another embodiment of the invention, R$^6$ is
1) —CH=CH—R$^{63}$, or
2) R$^{62}$,
wherein R$^{63}$ is phenyl substituted with chloro and tetrazole, and R$^{62}$ is phenyl unsubstituted or substituted with one or two substituents independently selected from —CH$_2$NH$_2$, or cyclopropyl.

In another embodiment of the invention, $R^6$ is

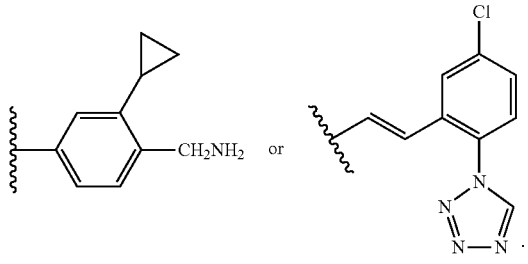 or 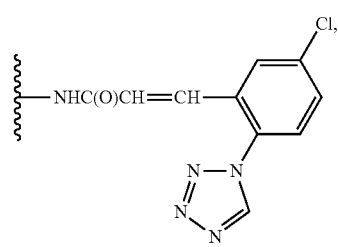

In another embodiment of the invention, $R^4$ is
1) phenyl,
2) cyclohexyl,
3) methyl or ethyl, or
4) —O—$R^{42}$.

In another embodiment of the invention, $R^4$ is

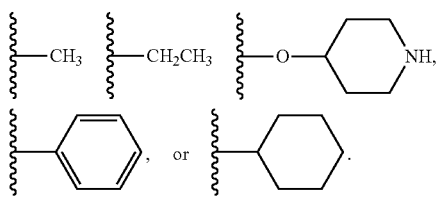

In another embodiment of the invention, $R^5$ is —C(O)NH$R^{51}$, wherein $R^{51}$ is
a) phenyl, or
b) 9-membered bicyclic unsaturated, unsubstituted heterocycle containing one or two N atoms,
wherein phenyl is unsubstituted or substituted with one or two of C(O)OH.

In another embodiment of the invention, $R^5$ is

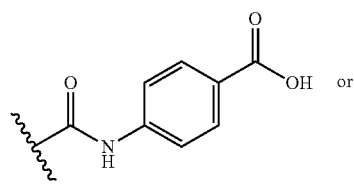

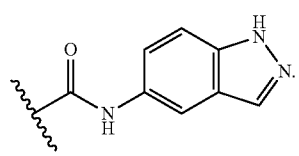

In another embodiment of the invention, $R^2$ is
1) phenyl
2) $R^{21}$, 3) cyclohexyl,
4) —O$R^{21}$, or

5)

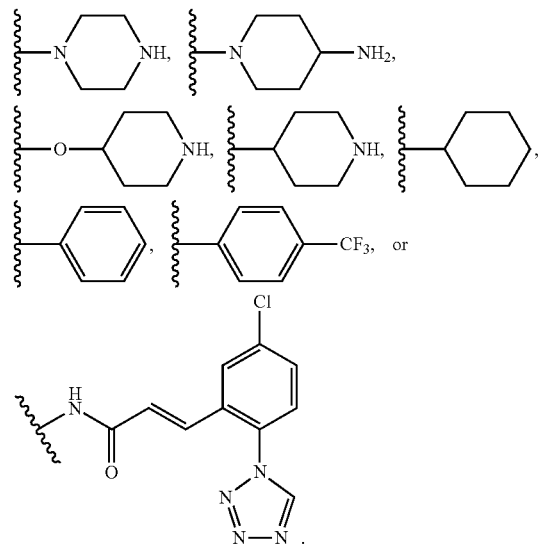

wherein $R^{21}$ is 6-membered saturated heterocycle containing one or two N heteroatoms,
wherein phenyl is unsubstituted or monosubstituted with CF$_3$, and saturated heterocycle is unsubstituted or monosubstituted with NH$_2$;

In another embodiment of the invention, $R^2$ is

In another embodiment of the invention, the compound is
(E)-4-(4-amino-1'-(3-(5-chloro-2-(1H-tetrazol-1-yl)phenyl)acryloyl)-5'-phenyl-[1,3'-bipiperidine]-6'-carboxamido)benzoic acid,
(E)-4-(1-(3-(5-chloro-2-(1H-tetrazol-1-yl)phenyl)acryloyl)-3-phenyl-5-(piperazin-1-yl)piperidine-2-carboxamido)benzoic acid,
4-({[4-amino-1'-{(2E)-3-[5-chloro-2-(1H-tetrazol-1-yl)phenyl]prop-2-enoyl}-5'-(1-methylethyl)-1,3'-bipiperidin-6'-yl]carbonyl}amino)benzoic acid,
4-{[(4-amino-1'-{(2E)-3-[5-chloro-2-(1H-tetrazol-1-yl)phenyl]prop-2-enoyl}-5'-cyclopropyl-1,3'-bipiperidin-6'-yl)carbonyl]amino}benzoic acid,
4-{[(4-amino-1'-{(2E)-3-[5-chloro-2-(1H-tetrazol-1-yl)phenyl]prop-2-enoyl}-5'-methyl-1,3'-bipiperidin-6'-yl)carbonyl]amino}benzoic acid,
4-({[(3'S,5'S,6'S)-4-amino-1'-{(2E)-3-[5-chloro-2-(1H-tetrazol-1-yl)phenyl]prop-2-enoyl}-5'-phenyl-1,3'-bipiperidin-6'-yl]carbonyl}amino)benzoic acid,
4-({[(3'R,5'R,6'R)-4-amino-1'-{(2E)-3-[5-chloro-2-(1H-tetrazol-1-yl)phenyl]prop-2-enoyl}-5'-phenyl-1,3'-bipiperidin-6'-yl]carbonyl}amino)benzoic acid, 4-(4-((E)-3-(5-chloro-2-(1H-tetrazol-1-yl)phenyl)acrylamido)-1'-((E)-3-(5-chloro-2-(1H-tetrazol-1-yl)phenyl)acryloyl)-5'-phenyl-[1,3'-bipiperidine]-6'-carboxamido)benzoic acid, 4-((2S,3S,5S)-1-((E)-3-(5-chloro-2-(1H-tetrazol-1-yl)phenyl)acryloyl)-3-phenyl-5-(piperidin-4-yloxy)piperidine-2-carboxamido)benzoic acid, 4-((2R,3R,5R)-1-((E)-3-(5-chloro-2-(1H-tetrazol-1-yl)phenyl)acryloyl)-3-phenyl-5-(piperidin-4-yloxy)piperidine-2-carboxamido)benzoic acid, (E)-4-(1-(3-(5-chloro-2-(1H-tetrazol-1-yl)phenyl)acryloyl)-3-phenyl-5-(piperidin-4-yloxy)piperidine-2-carboxamido)benzoic acid, 4-(1-((E)-3-(5-chloro-2-(1H-tetrazol-1-yl)phenyl)acryloyl)-5-phenyl-3-(piperidin-4-yloxy)piperidine-2-carboxamido)benzoic acid, methyl (4-{2-[4-amino-1'-{(2E)-3-[5-chloro-2-(1H-tetrazol-1-yl)phenyl]prop-2-enoyl}-5'-(4-fluorophenyl)-1,3'-bipiperidin-6'-yl]-1H-imidazol-4-yl}phenyl)carbamate, 1'-{(2E)-3-[5-chloro-2-(1H-tetrazol-1-yl)phenyl]prop-2-enoyl}-5'-(4-fluorophenyl)-6'-(4-pyridin-3-yl-1H-imidazol-2-yl)-1,3'-bipiperidin-4-amine, (3'S,5'S,6'S)-1'-{(2E)-3-[5-chloro-2-(1H-tetrazol-1-yl)phenyl]prop-2-enoyl}-5'-(4-fluorophenyl)-6'-(4-pyridin-3-yl-1H-imidazol-2-yl)-1,3'-bipiperidin-4-amine, 4-{2-[4-amino-1'-{(2E)-3-[3-chloro-2-fluoro-6-(trifluoromethyl)phenyl]prop-2-enoyl}-5'-(4-fluorophenyl)-1,3'-bipiperidin-6'-yl]1H-imidazol-5-yl}benzonitrile, 4-{2-[4-amino-1'-{(2E)-3-[3-chloro-2-fluoro-6-(trifluoromethyl)phenyl]prop-2-enoyl}-5'-(4-fluorophenyl)-1,3'-bipiperidin-6'-yl]-1H-imidazol-5-yl}benzonitrile, 4-{2-[4-amino-1'-{(2E)-3-[5-chloro-2-(1H-tetrazol-1-yl)phenyl]prop-2-enoyl}-5'-(4-fluorophenyl)-1,3'-bipiperidin-6'-yl]-1H-imidazol-5-yl}benzonitrile, methyl (4-{2-[4-amino-1'-{(2E)-3-[3-chloro-2-fluoro-6-(trifluoromethyl)phenyl]prop-2-enoyl}-5'-(4-fluorophenyl)-1,3'-bipiperidin-6'-yl]-1H-imidazol-5-yl}phenyl)carbamate, methyl (4-{2-[4-amino-1'-{(2E)-3-[3-chloro-2-fluoro-6-(trifluoromethyl)phenyl]prop-2-enoyl}-5'-(4-fluorophenyl)-1,3'-bipiperidin-6'-yl]-1H-imidazol-5-yl}phenyl)carbamate, methyl [4-(2-{4-amino-1'-[(2E)-3-(3-chloro-2,6-difluorophenyl)prop-2-enoyl]-5'-(4-fluorophenyl)-1,3'-bipiperidin-6'-yl}-1H-imidazol-4-yl)phenyl]carbamate, methyl (4-{2-[(3'S,5'S,6'S)-4-amino-1-{(2E)-3-[5-chloro-2-(1H-tetrazol-1-yl)phenyl]prop-2-enoyl}-5'-cyclopropyl-1,3'-bipiperidin-6'-yl]-1H-imidazol-4-yl}phenyl)carbamate, 4-((3R,5S,6S)-1-((E)-3-(5-chloro-2-(1H-tetrazol-1-yl)phenyl)acryloyl)-5-phenyl-[3,4'-bipiperidine]-6-carboxamido)benzoic acid trifluoroacetic acid salt, 4-((3R,5R,6S)-1-((E)-3-(5-chloro-2-(1H-tetrazol-1-yl)phenyl)acryloyl)-5-methyl-[3,4'-bipiperidine]-6-carboxamido)benzoic acid, 4-((3R,5R,6S)-1-(4-(aminomethyl)-3-cyclopropylbenzoyl)-5-methy-1-[3,4'-bipiperidine]-6-carboxamido)benzoic acid, methyl (4-{2-[(3R,5S,6S)-1-{(2E)-3-[5-chloro-2-(1H-tetrazol-1-yl)phenyl]prop-2-enoyl-}-5-cyclopropyl-3,4'-bipiperidin-6-yl]-1H-imidazol-4-yl}phenyl)carbamate, methyl (4-{2-[1-{(2E)-3-[5-chloro-2-(1H-tetrazol-1-yl)phenyl]prop-2-enoyl}-5-(4-fluorophenyl)-3,4'-bipiperidin-6-yl]-1H-imidazol-4-yl}phenyl)carbamate, methyl (4-{2-[(3R,5S,6S)-1-{(2E)-3-[5-chloro-2-(1H-tetrazol-1-yl)phenyl]prop-2-enoyl}-5-cyclopropyl-1'-(methylsulfonyl)-3,4'-bipiperidin-6-yl]1H-imidazol-4-yl}phenyl)carbamate, (2S,3S,5S)-1-{(2E)-3-[5-chloro-2-(1H-tetrazol-1-yl)phenyl]prop-2-enoyl}-3-(4-fluorophenyl)-N-1H-indazol-5-yl-5-morpholin-4-ylpiperidine-2-carboxamide, (2R,3R,5R)-1-{(2E)-3-[5-chloro-2-(1H-tetrazol-1-yl)phenyl]prop-2-enoyl}-3-(4-fluorophenyl)-N-1H-indazol-5-yl-5-piperazin-1-ylpiperidine-2-carboxamide, (2S,3S,5S)-1-{(2E)-3-[5-chloro-2-(1H-tetrazol-1-yl)phenyl]prop-2-enoyl}-3-(4-fluorophenyl)-N-1H-indazol-5-yl-5-piperazin-1-ylpiperidine-2-carboxamide, (2S,3S,5S)-5-(4-acetylpiperazin-1-yl)-1-{(2E)-3-[5-chloro-2-(1H-tetrazol-1-yl)phenyl]prop-2-enoyl}-3-(4-fluorophenyl)-N-1H-indazol-5-ylpiperidine-2-carboxamide, or a pharmaceutically acceptable salt thereof.

Reference to the preferred classes and subclasses set forth above is meant to include all combinations of particular and preferred groups unless stated otherwise.

Specific embodiments of the present invention include, but are not limited to the compounds identified herein as Examples 1 to 32, or pharmaceutically acceptable salts thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, and treating inflammatory disorders in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor XIa inhibitors and may have therapeutic value in, for example, preventing coronary artery disease. The compounds are selective Factor XIa inhibitors or dual inhibitors of Factor XIa and plasma kallikrein.

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Also included are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. When a particular configuration is depicted, that entantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^4$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Reference to the compounds of this invention as those of a specific formula or embodiment, e.g., Formula I or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, "alkyl" is intended to include both branched- and straight-chain saturated aliphatic hydrocarbon groups having the specified number of carbon atoms. Commonly used abbreviations for alkyl groups are used throughout the specification, e.g., methyl may be represented by "Me" or $CH_3$ or a symbol that is an extended bond as the terminal group, e.g. "⸺", ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

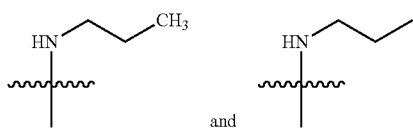

and have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically acceptable salts.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

When any variable occurs more than one time in any constituent or in formula I, its definition on each occurrence is independent of its definition at every other occurrence. Also, combinations of substituents and/or variables are permissible only if such combinations result in stable compounds.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted herein, alkyl groups may be unsubstituted, or substituted with 1 to 3 substituents on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_0$-$C_6$ alkyl)C(O)NH—, $H_2$N—C(NH)—, —O($C_1$-$C_6$ alkyl)$CF_3$, HC(O)—, ($C_1$-$C_6$ alkyl)C(O)—, HOC(O)—, ($C_1$-$C_6$ alkyl)OC(O)—, HO($C_1$-$C_6$ alkyl)-, ($C_1$-$C_6$ alkyl)O($C_1$-$C_6$ alkyl)-, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, HOC(O)NH—, ($C_1$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted, the term "halogen" means fluorine, chlorine, bromine or iodine.

Except where noted, the term "heterocycle" refers to a stable 4- to 7-membered mono-cyclic or stable 7- to 12-membered bicyclic or stable 12- to 14-membered tricyclic heteroatom-containing ring system unsubstituted or substituted with $C_{1-4}$ alkyl or halogen, any ring of which may be saturated or unsaturated, and which consists of carbon atoms and from one to four heteroatoms independently selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyridyl N-oxide, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl.

Except where noted herein, the term "heteroaryl" refers to a monocyclic unsaturated heterocycle having a specified number of atom members (e.g., 4, 5, 6 or 7-membered), including a specified number of heteroatoms (e.g., 1, 2, 3 or 4 heteroatoms independently selected from N, O or S), or a bicyclic unsaturated ring system having a specified number of atom members (e.g., 7, 8, 9, 10, 11 or 12-membered) including a specified number of heteroatoms (e.g., 1, 2, 3, 4, 5, 6, 7, 8, 9 or 10 heteroatoms independently selected from N, S or O) or a tricyclic unsaturated ring system having a specified number of atom members (e.g., 12-, 13- or 14-membered) including a specified number of heteroatoms (e.g., 1, 2, 3, 4, 5, 6, 7, 8, 9 or 10 heteroatoms independently selected from N, S or O) e.g., 5-membered rings containing one nitrogen (pyrrole), one oxygen (furan) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen atoms, five-membered aromatic rings containing one oxygen, one nitrogen or one sulfur atom, five-membered aromatic rings containing two heteroatoms independently selected from oxygen, nitrogen and sulfur, 6-membered rings containing one nitrogen (pyridine), or one oxygen (pyran) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Examples of such ring systems are furanyl, thienyl, pyrrolyl, pyridinyl, pyrimidinyl, indolyl, imidazolyl, triazinyl, thiazolyl, isothiazolyl, pyridazinyl, pyrazolyl, oxazolyl, oxadiazolyl, triazolyl and isoxazolyl.

The term "saturated heterocycle" refers to a saturated monocyclic 5- to 8-membered ring having 1-4 heteroatoms selected from N, O and S, or a 7- to 12-membered saturated bicyclic ring system having 1-6 heteroatoms selected from N, O and S, or a 12- to 14-membered ring having 1-4 heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Except where noted herein, the term "carbocycle" (and variations thereof such as "carbocyclic" or "carbocyclyl") as used herein, unless otherwise indicated, refers to a $C_3$ to $C_8$ monocyclic saturated or unsaturated ring, e.g., $C_{3-8}$ monocyclic carbocycle, or a $C_9$ to $C_{12}$ bicyclic saturated or unsaturated ring, e.g., $C_{9-12}$ bicyclic carbocycle. The carbocycle may be attached to the rest of the molecule at any carbon atom which results in a stable compound. Saturated carbocyclic rings include, for example, "cycloalkyl" rings, e.g., cyclopropyl, cyclobutyl, etc. Unsaturated carbocyclic rings include, for example, "aryl" rings. Unsaturated bicyclic carbocyclic ring systems include fused ring systems where all ring system members are carbon atoms and where at least one of the fused rings is not saturated.

Except where noted, the term "aryl" refers to a stable 6- to 10-membered mono- or bicyclic ring system such as phenyl, or naphthyl. The aryl ring can be unsubstituted or substituted with one or more of $C_{1-4}$ alkyl, hydroxyl, alkoxy, halogen, or amino.

"Celite®" (Fluka) diatomite is diatomaceous earth, and can be referred to as "celite".

Except where noted herein, aryl groups and carbocycle groups may be unsubstituted, or substituted on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, HS(O)$_{0-2}$—, ($C_1$-$C_6$ alkyl)S(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$, ($C_1$-$C_6$ alkyl)C(O)NH—, HC(O)NH—, $H_2$N—C(NH)—, —O($C_1$-$C_6$ alkyl)$CF_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)C(O)$_{1-2}$($C_1$-$C_6$ alkyl)-, ($C_1$-$C_6$ alkyl)C(O)$_{1-2}$—, HC(O)$_{1-2}$($C_1$-$C_6$ alkyl)-, ($C_1$-$C_6$ alkyl)OC(O)NH—, HOC(O)NH—, —P(O)(OH)$_2$, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted herein, heterocycles may be unsubstituted, or substituted on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$ ($C_1$-$C_6$ alkyl)-, HS(O)$_{0-2}$($C_1$-$C_6$ alkyl)-, ($C_1$-$C_6$ alkyl) S(O)$_{0-2}$—, ($C_1$-$C_6$ alkyl)C(O)NH—, HC(O)NH—, $H_2$N—C (NH)—, —O($C_1$-$C_6$ alkyl)$CF_3$, HC(O)—, ($C_1$-$C_6$ alkyl)C (O)—, ($C_1$-$C_6$ alkyl)OC(O)—, HOC(O)—, ($C_1$-$C_6$ alkyl)O ($C_1$-$C_6$ alkyl)-, HO($C_1$-$C_6$ alkyl)-, ($C_1$-$C_6$ alkyl)O—, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$, ($C_1$-$C_6$ alkyl)OC(O)NH—, HOC(O) NH—, silyl groups (including trimethylsilyl, tetramethylsilyl, or supersilyl groups such as tri(trimethylsilyl)silyl or a silicon group connected to tert butyl groups), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, —C(O)$C_{1-6}$ alkyl, —C(O)NH$C_1$-$C_6$ alkyl, —C(O) NH$_2$, —$C_1$-$C_6$ alkylC(O)NH$_2$, —$C_1$-$C_6$ alkylOC(O)NH$_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, where such substitution results in formation of a stable compound.

Except where noted herein, structures containing substituent variables such as variable "R" below:

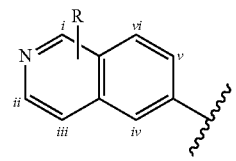

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also includes derivatives of the compounds of Formula I, acting as prodrugs and solvates. Prodrugs, following administration to the patient, are converted in the body by normal metabolic or chemical processes, such as through hydrolysis in the blood, to the compound of Formula 1. Such prodrugs include those that demonstrate enhanced bioavailability, tissue specificity, and/or cellular delivery, to improve drug absorption of the compound of Formula I. The effect of such prodrugs may result from modification of physicochemical properties such as lipophilicity, molecular weight, charge, and other physicochemical properties that determine the permeation properties of the drug.

The preparation of pharmaceutically acceptable salts from compounds of the Formula I capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula I form stable alkali metal, alkaline earth metal or optionally substituted ammonium salts. If the compounds of the Formula I have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula I and/or of a pharmaceutically acceptable salt of the compound of the Formula I and/or an optionally stereoisomeric form of the compound of the Formula I or a pharmaceutically acceptable salt of the stereoisomeric form of the compound of Formula I, together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Factor XIa or dual Factor XIa/plasma kallikrein inhibition are useful not only in the anticoagulant therapy of individuals having thrombotic conditions, but are useful whenever inhibition of blood coagulation is required such as to prevent coagulation of stored whole blood and to prevent coagulation in other biological samples for testing or storage. Thus, the Factor XIa or dual Factor XIa/plasma kallikrein inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XIa inhibitors or dual Factor XIa/plasma kallikrein inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XIa inhibitors or dual Factor XIa/plasma kallikrein inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor XIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula I can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIa inhibitors or dual Factor XIa/plasma kallikrein inhibitors can also be co-administered with suitable anticoagulants, including, but not limited to, other Factor XIa inhibitors, thrombin inhibitors, thrombin receptor antagonists, Factor VIIa inhibitors, Factor Xa inhibitors, Factor IXa inhibitors, Factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epler023anone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)-N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazosin, prazosin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin and remogliflozin), and SGLT-3; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XIa inhibitors or Factor XIa/plasma kallikrein inhibitors of the invention in combination with other suitable anti-platelet agents, anticoagulation agents, or thrombolytic agents may be the same as those doses of Factor XIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

Abbreviations used herein are as follows:
Boc is tert-butyloxycarbonyl
BOP Cl is bis(2-oxo-3-oxazolidinyl)phosphinic chloride
BOP reagent is benzotriazol-1-yloxy tris(dimethylamino) phosphonium hexafluorophosphate
celite is Celite® diatomaceous earth
DCC is 1,3-dicyclohexylcarbodiimide
DCM is dichloromethane
DIPEA is diisopropylethylamine
DMF is N,N-dimethylformamide
EDC is N-(3-dimethylaminopropyl)-N'-ethylcarbodiimide hydrochloride
Et is ethyl
HATU is O-(7-azabenzotriazol-1-yl)-N,N,N',N'-tetramethyluronium hexafluorophosphate
HPLC is high performance liquid chromatography
IPA is isopropyl alcohol
LCMS is Liquid chromatography-mass spectrometry
Me is methyl
Ph is phenyl PyBOP is benzotriaxole-1-yl-oxy-tris-pyrrolidino-phosphonium hexafluorophosphate SFC is supercritical fluid chromatography TEA is triethylamine TFA is trifluoroacetic acid THF is tetrahydrofuran WSC HCl is 1-ethyl-3-(3'-dimethylaminopropyl)carbodiimide hydrochloride Also, TLC is thin layer chromatography; Ts is tosyl; UV is ultraviolet; W is watts; wt. % is percentage by weight; x g is times gravity; $\alpha_D$ is the specific rotation of polarized light at 589 nm; ° C. is degrees Celsius; % w/v is percentage in weight of the former agent relative to the volume of the latter agent.

Methods for Making the Compounds of Present Invention

General Methods

The compounds of the present invention can be readily produced from known compounds or commercially available compounds by, for example, known processes described in published documents, and produced by production processes described below. The present invention is not limited to the production processes described below. The invention also includes processes for the preparation of compounds of the invention.

It should be noted that, when compounds of the present invention synthesized has a reactive group such as hydroxy group, amino group, carboxyl group, or thiol group as its substituent, such group may be adequately protected with a protective group in each reaction step and the protective group may be removed at an adequate stage. The process of such introduction and removal of the protective group may be adequately determined depending on the group to be protected and the type of the protective group, and such introduction and removal are conducted, for example, by the process described in the review section of Greene, T. W., et. al., "*Protective Groups in Organic Synthesis*", 2007, 4th Ed., Wiley, New York, or Kocienski, P., "*Protecting Groups*" 1994, Thieme. Unless otherwise indicated, all variables used in the Schemes below are as defined above.

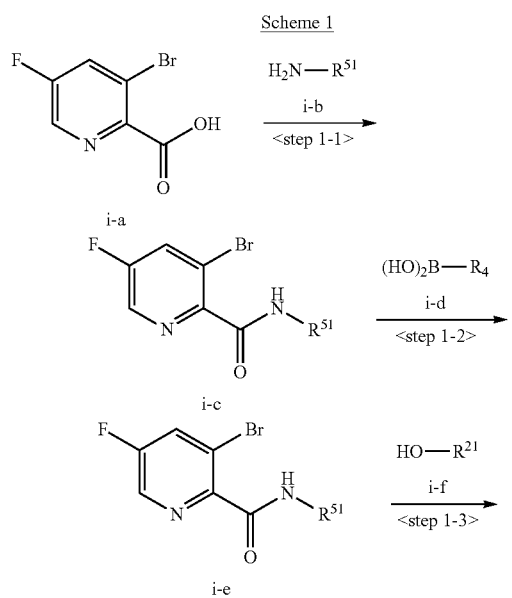

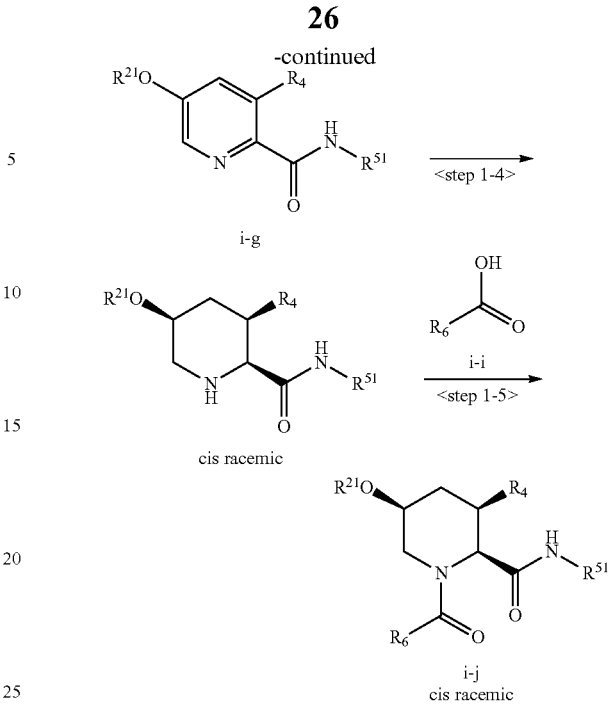

<Step 1-1>

A compound represented by formula (i-c) can be produced by allowing 3-bromo-5-fluropicolinic acid (i-a) to react with a compound represented by formula (i-b) by a well-known or a process similar to that described in published documents, for example, Organic synthesis IV, Acids, amino acids, and peptides, pp. 191-309, 1992, Maruzen Co., Ltd., in the presence of a condensing agent such as 1,3-dicyclohexylcarbodiimide (DCC), 1-ethyl-3-(3'-dimethylaminopropyl)carbodiimide hydrochloride (WSC.HCl or EDC HCl), O-(7-azabenzotriazol-1-yl)-N,N,N',N'-tetramethyluronium hexafluorophosphate (HATU), benzotriazol-1-yloxy tris(dimethylamino)phosphonium hexafluorophosphate (BOP reagent), or bis(2-oxo-3-oxazolidinyl)phosphinic chloride (BOP-Cl), in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or N,N-diisopropylethyl amine at a temperature in the range of 0° C. to the solvent reflux temperature.

<Step 1-2>

A compound represented by formula (i-e) can be produced from the reaction of a compound represented by formula (i-c) and a compound represented by (i-d) by a well-known or similar process that is described in published documents, for example, Metal Catalyzed Cross-Coupling Reactions, $2^{nd}$ Edition, 2004, Wiley-VCH, in the presence of a palladium catalyst such as tetrakis(triphenylphosphine)palladium(0), bis(triphenylphosphine)palladium(II) dichloride, or (1,1'-bis(diphenylphosphino)-ferrocene)palladium(II) dichloride, an inorganic base such as sodium carbonate, potassium carbonate, or potassium phosphate. The reaction can be carried out with water or without water and a solvent which is inactive to the reaction, such as toluene, N,N-dimethylformamide, dioxane, or a mixed solvent thereof at a temperature in the range of 90° C. to 120° C. using conventional or microwave heating.

<Step 1-3>

A compound represented by formula (i-g) can be produced by allowing a compound represented by formula (i-e) to react with a compound represented by formula (i-f) by a well-known substitutiton reaction under the influence of base such as, potassium phosphate, cesium carbonate, potassium tert-butoxide, sodium hydride, lithium hydroxide, sodium hydroxide, potassium hydroxide, lithium carbonate, sodium carbonate, or potassium carbonate, triethyl amine, diehtylisopropyl amine using a solvent which is inactive to the reaction, such as an ethereal solvent, e.g., diethyl ether, tetrahydrofuran, 1,2-dimethoxyethane, 1,4-dioxane, polar solvents such as N,N-dimethylformamide, and dimethyl sulfoxide; or an aromatic hydrocarbon solvent, e.g., toluene or benzene or a mixed solvent thereof at a temperature in the range of room temperature to the solvent-reflux temperature.

<Step 1-4>

A compound represented by formula (i-h) can be produced by allowing a compound represented by formula (i-g) to react with hydrogen gas by a well-known or similar process to that described in published documents, for example, Metal Catalyzed Reactions of Hydrocarbons, pp. 437-471, 2005, Springer US, in the presence of hydrogen gas and a catalyst such as platinum (IV) oxide, rhodium on alumina, rhodium on carbon, Raney nickel, or rhodium (III) oxide, or mixtures thereof. The reaction can be performed with or without the addition of an acid such as hydrochloric acid, and it can be occur in an inert solvent such as methanol, ethanol, 2-propanol, or water, or mixtures thereof, at room temperature and hydrogen pressures ranging from atmospheric pressure to 60 psi. The process as described above can generate a compound represented by formula (i-f) as a racemic mixture of cis-2,3,5-trisubstituted piperidines.

<Step 1-5>

A compound represented by formula (i j) can be produced by allowing a compound represented by formula (i-h) to react with a compound of formula (i-i) by a well-known or similar process to that described in published documents, for example, Organic synthesis IV, Acids, amino acids, and peptides, pp. 191-309, 1992, Maruzen Co., Ltd., in the presence of a condensing agent such as 1,3-dicyclohexyl-carbodiimide (DCC), 1-ethyl-3-(3'-dimethylaminopropyl) carbodiimide hydrochloride (WSC.HCl or EDC HCl), O-(7-azabenzotriazol-1-yl)-N,N,N',N'-tetramethyluronium hexafluorophosphate (HATU), benzotriazol-1-yloxy tris(dimethylamino)-phosphonium hexafluorophosphate (BOP reagent), bis(2-oxo-3-oxazolidinyl)phosphinic chloride (BOP-Cl), or (benzotriazol-1-yloxy)tripyrrolidinophosphonium hexafluorophosphate (PyBOP) in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethyl-formamide, or an alcoholic solvent, e.g., methanol, ethanol, or 2-propanol, in the presence or absence of a base such as triethylamine or N,N-diisopropylethyl amine at a temperature in the range of 0° C. to the solvent reflux temperature. The process as described above can generate a compound of formula (i-h) as a racemic mixture of cis 2,3,5-trisubstituted piperidines. A compound of formula (i-h) can be obtained as a single enantiomer using a chiral resolution process such as chiral preparatory HPLC or chiral supercritical fluid chromatography (SFC).

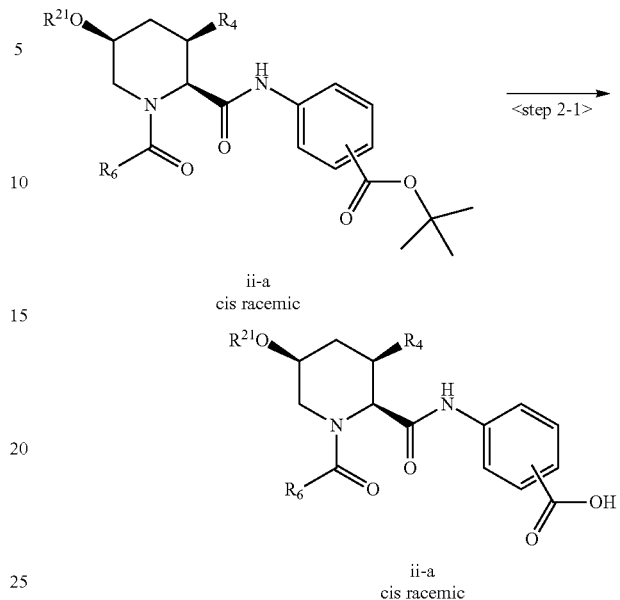

Scheme 2 ii-a
cis racemic ii-a
cis racemic

<Step 2-1>

In the specific case where a compound of formula (i j) (Scheme 1) contains a tert-butyl ester group, as represented by a compound of formula (ii-a), a carboxylic acid compound represented by formula (ii-b) can be produced following a well-known process or a process similar to that described in published documents, for example, Greene, T. W., et. al., *Protective Groups in Organic Synthesis* (2007), 4th Ed., in the presence of an acid such as trifluoroacetic acid, formic acid, hydrochloric acid, or acetic acid in a solvent which is inactive to the reaction, such as a halogenated solvent, e.g., dichloromethane or chloroform, or an ethereal solvent, e.g., dioxane or tetrahydrofuran, at a temperature in the range of 0° C. to the solvent reflux temperature. The process as described above can generate a compound of formula (ii-b) as a racemic mixture of cis 2,3,5-trisubstituted piperidines. A compound of formula (ii-b) can be obtained as a single enantiomer using a chiral resolution process such as chiral preparatory HPLC or chiral supercritical fluid chromatography (SFC).

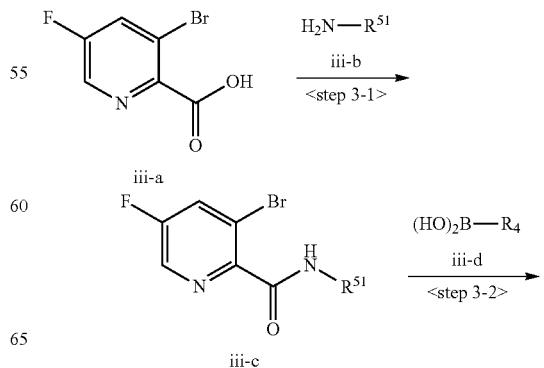

Scheme 3 iii-a iii-c

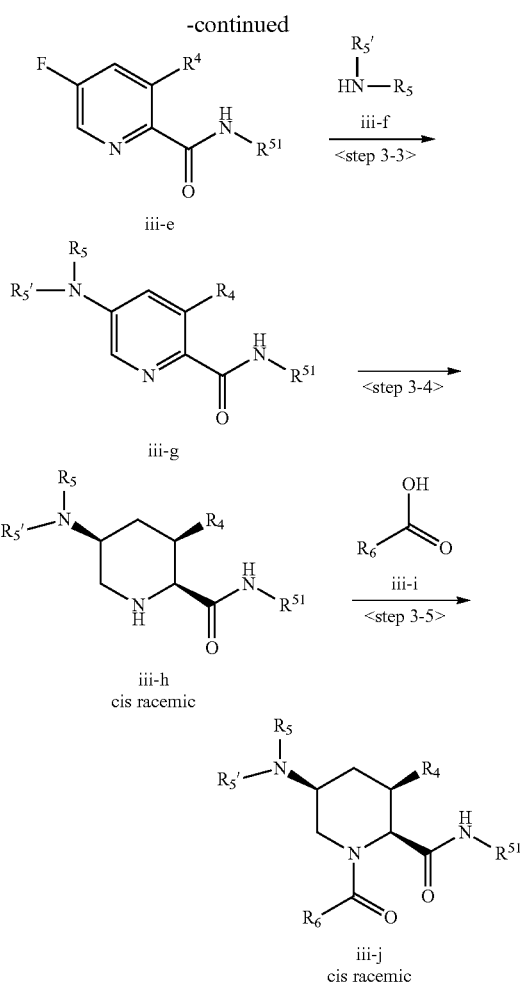

$R^5$ and $R^{5'}$ are independently hydrogen, $C_{1-6}$ alkyl, amide, sulfonamide, or form a heterocycle with NH <Step 3-1>

A compound represented by formula (iii-c) can be produced by allowing 3-bromo-5-fluropicolinic acid (iii-a) to react with a compound represented by formula (iii-b) by a well-known or a process similar to that described in published documents, for example, Organic synthesis IV, Acids, amino acids, and peptides, pp. 191-309, 1992, Maruzen Co., Ltd., in the presence of a condensing agent such as 1,3-dicyclohexylcarbodiimide (DCC), 1-ethyl-3-(3'-dimethylaminopropyl)carbodiimide hydrochloride (WSC.HCl or EDC HCl), O-(7-azabenzotriazol-1-yl)-N,N,N',N'-tetramethyluronium hexafluorophosphate (HATU), benzotriazol-1-yloxy tris(dimethylamino)phosphonium hexafluorophosphate (BOP reagent), or bis(2-oxo-3-oxazolidinyl)phosphinic chloride (BOP-Cl), in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or N,N-diisopropylethyl amine at a temperature in the range of 0° C. to the solvent reflux temperature.

<Step 3-2>

A compound represented by formula (iii-e) can be produced from the reaction of a compound represented by formula (iii-c) and a compound represented by (iii-d) by a well-known or similar process that is described in published documents, for example, Metal Catalyzed Cross-Coupling Reactions, 2$^{nd}$ Edition, 2004, Wiley-VCH, in the presence of a palladium catalyst such as tetrakis(triphenylphosphine)palladium(0), bis(triphenylphosphine)palladium(II) dichloride, or (1,1'-bis(diphenylphosphino)-ferrocene)palladium(II) dichloride, an inorganic base such as sodium carbonate, potassium carbonate, or potassium phosphate. The reaction can be carried out with water or without water and a solvent which is inactive to the reaction, such as toluene, N,N-dimethylformamide, dioxane, or a mixed solvent thereof at a temperature in the range of 90° C. to 120° C. using conventional or microwave heating.

<Step 3-3>

A compound represented by formula (iii-g) can be produced by allowing a compound represented by formula (iii-e) to react with a compound represented by formula (iii-f) by a well-known substitution reaction under the influence of base such as, potassium phosphate, cesium carbonate, potassium tert-butoxide, sodium hydride, lithium hydroxide, sodium hydroxide, potassium hydroxide, lithium carbonate, sodium carbonate, or potassium carbonate, triethyl amine, diehtylisopropyl amine using a solvent which is inactive to the reaction, such as an ethereal solvent, e.g., diethyl ether, tetrahydrofuran, 1,2-dimethoxyethane, 1,4-dioxane, polar solvents such as N,N-dimethylformamide, and dimethyl sulfoxide; or an aromatic hydrocarbon solvent, e.g., toluene or benzene or a mixed solvent thereof at a temperature in the range of room temperature to the solvent-reflux temperature.

<Step 3-4>

A compound represented by formula (iii-h) can be produced by allowing a compound represented by formula (iii-g) to react with hydrogen gas by a well-known or similar process to that described in published documents, for example, Metal Catalyzed Reactions of Hydrocarbons, pp. 437-471, 2005, Springer US, in the presence of hydrogen gas and a catalyst such as platinum (IV) oxide, rhodium on alumina, rhodium on carbon, Raney nickel, or rhodium (III) oxide, or mixtures thereof. The reaction can be performed with or without the addition of an acid such as hydrochloric acid, and it can be occur in an inert solvent such as methanol, ethanol, 2-propanol, or water, or mixtures thereof, at room temperature and hydrogen pressures ranging from atmospheric pressure to 60 psi. The process as described above can generate a compound represented by formula (iii-h) as a racemic mixture of cis-2,3,5-trisubstituted piperidines.

<Step 3-5>

A compound represented by formula (iii-j) can be produced by allowing a compound represented by formula (iii-h) to react with a compound of formula (iii-i) by a well-known or similar process to that described in published documents, for example, Organic synthesis IV, Acids, amino acids, and peptides, pp. 191-309, 1992, Maruzen Co., Ltd., in the presence of a condensing agent such as 1,3-dicyclohexylcarbodiimide (DCC), 1-ethyl-3-(3'-dimethylaminopropyl)carbodiimide hydrochloride (WSC.HCl or EDC HCl), O-(7-azabenzotriazol-1-yl)-N,N,N',N'-tetramethyluronium hexafluorophosphate (HATU), benzotriazol-1-yloxy tris(dimethylamino)-phosphonium hexafluorophosphate (BOP reagent), bis(2-oxo-3-oxazolidinyl)phosphinic chloride (BOP-Cl), or (benzotriazol-1-yloxy)tripyrrolidinophosphonium hexafluorophosphate (PyBOP) in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethyl-formamide, or an alcoholic solvent, e.g., methanol, ethanol, or 2-propanol, in the presence or absence of a base such as triethylamine or N,N-diisopropylethyl amine at a temperature in the range of 0° C. to the solvent reflux temperature. The process as described above can generate a compound of formula (iii-h) as a racemic mixture of cis 2,3,5-trisubstituted piperidines. A compound of formula (iii-h) can be obtained as a single enantiomer using a chiral resolution process such as chiral preparatory HPLC or chiral supercritical fluid chromatography (SFC).

Scheme 4

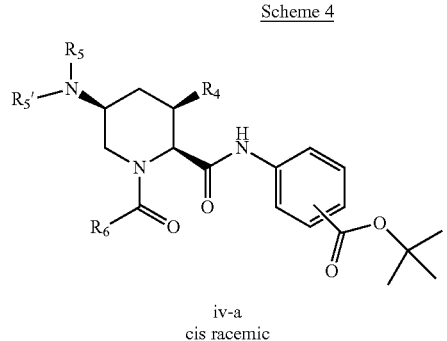

iv-a
cis racemic

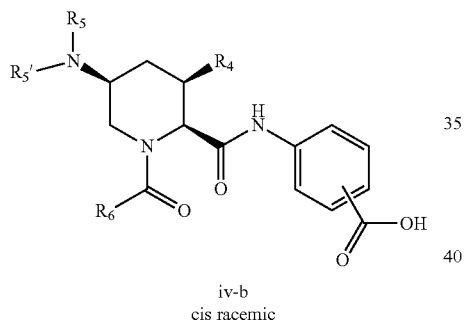

iv-b
cis racemic

<Step 4-1>

In the specific case where a compound of formula (iii j) (Scheme 3) contains a tert-butyl ester group, as represented by a compound of formula (iv-a), a carboxylic acid compound represented by formula (iv-b) can be produced following a well-known process or a process similar to that described in published documents, for example, Greene, T. W., et. al., *Protective Groups in Organic Synthesis* (2007), 4th Ed., in the presence of an acid such as trifluoroacetic acid, formic acid, hydrochloric acid, or acetic acid in a solvent which is inactive to the reaction, such as a halogenated solvent, e.g., dichloromethane or chloroform, or an ethereal solvent, e.g., dioxane or tetrahydrofuran, at a temperature in the range of 0° C. to the solvent reflux temperature. The process as described above can generate a compound of formula (iv-b) as a racemic mixture of cis 2,3,5-trisubstituted piperidines. A compound of formula (iv-b) can be obtained as a single enantiomer using a chiral resolution process such as chiral preparatory HPLC or chiral supercritical fluid chromatography (SFC).

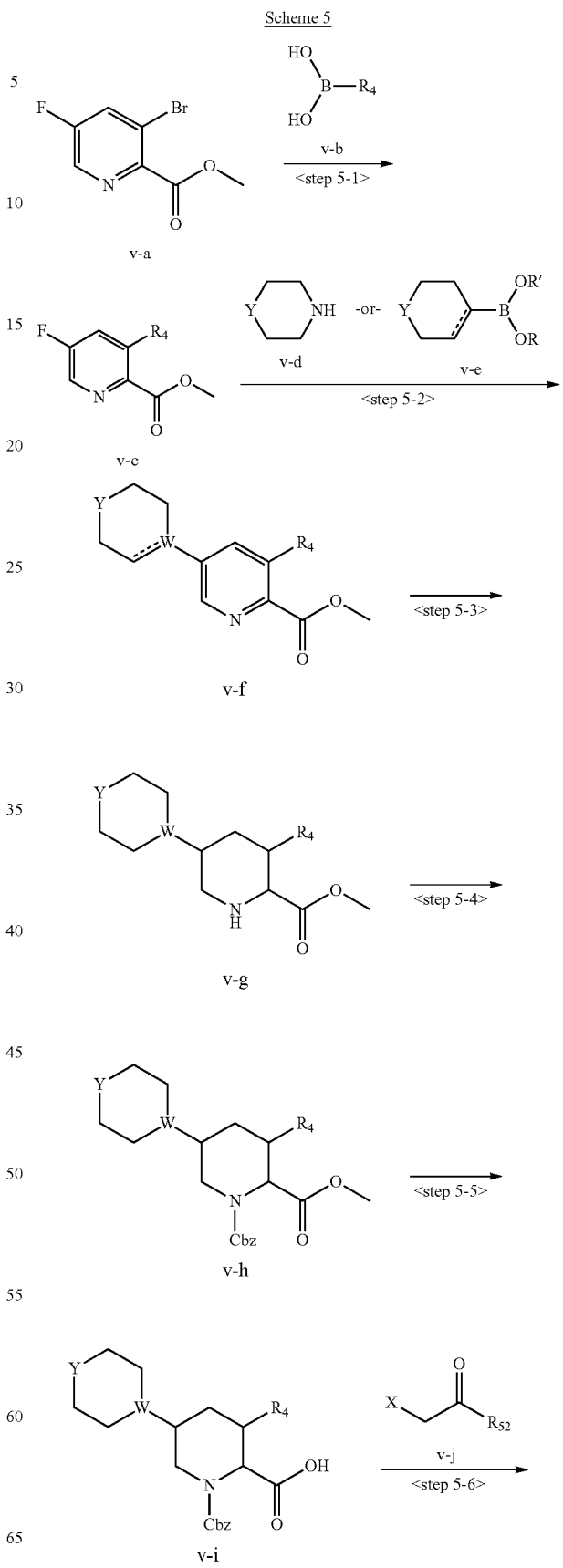

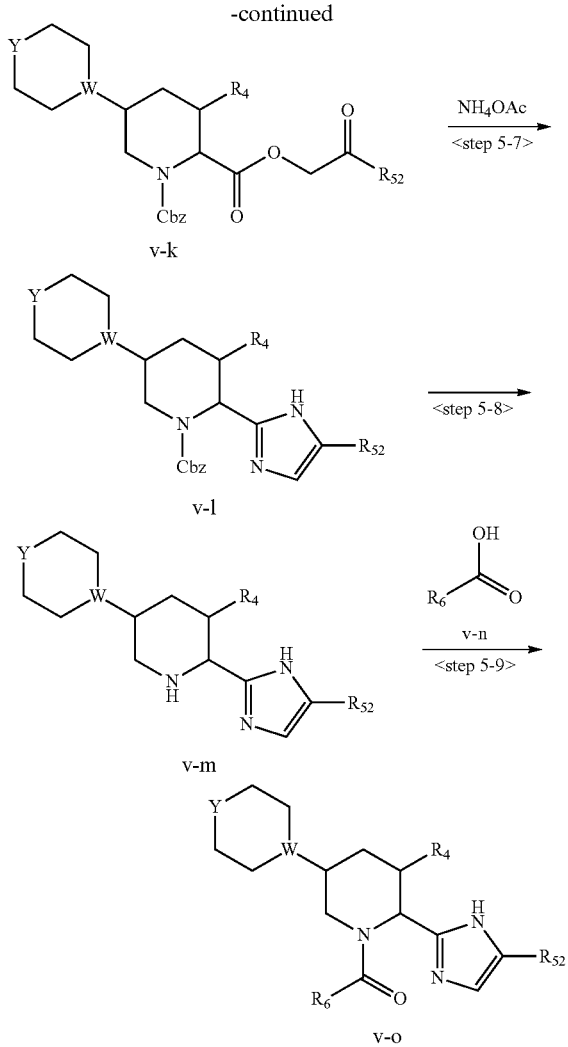

<Step 5-1>

A compound represented by formula (v-c) can be produced by allowing methyl 3-bromo-5-fluoropicolinate (v-a) to react with a boronic acid (or corresponding boronate ester) represented by formula (v-b) by a well-known or similar process that is described in published documents, for example, Metal Catalyzed Cross-Coupling Reactions, 2$^{nd}$ Edition, 2004, Wiley-VCH, in the presence of a palladium catalyst such as tetrakis(triphenylphosphine)palladium(0), bis(triphenylphosphine)palladium(II) dichloride, or (1,1'-bis(diphenylphosphino)-ferrocene)palladium(II) dichloride, an inorganic base such as sodium carbonate, potassium carbonate, or potassium phosphate. The reaction can be carried out with water or without water and a solvent which is inactive to the reaction, such as toluene, N,N-dimethylformamide, dioxane, or a mixed solvent thereof at a temperature in the range of 90° C. to 120° C. using conventional or microwave heating.

<Step 5-2>

A compound represented by formula (v-f), in which W is a nitrogen, can be produced from the reaction of a compound represented by formula (v-c) and a compound represented by (v-d) by a nucleophilic substitution reaction which is well-known to one skilled in the art. This reaction may occur in the presence of a base such as potassium phosphate, cesium carbonate, potassium tert-butoxide, sodium hydride, lithium hydroxide, sodium hydroxide, potassium hydroxide, lithium carbonate, sodium carbonate, or potassium carbonate, triethyl amine or diethylisopropyl amine using a solvent which is inactive to the reaction, such as an ethereal solvent, e.g., diethyl ether, tetrahydrofuran, 1,2-dimethoxyethane, 1,4-dioxane, polar solvents such as N,N-dimethylformamide, and dimethyl sulfoxide; or an aromatic hydrocarbon solvent, e.g., toluene or benzene or a mixed solvent thereof at a temperature in the range of room temperature to the solvent-reflux temperature. The reaction may be carried out using conventional heating or microwave irradiation.

A compound represented by formula (v-f), in which W is a carbon, can be produced from the reaction of a compound represented by formula (v-c) and a boronate ester compound represented by (v-e) by a Suzuki coupling reaction (Tetrahedron Letters, 2000, vol. 41, pages 3705-3708.). This reaction may be carried out in the presence of a palladium catalyst such as 1,1' bis(diphenylphosphino)ferrocene-palladium(II)dichloride and a base such as potassium carbonate, sodium carbonate, or potassium phosphate. The reaction may occur in an inert solvent such as dioxane, THF, or DMF at temperatures in the range of 90° C. to 120° C. using conventional or microwave heating.

<Step 5-3>

A compound represented by formula (v-g) can be produced by allowing a compound represented by formula (v-f) to react with hydrogen gas by a well-known or similar process to that described in published documents, for example, Metal Catalyzed Reactions of Hydrocarbons, pp. 437-471, 2005, Springer US, in the presence of hydrogen gas and a catalyst such as platinum (IV) oxide, rhodium on alumina, rhodium on carbon, or rhodium (III) oxide, or mixtures thereof. The reaction can be performed with or without the addition of an acid such as hydrochloric acid, and it can occur in an inert solvent such as methanol, ethanol, 2-propanol, or water, or mixtures thereof, at room temperature and hydrogen pressures ranging from atmospheric pressure to 60 psi. The process as described above can generate a compound represented by formula (v-g) as a racemic mixture of cis-2,3,5-trisubstituted piperidines.

<Step 5-4>

A compound represented by formula (v-h) can be produced by allowing a compound represented by formula (v-g) to react with benzyl chloroformate in the presence of an amine base such as triethylamine or diisopropylethylamine. The reaction may be carried out in an inert solvent such as dichloromethane at a temperature in the range of 0° C. and room temperature.

<Step 5-5>

A compound represented by formula (v-i) can be produced by a basic hydrolysis reaction, which is well known to those skilled in the art. The reaction may occur by allowing a compound represented by formula (v-h) to react with a alkaline hydroxide such as lithium hydroxide, sodium hydroxide, or potassium hydroxide. The reaction may be carried out in an inert solvent such as THF with or without the addition of water and in a temperature in the range of 0° C. and the reflux temperature.

<Step 5-6>

A compound represented by formula (v-k) may be produced by allowing the intermediate (v-i) to react with a properly substituted α-haloketone (v-j), where X is Cl, Br, or I, following a well-known process or a process similar to that described in published documents, for example, Contour-Galcera, M.-O., Poitout, L.; Moinet, C.; Morgan, B.; Gordon, T.; Roubert, P.; Thurieau, C. Bioorganic and Medicinal Chemistry Letters, 2001, Volume 11, Issue 5, pages 741-745, in the presence of a base such as potassium carbonate, sodium carbonate, cesium carbonate, triethylamine, or N,N-diisopropylethylamine in a solvent such as N,N-dimethylformamide, ethanol, methanol, water, or mixtures thereof, at a temperature between room temperature and 60° C.

<Step 5-7>

A compound represented by formula (v-l) may be produced by allowing a compound of formula (v-k) to react with ammonium acetate using a process similar to that described in published documents, for example, Contour-Galcera, M.-O., Poitout, L.; Moinet, C.; Morgan, B.; Gordon, T.; Roubert, P.; Thurieau, C. Bioorganic and Medicinal Chemistry Letters, 2001, Volume 11, Issue 5, pages 741-745. This process may occur in an inert solvent such as toluene, xylenes, or acetic acid, or mixtures thereof, at temperatures ranging from 110° C. and 150° C. The reaction can proceed using conventional heating or microwave irradiation.

<Step 5-8>

A compound represented by formula (v-m) may be produced by allowing a compound of formula (v-l) to react with hydrogen gas in the presence of a catalyst such as palladium on carbon. This reaction may occur in an inert solvent such as ethyl acetate for several hours.

<Step 5-9>

The compound of the invention represented by formula (v-o) may be produced by allowing a compound of formula (v-m) to react with a carboxylic acid of formula (v-n) by a well-known or similar process to that described in published documents, for example, Organic synthesis IV, Acids, amino acids, and peptides, pp. 191-309, 1992, Maruzen Co., Ltd., in the presence of a condensing agent such as 1,3-dicyclohexylcarbodiimide (DCC), 1-ethyl-3-(3'-dimethylaminopropyl)carbodiimide hydrochloride (WSC.HCl or EDC HCl), O-(7-azabenzotriazol-1-yl)-N,N,N',N'-tetramethyluronium hexafluorophosphate (HATU), benzotriazol-1-yloxy tris(dimethylamino)-phosphonium hexafluorophosphate (BOP reagent), bis(2-oxo-3-oxazolidinyl)phosphinic chloride (BOP-Cl), or (benzotriazol-1-yloxy)tripyrrolidinophosphonium hexafluorophosphate (PyBOP) in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethyl-formamide, or an alcoholic solvent, e.g., methanol, ethanol, or 2-propanol, in the presence or absence of a base such as triethylamine or N,N-diisopropylethyl amine at a temperature in the range of 0° C. to the solvent reflux temperature.

The process as described above can generate a compound of formula (v-o) as a racemic mixture of cis 2,3,5-trisubstituted piperidines. A compound of formula (v-o) can be obtained as a single enantiomer using a chiral resolution process such as chiral preparatory HPLC or chiral supercritical fluid chromatography (SFC).

In specific cases in which group Y in compound (v-o) contains an amine, it may be necessary to deprotect the amine group using an acid such as trifluoroacetic acid or hydrochloric acid in order to obtain the final compound of the invention (Greene, T. W., et. al., "*Protective Groups in Organic Synthesis*", 2007, 4th Ed., Wiley, New York).

Example 1

4-((3'S,5'S,6'S)-4-Amino-1-((E)-3-(5-chloro-2-(1H-tetrazol-1-yl)phenyl)acryloyl)-5'-phenyl-[1,3'-bipiperidine]-6'-carboxamido)benzoic acid

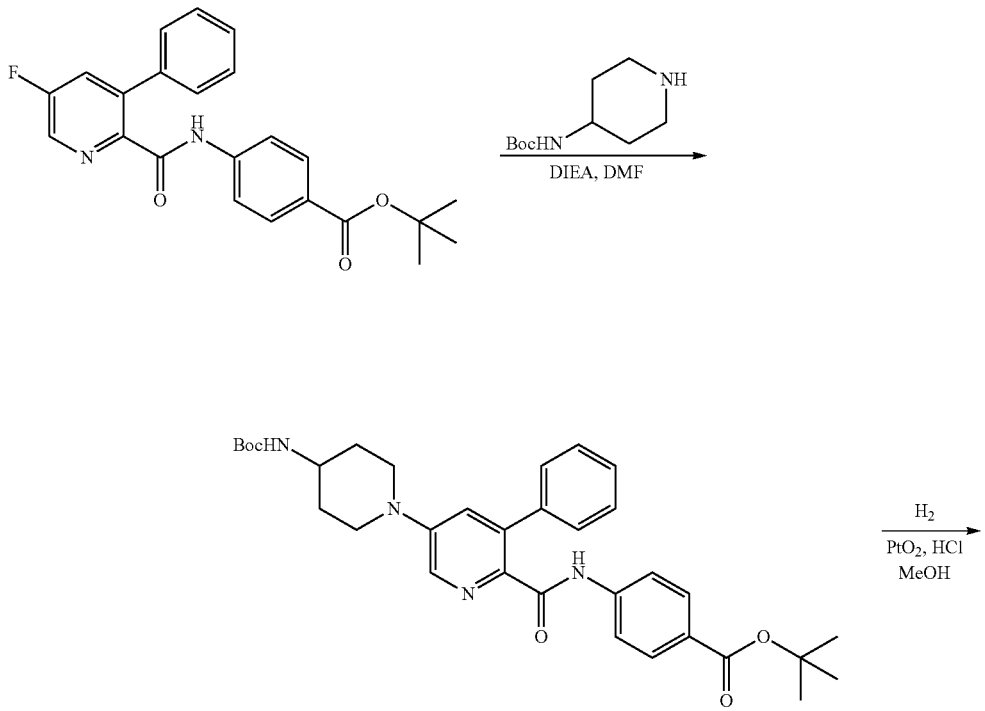

-continued
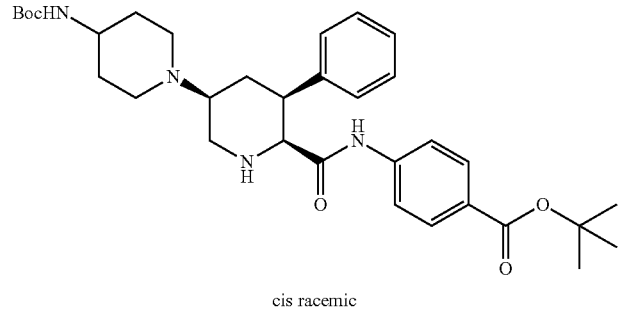 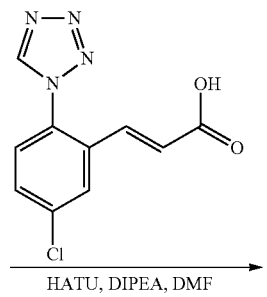
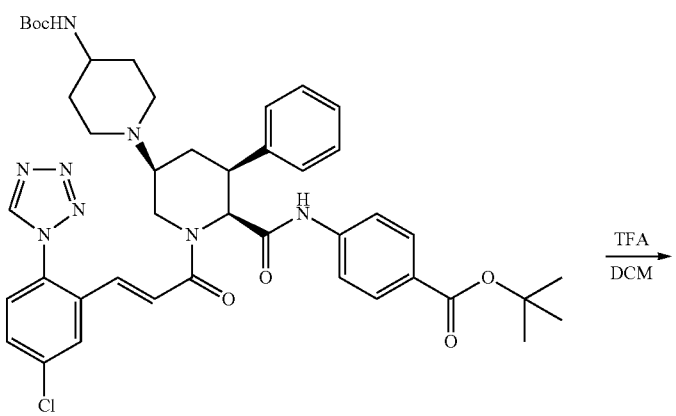
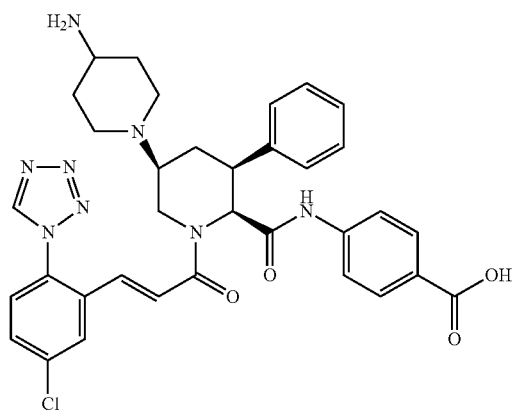
cis racemic
Example 1

Step 1: tert-Butyl 4-(5-(4-((tert-butoxycarbonyl)amino)piperidin-1-yl)-3-phenylpicolinamido)benzoate

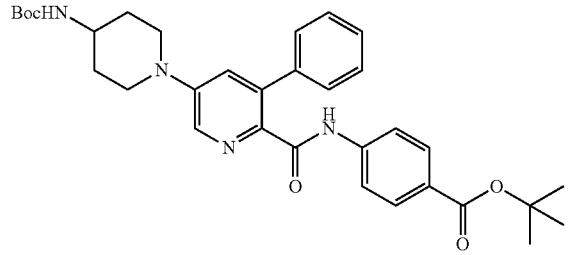 [SMILES: CC(C)(C)OC(=O)NC1CCN(c2cnc(C(=O)Nc3ccc(C(=O)OC(C)(C)C)cc3)c(-c3ccccc3)c2)CC1]

N,N-Diisopropylethylamine (0.623 ml, 3.57 mmol) was added to a mixture of tert-butyl piperidin-4-ylcarbamate (715 mg, 3.57 mmol) and tert-butyl 4-(5-fluoro-3-phenylpicolinamido)benzoate (700 mg, 1.78 mmol) in DMF 10 ml. The mixture was stirred at 150° C. in a microwave reactor for 2 hours. The mixture was cooled and diluted with ethyl acetate. The organic phase was washed with aqueous sodium hydrogen carbonate, filtered, and the solvent was evaporated under reduced pressure. The residue was purified by silica gel column chromatography (Biotage® 40M), eluting with ethyl acetate/isohexane to give tert-butyl 4-(5-(4-((tert-butoxycarbonyl)amino)piperidin-1-yl)-3-phenylpicolinamido)benzoate as 880 mg (86%) of a yellow solid. MS (ESI) m/z 573.61 (M+H).

Step 2: tert-Butyl 4-(-4-((tert-butoxycarbonyl)amino)-5'-phenyl-[1,3'-bipiperidine]-6'-carboxamido)benzoate

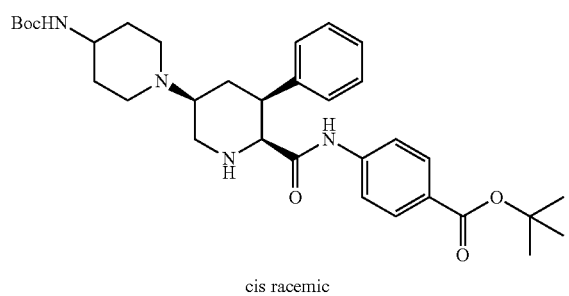 [SMILES: CC(C)(C)OC(=O)NC1CCN([C@@H]2CN[C@H](C(=O)Nc3ccc(C(=O)OC(C)(C)C)cc3)[C@H](c3ccccc3)C2)CC1]

cis racemic

Platinum(IV) oxide (13.5 mg, 0.059 mmol) was added to a stirred room temperature mixture of tert-butyl 4-(5-(4-((tert-butoxycarbonyl)amino)piperidin-1-yl)-3-phenylpicolinamido)benzoate (170 mg, 0.297 mmol) and methanol (15 ml). To this mixture was added 1 N aqueous HCl (0.6 mL). The reaction was degassed and then stirred under a hydrogen balloon at room temperature for 12 hours. The reaction mixture was filtered through a celite pad, and concentrated to dryness. The crude was used without further purification.

Step 3: tert-Butyl 4-(4-((tert-butoxycarbonyl)amino)-1'-((E)-3-(5-chloro-2-(1H-tetrazol-1-yl)phenyl)acryloyl)-5'-phenyl-[1,3'-bipiperidine]-6'-carboxamido)benzoate

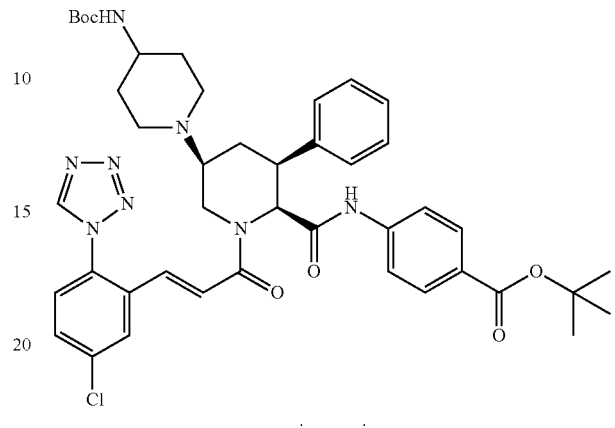

cis racemic

N,N-Diisopropylethylamine (0.06 ml, 0.352 mmol) was added to a stirred, room temperature mixture of HATU (134 mg, 0.352 mmol), tert-butyl 4-(-4-((tert-butoxycarbonyl)amino)-5'-phenyl-[1,3'-bipiperidine]-6'-carboxamido)benzoate (68 mg, 0.117 mmol), and (E)-3-(5-chloro-2-(1H-tetrazol-1-yl)phenyl)acrylic acid (57 mg, 0.228 mmol) in DMF (4 mL) and the mixture was stirred at room temperature for 4 hours. The mixture was cooled and diluted with ethyl acetate. The organic phase was washed with aqueous sodium bicarbonate, dried over MgSO$_4$, filtered and the solvent was evaporated under reduced pressure to give a yellow solid. The residue was purified by column chromatography on silica gel (Biotage® 25M) eluting with ethyl acetate/isohexane to give tert-butyl 4-(4-((tert-butoxycarbonyl)amino)-1'-((E)-3-(5-chloro-2-(1H-tetrazol-1-yl)phenyl)acryloyl)-5'-phenyl-[1,3'-bipiperidine]-6'-carboxamido)benzoate (MS (ESI) m/z 812.37 (M+H).

Step 4: 4-(4-Amino-1'-((E)-3-(5-chloro-2-(1H-tetrazol-1-yl)phenyl)acryloyl)-5'-phenyl-[1,3'-bipiperidine]-1-6'-carboxamido)benzoic acid (Example 1)

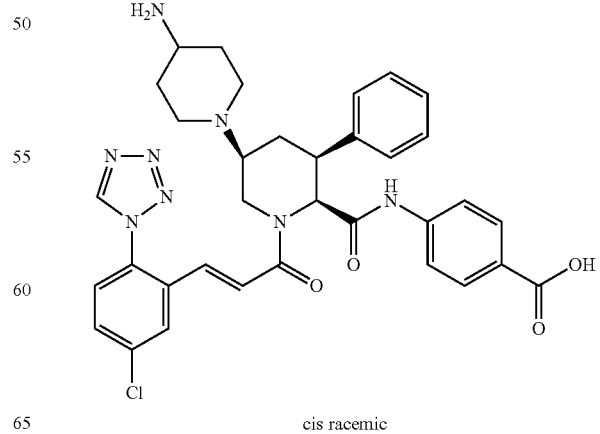

cis racemic

Trifluoroacetic acid (1 ml) was added to a stirred, room temperature mixture of tert-butyl 4-(4-((tert-butoxycarbonyl)amino)-1'-((E)-3-(5-chloro-2-(1H-tetrazol-1-yl)phenyl)acryloyl)-5'-phenyl-[1,3'-bipiperidine]-6'-carboxamido)benzoate 80 mg in DCM (2 ml) and the mixture was stirred at room temperature for 1 hr. The reaction mixture was concentrated and dissolved in MeOH and then purified by reverse phase Gilson HPLC (CH3CN/Water) to give 4-(1-((E)-3-(5-chloro-2-(1H-tetrazol-1-yl)phenyl)acryloyl)-3-cyclohexyl-5-(piperidin-4-yloxy)piperidine-2-carboxamido)benzoic acid as white solid. (MS (ESI) m/z 656.65 (M+H).

The following compounds may be prepared by someone skilled in the art following a procedure similar to the one described above. In cases where a chiral non-racemic compound is indicated, a chiral resolution by supercritical fluid chromatography may be performed on either the final product or late stage intermediates.

| Example | Structure | IUPAC Name | LCMS [M + H]+ |
|---|---|---|---|
| 2 | 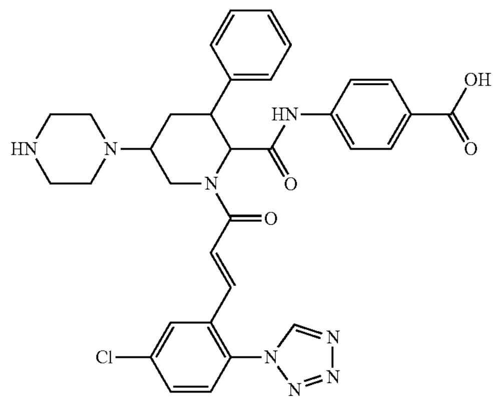 [SMILES: O=C(O)c1ccc(NC(=O)C2C(c3ccccc3)CC(N3CCNCC3)CN2C(=O)/C=C/c2cc(Cl)ccc2-n2cnnn2)cc1] | 4-{[(1-{(2E)-3-[5-chloro-2-(1H-tetrazol-1-yl)phenyl]prop-2-enoyl}-3-phenyl-5-piperazin-1-ylpiperidin-2-yl)carbonyl]amino}benzoic acid | 641.41 |
| 3 | 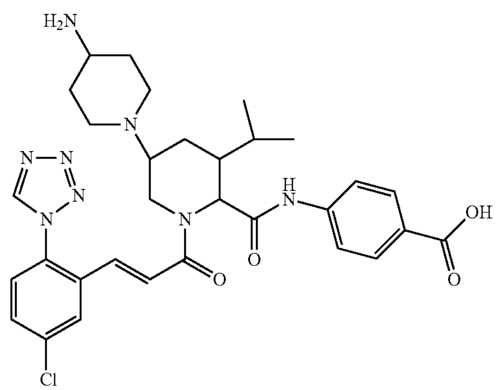 [SMILES: CC(C)C1CC(N2CCC(N)CC2)CN(C(=O)/C=C/c2cc(Cl)ccc2-n2cnnn2)C1C(=O)Nc1ccc(C(=O)O)cc1] | 4-({[4-amino-1'-{(2E)-3-[5-chloro-2-(1H-tetrazol-1-yl)phenyl]prop-2-enoyl}-5'-(1-methylethyl)-1,3'-bipiperidin-6'-yl]carbonyl}amino)benzoic acid | 621.54 |
| 4 | 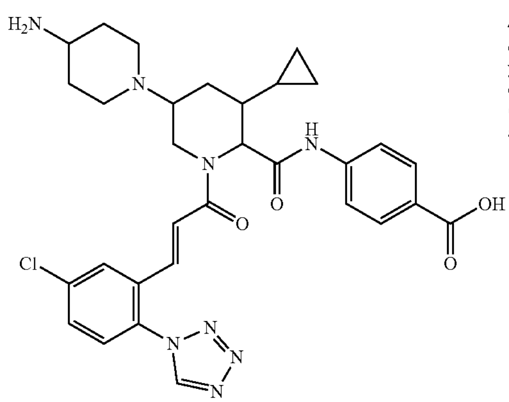 | 4-{[(4-amino-1'-{(2E)-3-[5-chloro-2-(1H-tetrazol-1-yl)phenyl]prop-2-enoyl}-5'-cyclopropyl-1,3'-bipiperidin-6'-yl)carbonyl]amino}benzoic acid | 619.66 |

| Example | Structure | IUPAC Name | LCMS [M + H]+ |
|---|---|---|---|
| 5 | 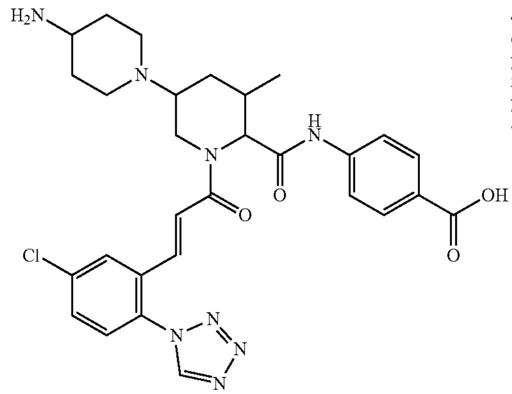 | 4-{[(4-amino-1'-{(2E)-3-[5-chloro-2-(1H-tetrazol-1-yl)phenyl]prop-2-enoyl}-5'-methyl-1,3'-bipiperidin-6'-yl)carbonyl]amino}benzoic acid | 593.58 |
| 6 | 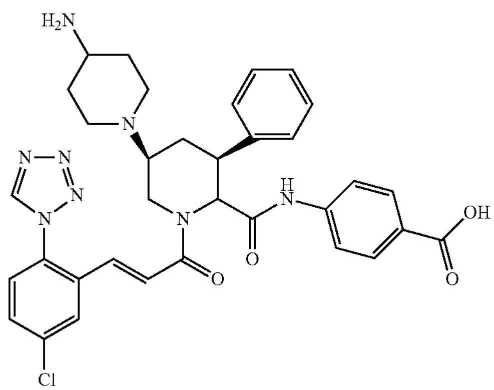 [SMILES: NC1CCN([C@H]2C[C@@H](c3ccccc3)C(C(=O)Nc3ccc(C(=O)O)cc3)N(C(=O)/C=C/c3cc(Cl)ccc3-n3cnnn3)C2)CC1] | 4-({[(3'S,5'S,6'S)-4-amino-1'-{(2E)-3-[5-chloro-2-(1H-tetrazol-1-yl)phenyl]prop-2-enoyl}-5'-phenyl-1,3'-bipiperidin-6'-yl]carbonyl}amino)benzoic acid | 655.42 |
| 7 | 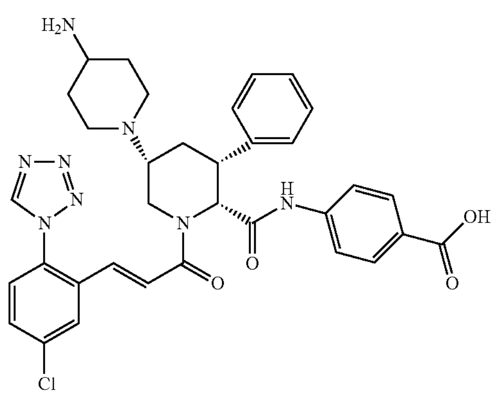 [SMILES: NC1CCN([C@@H]2C[C@H](c3ccccc3)[C@H](C(=O)Nc3ccc(C(=O)O)cc3)N(C(=O)/C=C/c3cc(Cl)ccc3-n3cnnn3)C2)CC1] | 4-({[(3'R,5'R,6'R)-4-amino-1'-{(2E)-3-[5-chloro-2-(1H-tetrazol-1-yl)phenyl]prop-2-enoyl}-5'-phenyl-1,3'-bipiperidin-6'-yl]carbonyl}amino)benzoic acid | 655.42 |

Examples 8-10

4-(4-((E)-3-(5-chloro-2-(1H-tetrazol-1-yl)phenyl)acrylamido)-1'-((E)-3-(5-chloro-2-(1H-tetrazol-1-yl)phenyl)acryloyl)-5'-phenyl-[1,3-bipiperidine]-6'-carboxamido)benzoic acid (Example 8)

4-((2S,3S,5S)-1-((E)-3-(5-chloro-2-(1H-tetrazol-1-yl)phenyl)acryloyl)-3-phenyl-5-(piperidin-4-yloxy)piperidine-2-carboxamido)benzoic acid (Example 9)

4-((2R,3R,5R)-1-((E)-3-(5-chloro-2-(1H-tetrazol-1-yl)phenyl)acryloyl)-3-phenyl-5-(piperidin-4-yloxy)piperidine-2-carboxamido)benzoic acid (Example 10)

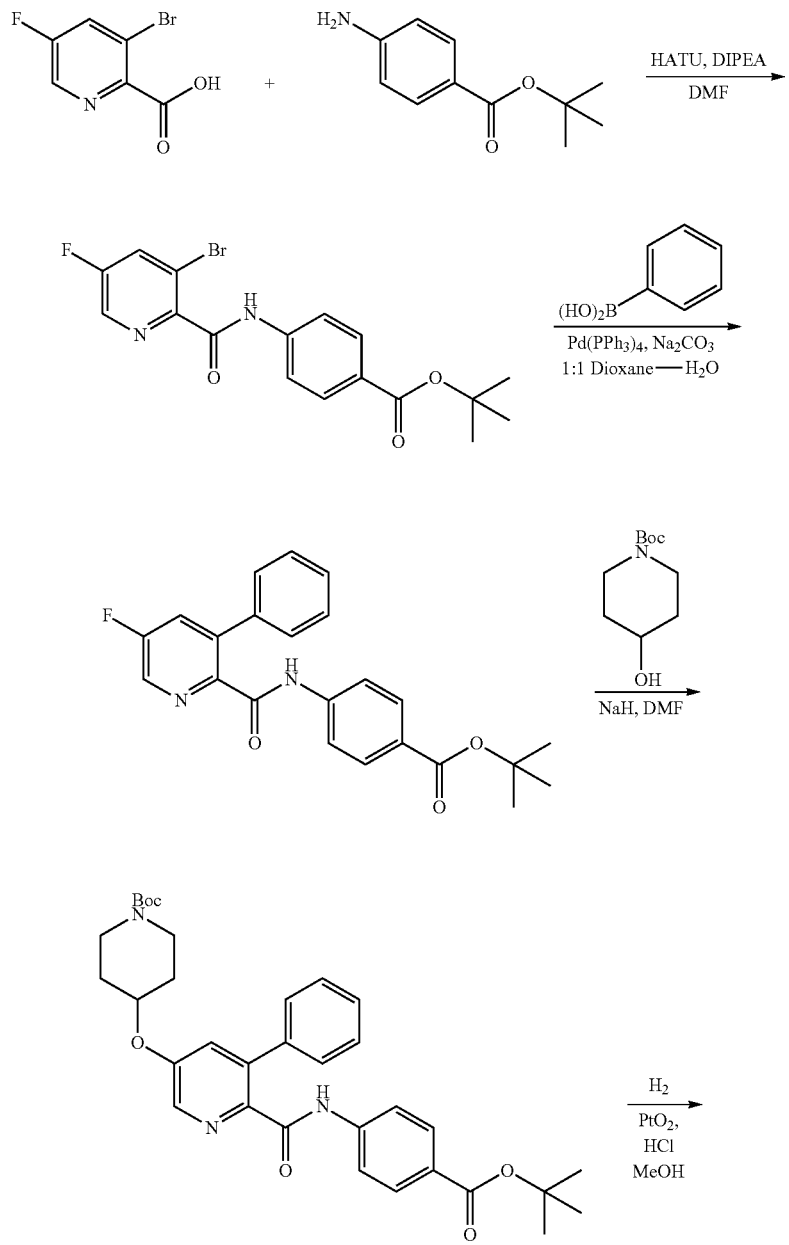

-continued
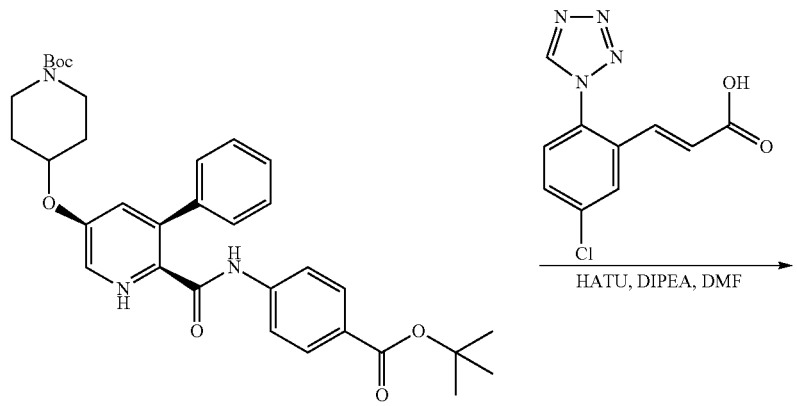
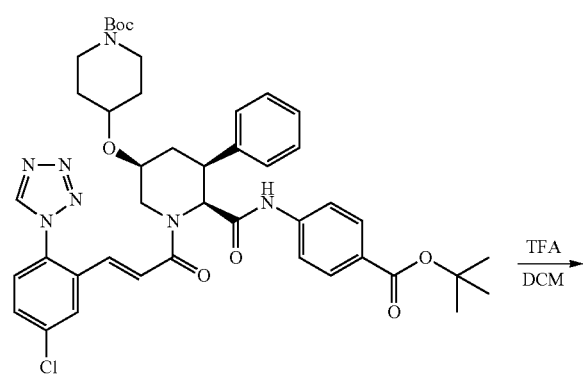
cis racemic
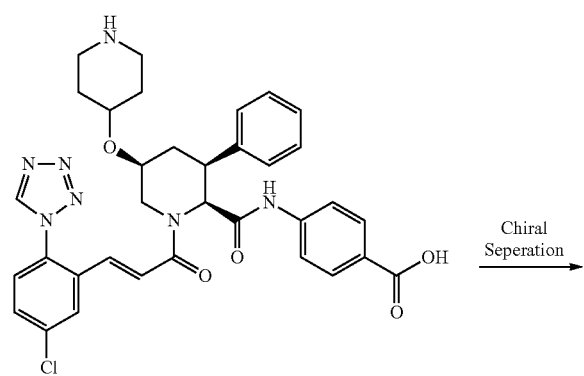
cis racemic
Example 8
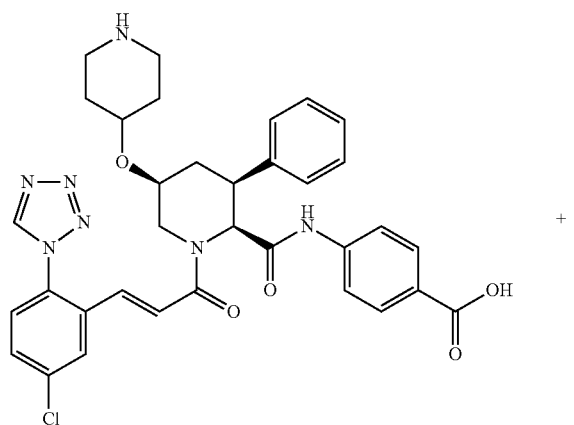
Example 9

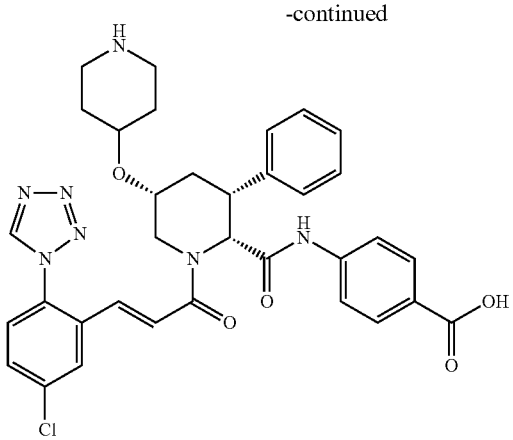

Example 10

Step 1: tert-Butyl 4-(3-bromo-5-fluoropicolinamido)benzoate

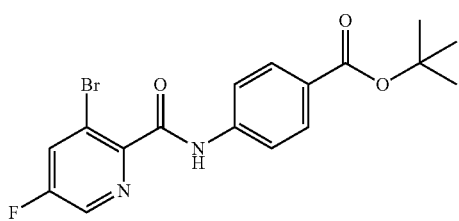 [SMILES: CC(C)(C)OC(=O)c1ccc(NC(=O)c2ncc(F)cc2Br)cc1]

N,N-Diisopropylethylamine (11.07 ml, 63.4 mmol) was added to a stirred room temperature mixture of HATU (16 g, 42.3 mmol), tert-butyl-4-aminobenzoate 6.13 g (31.7 mmol), and 3-bromo-5-fluropicolinic acid (4.65 g, 21.14 mmol) in DMF 30 ml. The mixture was stirred at room temperature overnight. The mixture was cooled and diluted with ethyl acetate. The organic phase was washed with aqueous sodium hydrogen carbonate, filtered, and the solvent was evaporated under reduced pressure. The residue was purified by silica gel column chromatography (Biotage® 40M), eluting with ethyl acetate/isohexane to give tert-butyl 4-(3-bromo-5-fluoropicolinamido)benzoate as a yellow solid. MS (ESI) m/z 397.26 (M+H).

Step 2: tert-Butyl 4-(5-fluoro-3-phenylpicolinamido)benzoate

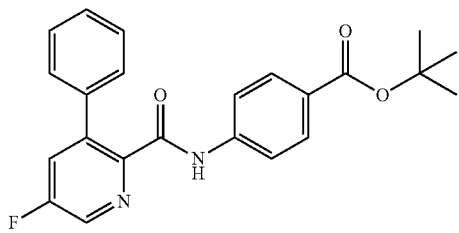 [SMILES: CC(C)(C)OC(=O)c1ccc(NC(=O)c2ncc(F)cc2-c2ccccc2)cc1]

A mixture of sodium carbonate (805 mg, 7.59 mmol), tetrakis-(triphenylphosphine)palladium(0) (585 mg, 0.506 mmol), phenyl boronic acid (617 mg, 5.06 mmol), and tert-butyl 4-(3-bromopicolinamido)benzoate (1 g, 2.53 mmol) in 3:1 dioxane-water (7 ml) was heated at 120° C. for 1 hour in a microwave reactor. The mixture was cooled, diluted with ethyl acetate and then washed with aqueous sodium hydrogen carbonate. The organic phase was dried over MgSO$_4$, filtered and the solvent was evaporated under reduced pressure. The residue was purified by column chromatography on silica gel (Biotage® 25M), eluting with ethyl acetate/isohexane to give tert-butyl 4-(5-fluoro-3-phenylpicolinamido)benzoate. MS (ESI) m/z 393.41 (M+H).

Step 3: tert-butyl 4-((6-((4-(tert-butoxycarbonyl)phenyl)carbamoyl)-5-phenylpyridin-3-yl)oxy)piperidine-1-carboxylate

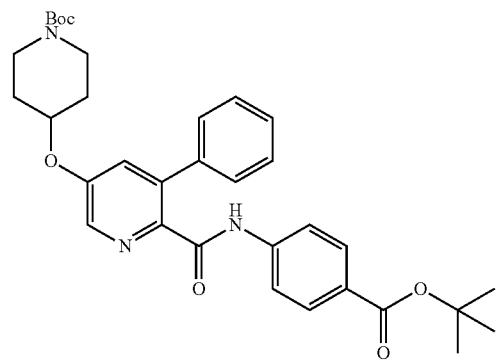 [SMILES: CC(C)(C)OC(=O)c1ccc(NC(=O)c2ncc(OC3CCN(C(=O)OC(C)(C)C)CC3)cc2-c2ccccc2)cc1]

NaH (173 mg, 4.32 mmol) was added to a stirred mixture of tert-butyl 4-hydroxypiperidine-1-carboxylate (725 mg, 3.60 mmol) in THF and the mixture was stirred at room temperature for 10 min. To this mixture was then added tert-butyl 4-(5-fluoro-3-phenylpicolinamido)benzoate (942 mg, 2.4 mmol) in THF at rt. The reaction was stirred at 80° C. for overnight. The mixture was cooled, aqueous sodium hydroxide was added and the mixture was extracted with ethyl acetate. The combined organic fractions were washed with brine, dried with MgSO$_4$, filtered and the solvent was evaporated under reduced pressure. The residue was purified by column chromatography on silica gel Biotage® 40M, eluting with EtOAc/isohexane to give tert-butyl 4-((6-((4-

(tert-butoxy-carbonyl)phenyl)carbamoyl)-5-phenylpyridin-3-yl)oxy)piperidine-1-carboxylate. MS (ESI) m/z 574.63 (M+H).

Step 4: tert-butyl 4-((6-((4-(tert-butoxycarbonyl)phenyl)carbamoyl)-5-phenylpiperidin-3-yl)oxy)piperidine-1-carboxylate and tert-butyl 4-((6-((4-(tert-butoxycarbonyl)phenyl)carbamoyl)-5-cyclohexylpiperidin-3-yl)oxy)piperidine-1-carboxylate

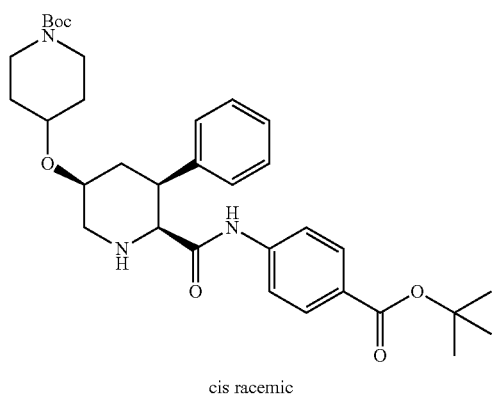

cis racemic

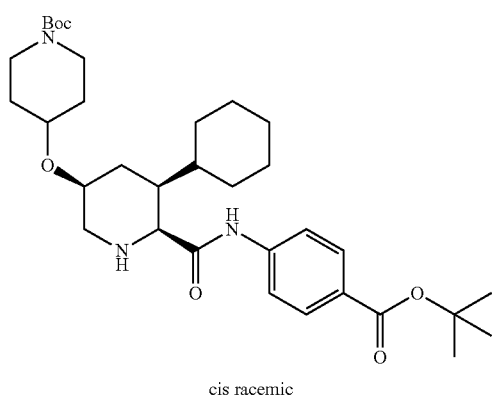

cis racemic

Platinum(IV) oxide (20 mg, 0.088 mmol) was added to a stirred room temperature mixture of 4-((6-((4-(tert-butoxycarbonyl)phenyl)carbamoyl)-5-phenylpyridin-3-yl)oxy)piperidine-1-carboxylate (380 mg, 0.662 mmol) and methanol (10 ml). To this mixture was added 3 N aqueous HCl (1.987 mL). The reaction was degassed and then stirred under a hydrogen balloon at room temperature for 12 hours. The reaction mixture was filtered through a celite pad, and aqueous sodium hydrogen carbonate was added. The mixture was cooled, diluted with ethyl acetate and washed with aqueous sodium hydrogen carbonate. The organic phase was dried over MgSO₄, and the solvent was evaporated under reduced pressure. The residue was purified by reverse phase Gilson HPLC (CH₃CN/Water) to yield tert-butyl 4-((6-((4-(tert-butoxycarbonyl)phenyl)carbamoyl)-5-phenylpiperidin-3-yl)oxy)piperidine-1-carboxylate, MS (ESI) m/z 580.69 (M+H), and 14 mg (3.6%) of tert-butyl 4-((6-((4-(tert-butoxycarbonyl)phenyl)carbamoyl)-5-cyclohexylpiperidin-3-yl)oxy)piperidine-1-carboxylate, MS (ESI) m/z 586.75 (M+H).

Step 5: tert-butyl 4-((6-((4-(tert-butoxycarbonyl)phenyl)carbamoyl)-1-((E)-3-(5-chloro-2-(1H-tetrazol-1-yl)phenyl)acryloyl)-5-phenylpiperidin-3-yl)oxy)piperidine-1-carboxylate

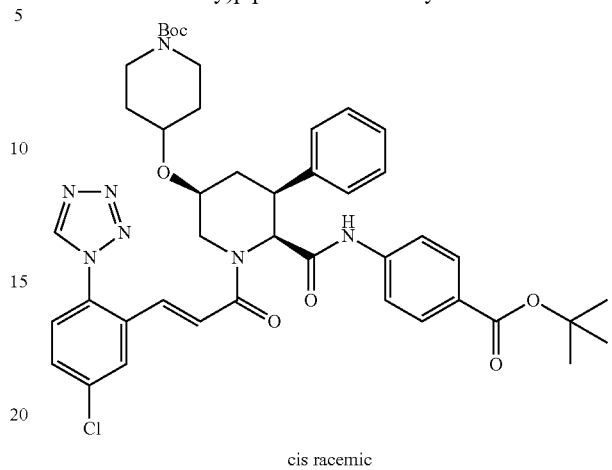

cis racemic

N,N-Diisopropylethylamine (0.06 ml, 0.342 mmol) was added to a stirred, room temperature mixture of HATU (87 mg, 0.228 mmol), tert-butyl 4-((6-((4-(tert-butoxycarbonyl)phenyl)carbamoyl)-5-phenylpiperidin-3-yl)oxy)piperidine-1-carboxylate (66 mg, 0.114 mmol), and (E)-3-(5-chloro-2-(1H-tetrazol-1-yl)phenyl)acrylic acid (57 mg, 0.228 mmol) in DMF (4 mL) and the mixture was stirred at room temperature for 4 hours. The mixture was cooled and diluted with ethyl acetate. The organic phase was washed with aqueous sodium bicarbonate, dried over MgSO₄, filtered and the solvent was evaporated under reduced pressure to give a yellow solid. The residue was purified by column chromatography on silica gel (Biotage® 25M) eluting with ethyl acetate/isohexane to give 83 mg (90%) of tert-butyl 4-((6-((4-(tert-butoxycarbonyl)phenyl)carbamoyl)-1-((E)-3-(5-chloro-2-(1H-tetrazol-1-yl)phenyl)acryloyl)-5-phenylpiperidin-3-yl)oxy)piperidine-1-carboxylate (MS (ESI) m/z 812.80 (M+H).

Step 6: 4-(1-((E)-3-(5-Chloro-2-(1H-tetrazol-1-yl)phenyl)acryloyl)-3-phenyl-5-(piperidin-4-yloxy)piperidine-2-carboxamido)benzoic acid (Example 8)

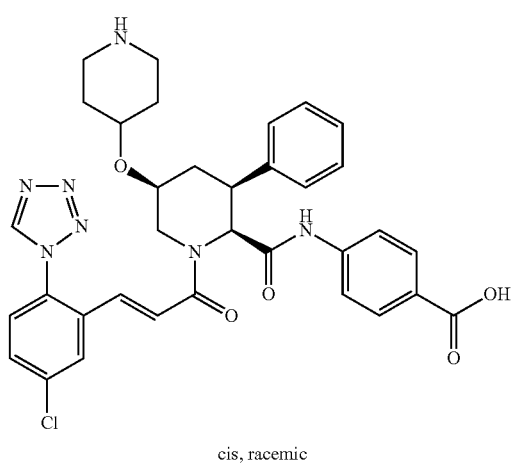 [SMILES: O=C(O)c1ccc(NC(=O)[C@@H]2[C@H](c3ccccc3)C[C@H](OC3CCNCC3)CN2C(=O)/C=C/c2cc(Cl)ccc2-n2cnnn2)cc1]

cis, racemic

Trifluoroacetic acid (1 ml) was added to a stirred, room temperature mixture of tert-butyl 4-((6-((4-(tert-butoxycarbonyl)phenyl)carbamoyl)-1-((E)-3-(5-chloro-2-(1H-tetrazol-1-yl)phenyl)acryloyl)-5-phenylpiperidin-3-yl)oxy)piperidine-1-carboxylate in DCM (2 ml) and the mixture was stirred at room temperature for 1 hr. The reaction mixture was concentrated and dissolved in MeOH and then purified by reverse phase Gilson HPLC (CH$_3$CN/Water) to give 4-(1-((E)-3-(5-chloro-2-(1H-tetrazol-1-yl)phenyl)acryloyl)-3-phenyl-5-(piperidin-4-yloxy)piperidine-2-carboxamido) benzoic acid as a white solid. $^1$H NMR (500 MHz, CD$_3$OD) δ 9.44 (s, 1H), 8.03 (s, 1H), 7.74 (s, 1H), 7.72 (s, 1H), 7.55 (dd, J=2.0, 8.5 Hz, 1H), 7.47 (d, J=8.5 Hz, 1H), 7.27-7.05 (m, 9H), 5.17 (d, J=6.0 Hz, 1H), 4.11 (d, J=7.5 Hz, 1H), 3.94 (br, 1H), 3.73-3.65 (m, 2H), 3.34-3.01 (m, 6H), 2.46 (m, 1H), 2.06-1.77 (m, 5H). (MS (ESI) m/z 656.63 (M+H).

Step 7: 4-((2S,3S,5S)-1-((E)-3-(5-chloro-2-(1H-tetrazol-1-yl)phenyl)acryloyl)-3-phenyl-5-(piperidin-4-yloxy)piperidine-2-carboxamido)benzoic acid (Example 9)

4-((2R,3R,5R)-1-((E)-3-(5-chloro-2-(1H-tetrazol-1-yl)phenyl)acryloyl)-3-phenyl-5-(piperidin-4-yloxy) piperidine-2-carboxamido)benzoic acid (Example 10)

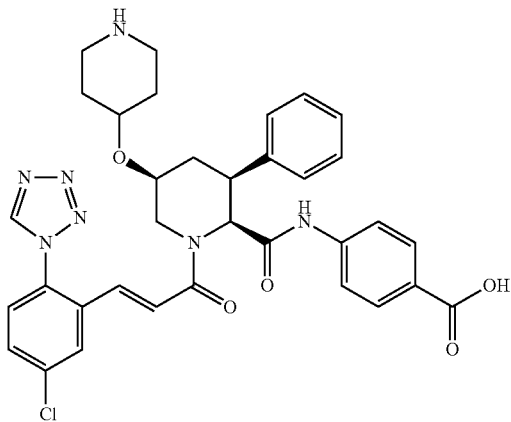 [SMILES: O=C(O)c1ccc(NC(=O)[C@@H]2[C@H](c3ccccc3)C[C@H](OC3CCNCC3)CN2C(=O)/C=C/c2cc(Cl)ccc2-n2cnnn2)cc1]

From this product 10 mg was subjected to chiral separation using Reverse phase HPLC (20×250 mm, Lux Cellulose-4, A: 0.1% TFA in water, B: MeCN; Gradient: 75/25 to 45/55 A/B in 12 minutes; run time 13.5 minute, Flow rate: 15 ml/min) to afford 4-((2S,3S,5S)-1-((E)-3-(5-chloro-2-(1H-tetrazol-1-yl)phenyl)acryloyl)-3-phenyl-5-(piperidin-4-yloxy)piperidine-2-carboxamido)benzoic acid (peak 2, Example 9) (MS (ESI) m/z 656.37 (M+H)) and 4-((2R,3R,5R)-1-((E)-3-(5-chloro-2-(1H-tetrazol-1-yl)phenyl)acryloyl)-3-phenyl-5-(piperidin-4-yloxy)piperidine-2-carboxamido)benzoic acid (peak 1, Example 10). MS (ESI) m/z 656.37 (M+H).

Example 11

4-(1-((E)-3-(5-Chloro-2-(1H-tetrazol-1-yl)phenyl) acryloyl-3-cyclohexyl-5-(piperidin-4-yloxy)piperidine-2-carboxamido)benzoic acid

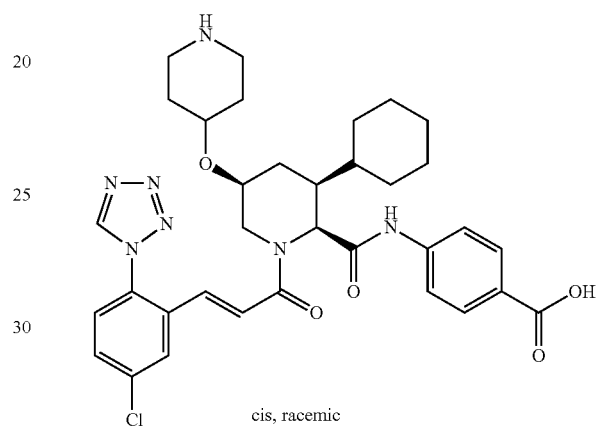

cis, racemic

This compound is synthesized in a similar way to 4-(1-((E)-3-(5-chloro-2-(1H-tetrazol-1-yl)phenyl)acryloyl)-3-phenyl-5-(piperidin-4-yloxy)piperidine-2-carboxamido) benzoic acid. (MS (ESI) m/z 662.60 (M+H)).

Example 12

4-(1-((E)-3-(5-chloro-2-(1H-tetrazol-1-yl)phenyl) acryloyl)-5-phenyl-3-(piperidin-4-yloxy)piperidine-2-carboxamido)benzoic acid

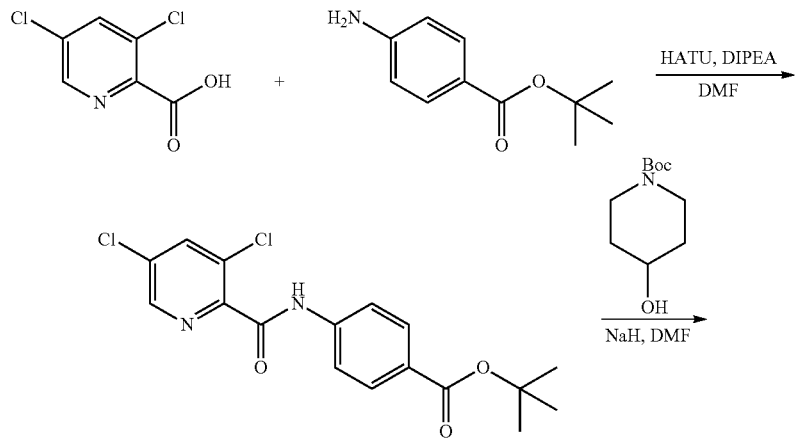

-continued
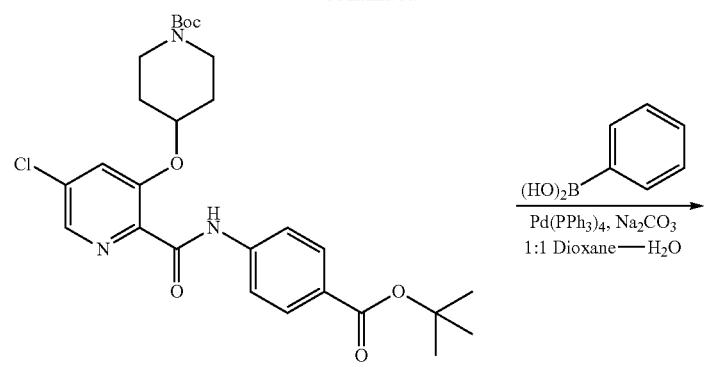
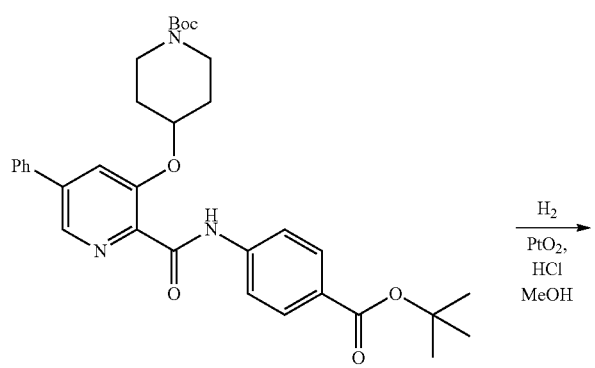
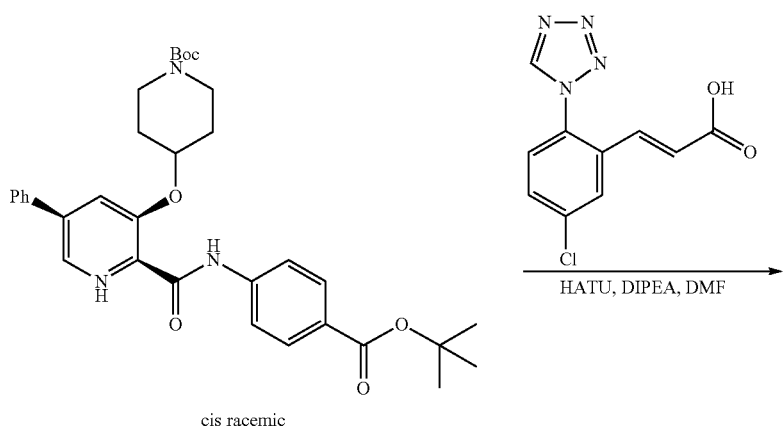
cis racemic
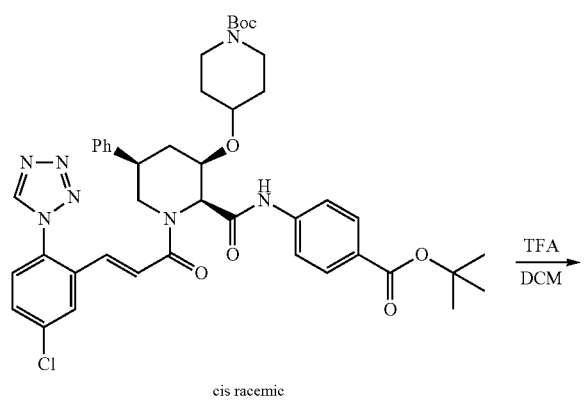
cis racemic

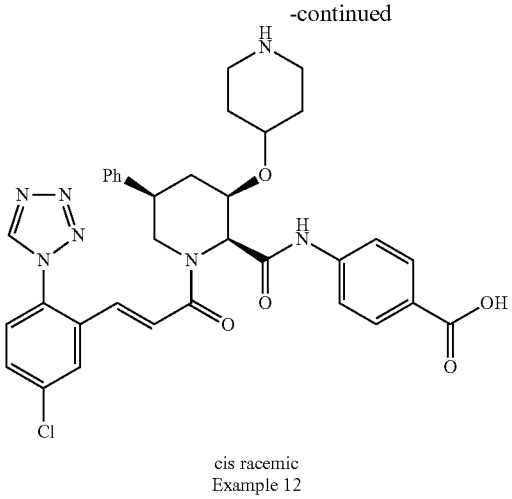

cis racemic
Example 12

Step 1: tert-Butyl 4-(3,5-dichloropicolinamido)benzoate

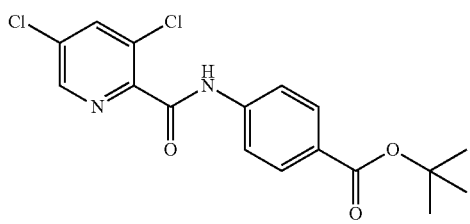 [SMILES: CC(C)(C)OC(=O)c1ccc(NC(=O)c2ncc(Cl)cc2Cl)cc1]

N,N-Diisopropylethylamine (5.46 ml, 31.3 mmol) was added to a stirred room temperature mixture of HATU (7.9 g, 20.8 mmol), tert-butyl-4-aminobenzoate 2.4 g (12.5 mmol), and 3,5-dichloropicolinic acid (2 g, 10.4 mmol) in DMF 30 ml. The mixture was stirred at room temperature overnight. The mixture was cooled and diluted with ethyl acetate. The organic phase was washed with aqueous sodium hydrogen carbonate, filtered, and the solvent was evaporated under reduced pressure. The residue was purified by silica gel column chromatography (Biotage® 40M), eluting with ethyl acetate/isohexane to give tert-butyl 4-(3,5-dichloropicolinamido)benzoate a yellow solid. MS (ESI) m/z 367.19 (M+H).

Step 2: tert-butyl 4-((2-((4-(tert-butoxycarbonyl)phenyl)carbamoyl)-5-chloropyridin-3-yl)oxy)piperidine-1-carboxylate

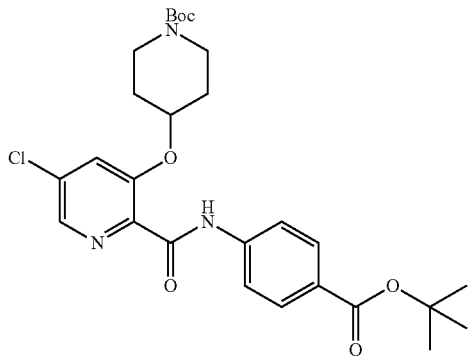 [SMILES: CC(C)(C)OC(=O)c1ccc(NC(=O)c2ncc(Cl)cc2OC2CCN(C(=O)OC(C)(C)C)CC2)cc1]

NaH (196 mg, 8.17 mmol) was added to a stirred mixture of tert-butyl 4-hydroxypiperidine-1-carboxylate (1.206 g, 5.99 mmol) in THF (40 ml) and the mixture was stirred at room temperature for 10 min. To this mixture was then added tert-butyl 4-(3,5-dichloropicolinamido)benzoate (2 g, 5.45 mmol) in THF at rt. The reaction was stirred at 80° C. for overnight. The mixture was cooled, aqueous sodium hydroxide was added and the mixture was extracted with ethyl acetate. The combined organic fractions were washed with brine, dried with MgSO₄, filtered and the solvent was evaporated under reduced pressure. The residue was purified by column chromatography on silica gel Biotage® 40M, eluting with EtOAc/isohexane to give tert-butyl 4-((2-((4-(tert-butoxycarbonyl)phenyl)carbamoyl)-5-chloropyridin-3-yl)oxy)piperidine-1-carboxylate. (MS (ESI) m/z 532.47 (M+H).

Step 3: tert-butyl 4-((2-((4-(tert-butoxycarbonyl)phenyl)carbamoyl)-5-phenylpyridin-3-yl)oxy) piperidine-1-carboxylate

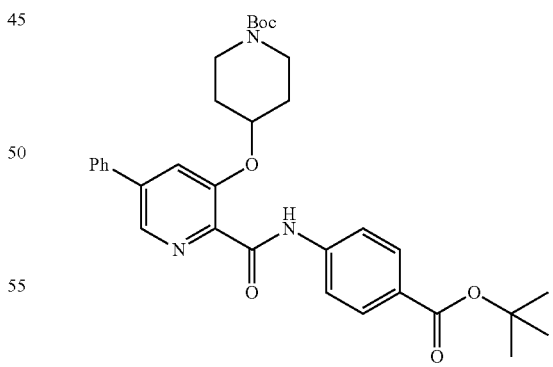

A mixture of sodium carbonate (269 mg, 2.54 mmol), tetrakis(triphenylphosphine)palladium(0) (585 mg, 0.506 mmol), phenyl boronic acid (195 mg, 0.169 mmol), and tert-butyl 4-((2-((4-(tert-butoxycarbonyl)phenyl)carbamoyl)-5-chloropyridin-3-yl)oxy)piperidine-1-carboxylate (450 mg, 0.846 mmol) in 3:1 dioxane-water (7 ml) was heated at 120° C. for 1 hour in a microwave reactor. The mixture was cooled, diluted with ethyl acetate and then washed with aqueous sodium hydrogen carbonate. The organic phase was dried over MgSO$_4$, filtered and the solvent was evaporated under reduced pressure. The residue was purified by column chromatography on silica gel (Biotage® 25M), eluting with ethyl acetate/isohexane to give tert-butyl 4-((2-((4-(tert-butoxycarbonyl)phenyl)carbamoyl)-5-phenylpyridin-3-yl)oxy)piperidine-1-carboxylate. (MS (ESI) m/z 574.55 (M+H).

Step 4: tert-butyl 4-((2-((4-(tert-butoxycarbonyl)phenyl)carbamoyl)-5-phenylpiperidin-3-yl)oxy)piperidine-1-carboxylate

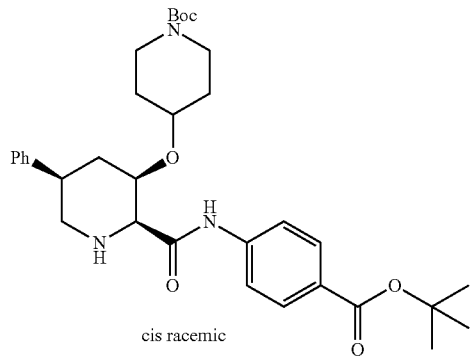 [SMILES: CC(C)(C)OC(=O)c1ccc(NC(=O)[C@H]2NC[C@@H](c3ccccc3)C[C@H]2OC2CCN(C(=O)OC(C)(C)C)CC2)cc1]

Platinum(IV) oxide (40 mg, 0.176 mmol) was added to a stirred room temperature mixture of tert-butyl 4-((2-((4-(tert-butoxycarbonyl)phenyl)carbamoyl)-5-phenylpyridin-3-yl)oxy)piperidine-1-carboxylate (180 mg, 0.314 mmol) and methanol (10 ml). To this mixture was added 1 N aqueous HCl (3 mL). The reaction was degassed and then stirred under a hydrogen balloon at room temperature for 12 hours. The reaction mixture was filtered through a celite pad, and aqueous sodium hydrogen carbonate was added. The mixture was cooled, diluted with ethyl acetate and washed with aqueous sodium hydrogen carbonate. The organic phase was dried over MgSO$_4$, filtered and the solvent was evaporated under reduced pressure. The residue was purified by reverse phase Gilson HPLC (CH3CN/Water) to yield tert-butyl 4-((2-((4-(tert-butoxycarbonyl)phenyl)carbamoyl)-5-phenylpiperidin-3-yl)oxy) piperidine-1-carboxylate, MS (ESI) m/z 580.59 (M+H).

Step 5: tert-butyl 4-((2-((4-(tert-butoxycarbonyl)phenyl)carbamoyl)-1-((E)-3-(5-chloro-2-(1H-tetrazol-1-yl)phenyl)acryloyl)-5-phenylpiperidin-3-yl)oxy)piperidine-1-carboxylate

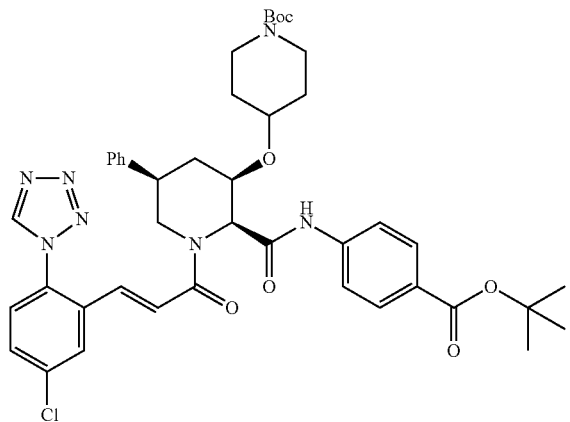 [SMILES: CC(C)(C)OC(=O)c1ccc(NC(=O)[C@@H]2[C@H](OC3CCN(C(=O)OC(C)(C)C)CC3)C[C@H](c3ccccc3)CN2C(=O)/C=C/c2cc(Cl)ccc2-n2cnnn2)cc1]

N,N-Diisopropylethylamine (0.02 ml, 0.103 mmol) was added to a stirred, room temperature mixture of HATU (30 mg, 0.078 mmol), tert-butyl 4-((2-((4-(tert-butoxycarbonyl)phenyl)carbamoyl)-5-phenylpiperidin-3-yl)oxy) piperidine-1-carboxylate (15 mg, 0.026 mmol), and (E)-3-(5-chloro-2-(1H-tetrazol-1-yl)phenyl)acrylic acid (20 mg, 0.78 mmol) in DMF (4 mL) and the mixture was stirred at room temperature for 4 hours. The mixture was cooled and diluted with ethyl acetate. The organic phase was washed with aqueous sodium bicarbonate, dried over MgSO$_4$, filtered and the solvent was evaporated under reduced pressure to give a yellow solid. The residue was purified by column chromatography on silica gel (Biotage® 12M) eluting with ethyl acetate/isohexane to give tert-butyl 4-((2-((4-(tert-butoxycarbonyl)phenyl)carbamoyl)-1-((E)-3-(5-chloro-2-(1H-tetrazol-1-yl)phenyl)acryloyl)-5-phenylpiperidin-3-yl)oxy)piperidine-1-carboxylate (MS (ESI) m/z 812.86 (M+H).

Step 6: 4-(1-((E)-3-(5-chloro-2-(1H-tetrazol-1-yl)phenyl)acryloyl)-5-phenyl-3-(piperidin-4-yloxy)piperidine-2-carboxamido)benzoic acid

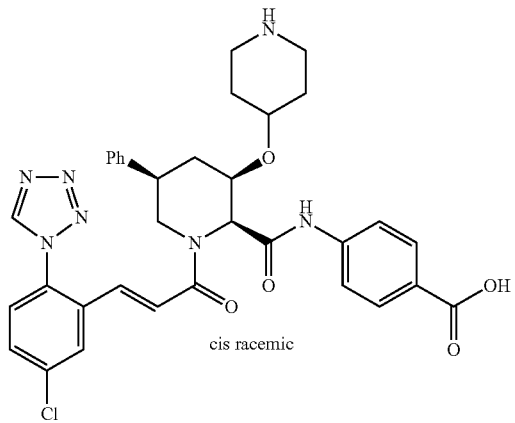 [SMILES: O=C(O)c1ccc(NC(=O)[C@@H]2[C@H](OC3CCNCC3)C[C@H](c3ccccc3)CN2C(=O)/C=C/c2cc(Cl)ccc2-n2cnnn2)cc1]

Trifluoroacetic acid (0.5 ml) was added to a stirred, room temperature mixture of tert-butyl 4-((2-((4-(tert-butoxycarbonyl)phenyl)carbamoyl)-1-((E)-3-(5-chloro-2-(1H-tetrazol-1-yl)phenyl)acryloyl)-5-phenylpiperidin-3-yl)oxy)piperidine-1-carboxylate in DCM (1 ml) and the mixture was stirred at room temperature for 1 hr. The reaction mixture was concentrated and dissolved in MeOH and then purified by reverse phase Gilson HPLC (CH$_3$CN/Water) to give 4-(1-((E)-3-(5-chloro-2-(1H-tetrazol-1-yl)phenyl)acryloyl)-5-phenyl-3-(piperidin-4-yloxy)piperidine-2-carboxamido)benzoic acid as a white solid. (MS (ESI) m/z 656.61 (M+H).

Example 13
Methyl (4-{2-[4-amino-1'-{(2E)-3-[5-chloro-2-(1H-tetrazol-1-yl)phenyl]prop-2-enoyl}-5'-(4-fluorophenyl)-1,3'-bipiperidin-6'-yl]-1H-imidazol-4-yl}phenyl)-carbamate
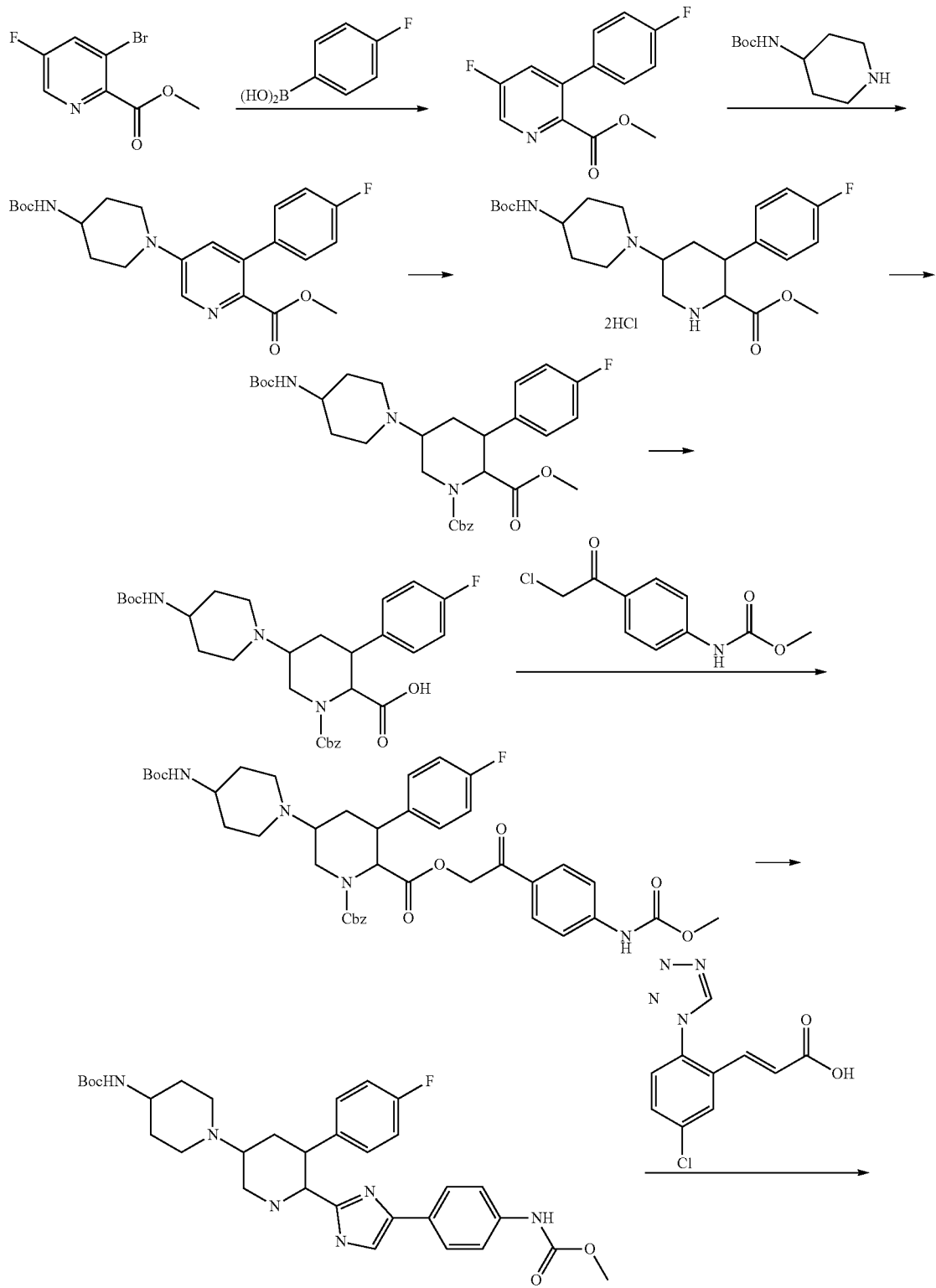

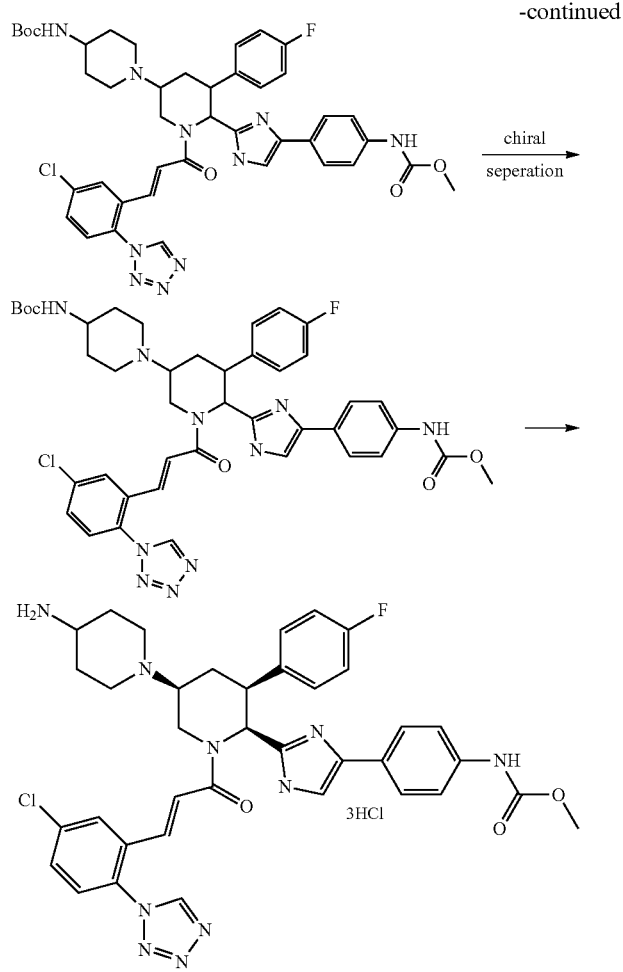

Example 13

Step 1: Methyl 3-bromo-5-fluoropicolinate

3-Bromo-5-fluoropicolinic acid (6.05 g, 27.5 mmol) and potassium carbonate (11.4 g, 83.0 mmol) were mixed in DMF and stirred at room temperature for 30 min. Iodomethane (2.57 mL, 41.3 mmol) was then added. The mixture was stirred at room temperature for 1 h. The mixture was diluted with ethyl acetate, washed with water (2×), brine, dried (MgSO$_4$), filtered and the solvent was evaporated under reduced pressure. The residue was purified by column chromatography on silica gel RediSep® 120 g, eluting with EtOAc/isohexane (0-70%) to give the title compound as a colorless oil. MS (ESI) m/z 236.05 (M+H).

Step 2: Methyl 5-fluoro-3-(4-fluorophenyl)picolinate

A 20 mL of microwave vial was charged with methyl 3-bromo-5-fluoropicolinate (2.00 g, 8.55 mmol), (4-fluorophenyl)boronic acid (2.39 g, 17.09 mmol), sodium carbonate (2.72 g, 25.6 mmol) and tetrakis (triphenylphosphine)palladium(0) (0.50 g, 0.427 mmol). Then dioxane/water (8 mL/2 mL) was added. The reaction mixture was treated under microwave at 130° C. for 30 min. The mixture was concentrated under reduced pressure. The residue was dissolved in EtOAc, washed with sat. sodium bicarbonate, and brine, dried (MgSO$_4$), filtered and concentrated. The residue was dissolved in DCM, filtered off the precipitate, which was the hydrolyzed acid of the starting material. The filtrate was concentrated, then purified on ISCO (0-50% EtOAc in hexane) to give the title compound as a white solid. MS (ESI) m/z 250.52 (M+H).

Step 3: Methyl 5-(4-((tert-butoxycarbonyl)amino) piperidin-1-yl)-3-(4-fluorophenyl)picolinate To a solution of methyl 5-fluoro-3-(4-fluorophenyl)picolinate (2.02 g, 3.03 mmol) in DMF (40 mL) was added methyl 5-fluoro-3-(4-fluorophenyl)picolinate (0.637 g, 3.18 mmol) and potassium carbonate (0.461 g, 3.33 mmol). The reaction mixture was heated at 115° C. overnight. The mixture was cooled, diluted with ethyl acetate, washed with water (2×), brine, dried (MgSO$_4$), filtered and the solvent was evaporated under reduced pressure. The residue was purified by column chromatography on silica gel, RediSep® 120 g, eluting with EtOAc/isohexane (10-100%). The product was not pure. The impure product was dissolved in 20 ml of 50% EtOAc/Hexane, kept in the refrigerator overnight. Collected the crystals to obtained the titled compound as an off white solid. MS (ESI) m/z 430.4 (M+H).

Step 4: Methyl 4-((tert-butoxycarbonyl)amino)-5'-(4-fluorophenyl)-[1,3'-bipiperidine]-6'-carboxylate bishydrochloride Methyl 5-(4-((tert-butoxycarbonyl)amino)piperidin-1-yl)-3-(4-fluoro-phenyl)-picolinate (490 mg, 1.141 mmol), hydrogen chloride (2.282 ml, 2.282 mmol), followed by platinum(IV) oxide (51.8 mg, 0.228 mmol), were mixed in 6 mL of MeOH. The reaction mixture was degassed and stirred at room temperature using hydrogen balloon overnight. The reaction mixture was filtered through a pad of celite, rinsed with MeOH, and the filtrate was concentrated under reduced pressure. The crude product was used without purification. MS (ESI) m/z 436.47 (M+H).

Step 5: 1'-benzyl 6'-methyl 4-((tert-butoxycarbonyl)amino)-5'-(4-fluorophenyl)-[1,3'-bipiperidine]-1',6'-dicarboxylate Methyl 4-((tert-butoxycarbonyl)amino)-5'-(4-fluorophenyl)-[1,3'-bipiperidine]-6'-carboxylate hydrochloride (537 mg, 1.138 mmol) was dissolved in 10 mL of DCM, TEA (0.793 ml, 5.69 mmol) was added. The solution was cooled to 0° C., to this solution was added benzyl carbonochloridate (0.487 ml, 3.41 mmol) at 0° C., then stirred at 0° C. for 3 hours. The reaction mixture was diluted with DCM, washed with water, brine, dried (MgSO$_4$), filtered and concentrated. The residue was purified on ISCO (40 g silica gel, 0-80% EtOAc in hexane) to give title compound as a colorless gel. MS (ESI) m/z 570.56 (M+H).

Step 6: 1'-((benzyloxy)carbonyl)-4-((tert-butoxycarbonyl)amino)-5'-(4-fluorophenyl)-[1,3'-bipiperidine]-6'-carboxylic acid 1'-Benzyl 6'-methyl 4-((tert-butoxycarbonyl)amino)-5'-(4-fluorophenyl)-[1,3'-bipiperidine]-1',6'-dicarboxylate (476 mg, 0.836 mmol) was dissolved in THF/MeOH (6 mL/4 mL), to this solution was added 2M aqueous LiOH (4.18 ml, 8.36 mmol), the mixture was stirred at room temperature for 2 h. The organic solvents were removed under reduced pressure, leave some water. More water was added to dissolve the compound. The fairly clear solution was acidified with 1N HCl to pH~5, precipitate formed. The mixture was extracted with ethyl acetate. The organic fractions were washed with brine dried (Mg$_2$SO$_4$), filtered and the solvent was evaporated under reduced pressure to give title compound as a white solid. MS (ESI) m/z 556.66 (M+H).

Step 7: 1'-benzyl 6'-(2-(4-((methoxycarbonyl)amino)phenyl)-2-oxoethyl) 4-((tert-butoxycarbonyl)amino)-5'-(4-fluorophenyl)-[1,3'-bipiperidine]-1',6'-dicarboxylate Cesium carbonate (63.3 mg, 0.194 mmol) was added to a stirred mixture of 1'-((benzyloxy)carbonyl)-4-((tert-butoxycarbonyl)amino)-5'-(4-fluorophenyl)-[1,3'-bipiperidine]6'-carboxylic acid (216 mg, 0.389 mmol) and methyl (4-(2-chloroacetyl)phenyl)carbamate (88 mg, 0.389 mmol) in DMF (3.6 mL) and the mixture was stirred at room temperature for 90 min. The mixture was diluted with ethyl acetate, washed with water (2×), brine, dried (MgSO$_4$), filtered and the solvent was evaporated under reduced pressure. The residue was purified by column chromatography on silica gel RediSep® 24 g, eluting with EtOAc/isohexane (10-80%) to give title compound as a colorless film. MS (ESI) m/z 747.69 (M+H).

Step 8: benzyl 4-((tert-butoxycarbonyl)amino)-5'-(4-fluorophenyl)-6'-(5-(4-((methoxycarbonyl)amino)phenyl)-1H-imidazol-2-yl)-[1,3'-bipiperidine]-1'-carboxylate 1'-Benzyl 6'-(2-(4-((methoxycarbonyl)amino)phenyl)-2-oxoethyl) 4-((tert-butoxycarbonyl)amino)-5'-(4-fluorophenyl)-[1,3'-bipiperidine]-1',6'-dicarboxylate was brought up in triflurotoluene (2 mL) in a 5 ml microwave vial. Ammonium acetate (80 mg, 1.038 mmol) was added and then the vial was capped. Microwave irradiation was used to heat the reaction mixture at 150° C. for 20 min. The reaction mixture was concentrated under reduced pressure. The residue was purified by column chromatography on silica gel RediSep® 24 g, eluting with EtOAc/isohexane (10-100%) to give title compound as a yellow solid. MS (ESI) m/z 727.56 (M+H).

Step 9: tert-Butyl (1-(5-(4-fluorophenyl)-6-(4-(4-((methoxycarbonyl)amino)phenyl)-112-imidazol-2-yl)-112-piperidin-3-yl)piperidin-4-yl)carbamate To a solution of benzyl 4-((tert-butoxycarbonyl)amino)-5'-(4-fluorophenyl)-6'-(5-(4-((methoxycarbonyl)amino)phenyl)-1H-imidazol-2-yl)-[1,3'-bipiperidine]-1'-carboxylate (59 mg, 0.81 mmol) in EtOAc (2 mL) was added 5% Pd/C (34.6 mg, 0.016 mmol). The reaction mixture was treated under H$_2$ balloon for 6 h. The reaction mixture was filtered through a pad of celite, rinsed with EtOAc, and the filtrate was concentrated under reduced pressure. The crude product was used without purification. MS (ESI) m/z 593.52 (M+H).

Step 10: tert-Butyl (E)-(1'-(3-(5-chloro-2-(1H-tetrazol-1-yl)phenyl)acryloyl)-5'-(4-fluorophenyl)-6'-(4-(4-((methoxycarbonyl)amino)phenyl)-112-imidazol-2-yl)-[1,3'-bipiperidin]-4-yl)carbamate (E)-3-(5-chloro-2-(1H-tetrazol-1-yl)phenyl)acrylic acid (23.34 mg, 0.093 mmol) and PyBOP (48.5 mg, 0.093 mmol) in THF (2 ml) was stirred at RT for 5 min. The mixture was then added to tert-butyl (1-(5-(4-fluorophenyl)-6-(4-(4-((methoxycarbonyl)amino)phenyl)-112-imidazol-2-yl)-112-piperidin-3-yl)piperidin-4-yl)carbamate (46 mg, 0.078 mmol) in THF (2 ml) followed by DIPEA (0.041 ml, 0.233 mmol). The mixture was stirred at room temperature for 1 h. The mixture was diluted with ethyl acetate, washed with water then brine, dried over MgSO$_4$, filtered and the solvent was evaporated under reduced pressure. The residue was purified by column chromatography on silica gel RediSep® 24 g, eluting with MeOH/DCM (0-3%). The product was not pure. Second purification by preparative TLC was used to give the title compound as an off white solid. MS (ESI) m/z 825.53 (M+H).

Step 11: tert-Butyl (E)-(1'-(3-(5-chloro-2-(1H-tetrazol-1-yl)phenyl)acryloyl)-5'-(4-fluorophenyl)-6'-(4-(4-((methoxycarbonyl)amino)phenyl)-112-imidazol-2-yl)-[1,3'-bipiperidin]-4-yl)carbamate The mixture of stereoisomers from above, tert-butyl (E)-(1'-(3-(5-chloro-2-(1H-tetrazol-1-yl)phenyl)acryloyl)-5'-(4-fluorophenyl)-6'-(4-(4-((methoxycarbonyl)-amino)phenyl)-112imidazol-2-yl)-[1,3'-bipiperidin]-4-yl)carbamate, was subjected to chiral SFC using a ChiralPak® IA column (21×250 mm), 60% 2:1 IPA:MeCN/30% CO2, 55 ml/min, 100 bar, 35 C, 220 nm. Peak A 2.1 min, peak B 2.8 min. The title compound (peak 2) was isolated as a white solid. MS (ESI) m/z 825.53 (M+H).

Step 12: Methyl (4-{2-[4-amino-1'-{(2E)-3-[5-chloro-2-(1H-tetrazol-1-yl)phenyl]prop-2-enoyl}-5'-(4-fluorophenyl)-1,3'-bipiperidin-6'-yl]-1H-imidazol-4-yl}phenyl)carbamate (Example 13)

Peak 2 isolated as described above, tert-butyl (E)-(1'-(3-(5-chloro-2-(1H-tetrazol-1-yl)phenyl)acryloyl)-5'-(4-fluorophenyl)-6'-(4-(4-((methoxycarbonyl)-amino)phenyl)-112-imidazol-2-yl)-[1,3'-bipiperidin]-4-yl)carbamate was treated with 4M HCl/dioxane (0.3 mL) at room temperature for 1 h. The mixture was concentrated under reduced pressure to give title compound as a white solid. MS (ESI) m/z 725.48 (M+H).

The following compounds may be prepared by someone skilled in the art following a procedure similar to the one described above.

| Example | Structure | IUPAC Name | LCMS [M + H]+ |
|---|---|---|---|
| 14 | 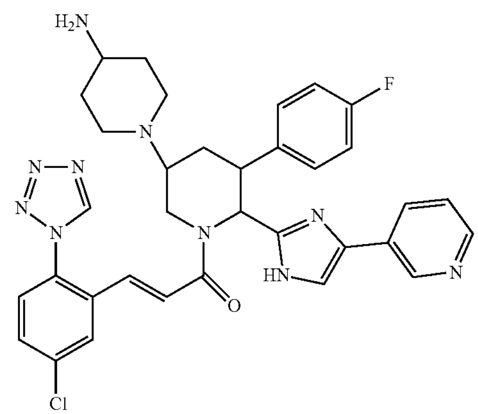 [SMILES: NC1CCN(C2CC(c3ccc(F)cc3)C(c3nc(-c4cccnc4)c[nH]3)N(C(=O)/C=C/c3cc(Cl)ccc3-n3cnnn3)C2)CC1] | 1'-{(2E)-3-[5-chloro-2-(1H-tetrazol-1-yl)phenyl]prop-2-enoyl}-5'-(4-fluorophenyl)-6'-(4-pyridin-3-yl-1H-imidazol-2-yl)-1,3'-bipiperidin-4-amine | 653.63 |
| 15 | 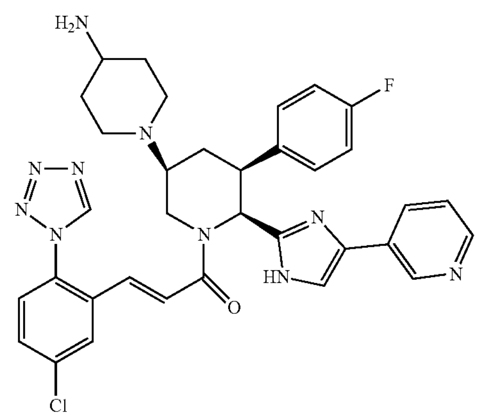 [SMILES: NC1CCN([C@H]2C[C@@H](c3ccc(F)cc3)[C@@H](c3nc(-c4cccnc4)c[nH]3)N(C(=O)/C=C/c3cc(Cl)ccc3-n3cnnn3)C2)CC1] | (3'S,5'S,6'S)-1'-{(2E)-3-[5-chloro-2-(1H-tetrazol-1-yl)phenyl]prop-2-enoyl}-5'-(4-fluorophenyl)-6'-(4-pyridin-3-yl-1H-imidazol-2-yl)-1,3'-bipiperidin-4-amine | 653.37 |
| 16 | 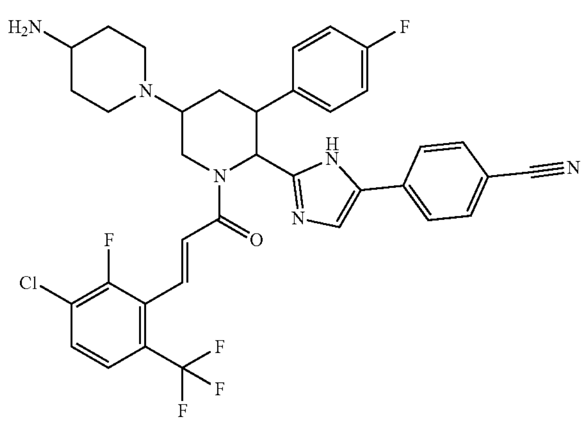 [SMILES: N#Cc1ccc(-c2cnc(C3C(c4ccc(F)cc4)CC(N4CCC(N)CC4)CN3C(=O)/C=C/c3c(C(F)(F)F)ccc(Cl)c3F)[nH]2)cc1] | 4-{2-[4-amino-1'-{(2E)-3-[3-chloro-2-fluoro-6-(trifluoromethyl)phenyl]prop-2-enoyl}-5'-(4-fluorophenyl)-1,3'-bipiperidin-6'-yl]-1H-imidazol-5-yl}benzonitrile | 695.3 |

-continued

| Example | Structure | IUPAC Name | LCMS [M + H]+ |
|---|---|---|---|
| 17 | 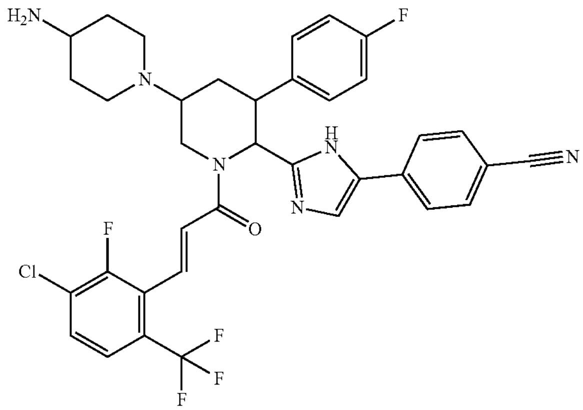 [SMILES: N#Cc1ccc(-c2cnc(C3C(c4ccc(F)cc4)CC(N4CCC(N)CC4)CN3C(=O)/C=C/c3c(C(F)(F)F)ccc(Cl)c3F)[nH]2)cc1] | 4-{2-[4-amino-1'-{(2E)-3-[3-chloro-2-fluoro-6-(trifluoromethyl)phenyl]prop-2-enoyl}-5'-(4-fluorophenyl)-1,3'-bipiperidin-6'-yl]-1H-imidazol-5-yl}benzonitrile | 695.3 |
| 18 | 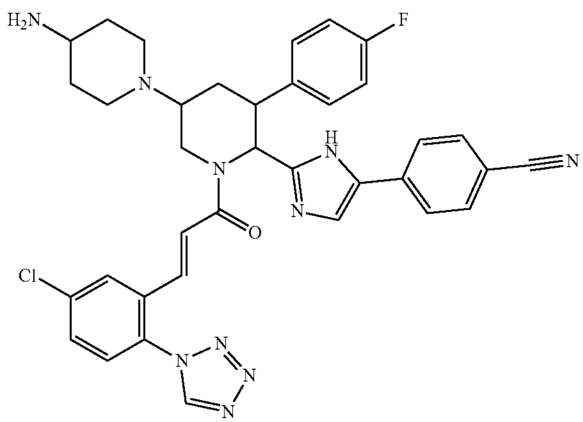 [SMILES: N#Cc1ccc(-c2cnc(C3C(c4ccc(F)cc4)CC(N4CCC(N)CC4)CN3C(=O)/C=C/c3cc(Cl)ccc3-n3cnnn3)[nH]2)cc1] | 4-{2-[4-amino-1'-{(2E)-3-[5-chloro-2-(1H-tetrazol-1-yl)phenyl]prop-2-enoyl}-5'-(4-fluorophenyl)-1,3'-bipiperidin-6'-yl]-1H-imidazol-5-yl}benzonitrile | 677.40 |
| 19 | 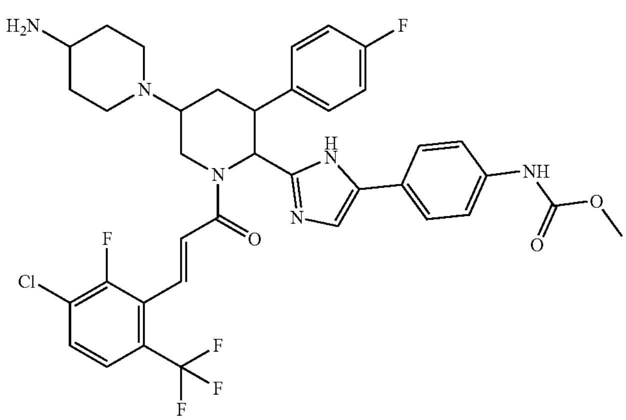 [SMILES: COC(=O)Nc1ccc(-c2cnc(C3C(c4ccc(F)cc4)CC(N4CCC(N)CC4)CN3C(=O)/C=C/c3c(C(F)(F)F)ccc(Cl)c3F)[nH]2)cc1] | methyl (4-{2-[4-amino-1'-{(2E)-3-[3-chloro-2-fluoro-6-(trifluoromethyl)phenyl]prop-2-enoyl}-5'-(4-fluorophenyl)-1,3'-bipiperidin-6'-yl]-1H-imidazol-5-yl}phenyl)carbamate | 743.38 |

| Example | Structure | IUPAC Name | LCMS [M + H]+ |
|---|---|---|---|
| 20 | 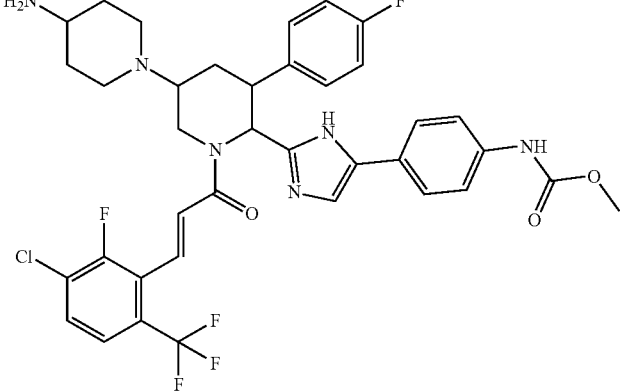 | methyl (4-{2-[4-amino-1'-{(2E)-3-[3-chloro-2-fluoro-6-(trifluoromethyl)phenyl]prop-2-enoyl}-5'-(4-fluorophenyl)-1,3'-bipiperidin-6'-yl]-1H-imidazol-5-yl}phenyl)carbamate | 743.44 |
| 21 | 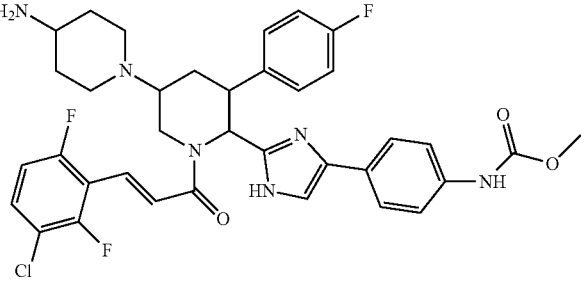 | methyl [4-(2-{4-amino-1'-[(2E)-3-(3-chloro-2,6-difluorophenyl)prop-2-enoyl]-5'-(4-fluorophenyl)-1,3'-bipiperidin-6'-yl}-1H-imidazol-4-yl)phenyl]carbamate | 693.37 |
| 22 | 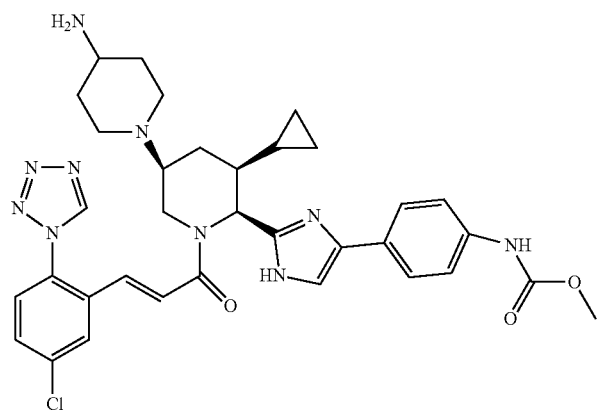 [SMILES: COC(=O)Nc1ccc(-c2c[nH]c([C@@H]3[C@H](C4CC4)C[C@H](N4CCC(N)CC4)CN3C(=O)/C=C/c3cc(Cl)ccc3-n3cnnn3)n2)cc1] | methyl (4-{2-[(3'S,5'S,6'S)-4-amino-1'-{(2E)-3-[5-chloro-2-(1H-tetrazol-1-yl)phenyl]prop-2-enoyl}-5'-cyclopropyl-1,3'-bipiperidin-6'-yl]-1H-imidazol-4-yl}phenyl)carbamate | 671.53 |

Example 23
4-((3R,5S,6S)-1-((E)-3-(5-chloro-2-(1H-tetrazol-1-yl)phenyl)acryloyl)-5-phenyl-[3,4'-bipiperidine]-6-carboxamido)benzoic acid trifluoroacetic acid salt
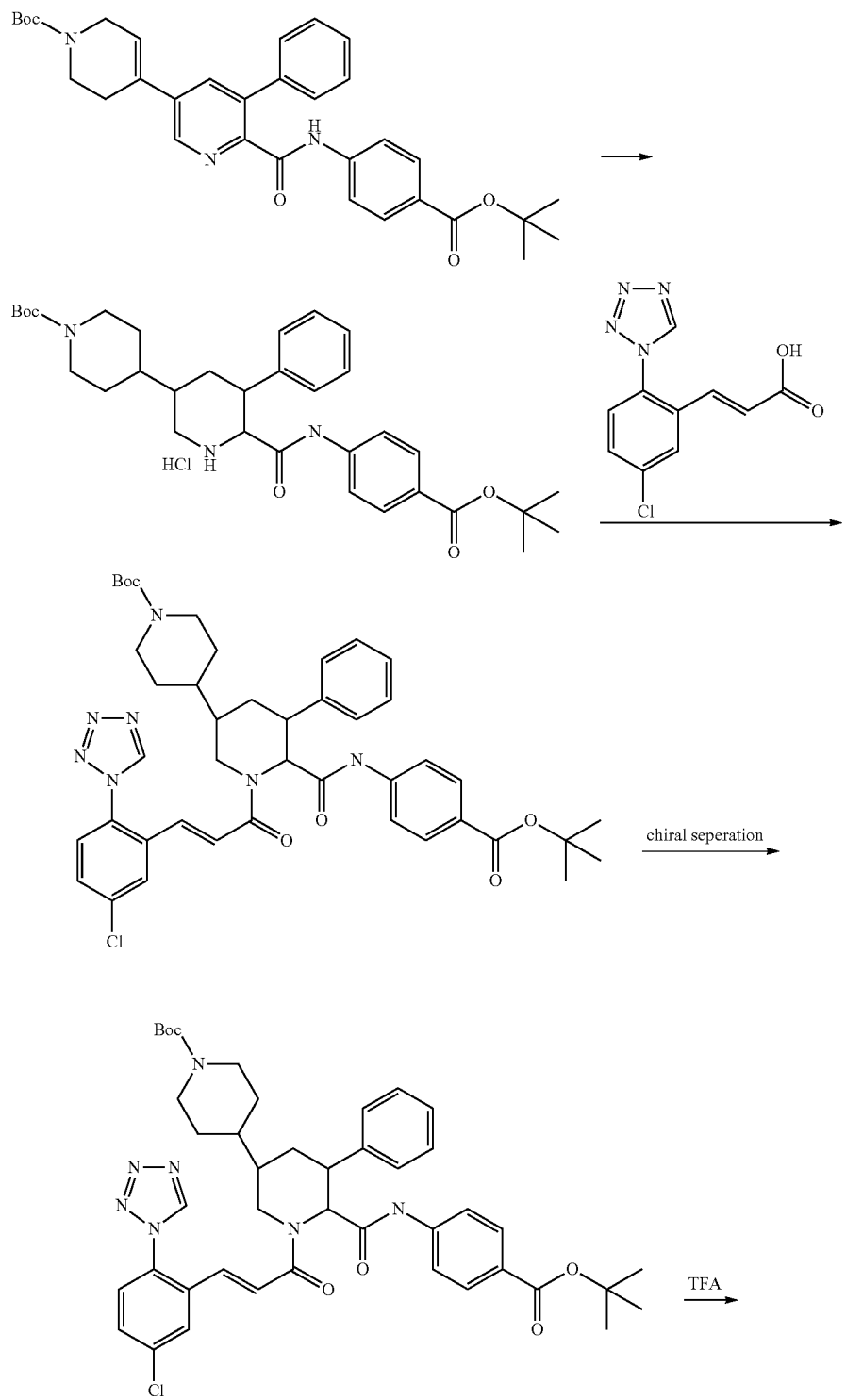

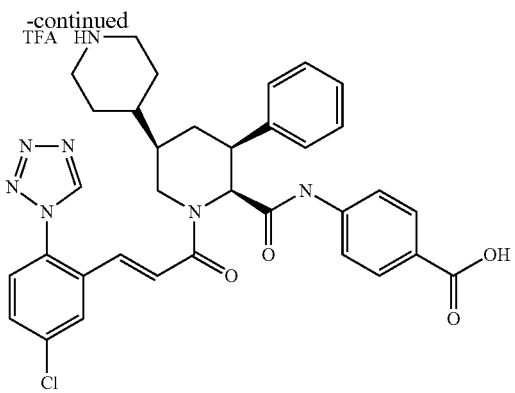

Example 23

Step 1: tert-Butyl 6-((4-(tert-butoxycarbonyl)phenyl)carbamoyl)-5-phenyl-[3,4'-bipiperidine]-1'-carboxylate hydrochloride To a solution of tert-butyl 6-((4-(tert-butoxycarbonyl)phenyl)carbamoyl)-5-phenyl-5',6'-dihydro-[3,4'-bipyridine]-1'(2'H)-carboxylate (260 mg, 0.468 mmol) in MeOH (5 mL) was added 1N aqueous solution of hydrogen chloride (0.5 mL, 0.5 mmol), followed by dioxoplatinum hydrate (22.94 mg, 0.094 mmol) at room temperature. The reaction mixture was degassed and stirred at room temperature using hydrogen balloon for 7.5 h. The reaction mixture was filtered through a pad of celite, rinsed with MeOH, and the filtrate was concentrated under reduced pressure. The crude product was used without purification. MS (ESI) m/z 564.4 (M+H).

Step 2: (E)-tert-butyl 6-((4-(tert-butoxycarbonyl)phenyl)carbamoyl)-1-(3-(5-chloro-2-(1H-tetrazol-1-yl)phenyl)acryloyl)-5-phenyl-[3,4'-bipiperidine]-1'-carboxylate DIEA (0.199 ml, 1.140 mmol) was added to a stirred mixture of tert-butyl 6-((4-(tert-butoxycarbonyl)phenyl)carbamoyl)-5-phenyl-[3,4'-bipiperidine]-1'-carboxylate hydrochloride (228 mg, 0.380 mmol), (E)-3-(5-chloro-2-(1H-tetrazol-1-yl)phenyl)acrylic acid (95 mg, 0.380 mmol) and HATU (173 mg, 0.456 mmol) in DMF (3 mL) and the mixture was stirred at room temperature for 1 h. The mixture was diluted with ethyl acetate, washed with water, brine, dried ($Mg_2SO_4$), filtered and the solvent was evaporated under reduced pressure. The residue was purified by column chromatography on silica gel RediSep® 40 g, eluting with EtOAc/isohexane (30-100%) to give the title compound as a pale yellow solid. MS (ESI) m/z 796.0 (M+H).

Step 3: (E)-tert-butyl 6-((4-(tert-butoxycarbonyl)phenyl)carbamoyl)-1-(3-(5-chloro-2-(1H-tetrazol-1-yl)phenyl)acryloyl)-5-phenyl-[3,4'-bipiperidine]-1'-carboxylate The mixture of stereoisomers from above, (E)-tert-butyl 6-((4-(tert-butoxycarbonyl)phenyl)carbamoyl)-1-(3-(5-chloro-2-(1H-tetrazol-1-yl)phenyl)-acryloyl)-5-phenyl-[3,4'-bipiperidine]-1'-carboxylate, was subjected to chiral SFC using a OD-H (2×15 cm) column eluting with 50% methanol/$CO_2$, (100 bar, flow rate 60 ml/min). Two enantiomers were isolated both as pale yellow solid. MS (ESI) m/z 796.0 (M+H).

Step 4: 4-((3R,5S,6S)-1-((E)-3-(5-chloro-2-(1H-tetrazol-1-yl)phenyl)acryloyl)-5-phenyl-[3,4'-bipiperidine]-6-carboxamido)benzoic acid trifluoroacetic acid salt (Example 23)

The above separated isomer (peak 2), (E)-tert-butyl 6-((4-(tert-butoxycarbonyl)phenyl)carbamoyl)-1-(3-(5-chloro-2-(1H-tetrazol-1-yl)phenyl)acryloyl)-5-phenyl-[3,4'-bipiperidine]-1'-carboxylate (65 mg, 0.082 mmol), was treated with TFA/DCM (0.5/1 mL) at RT for 50 min. Concentrated under reduced pressure. The residue was purified by preparative HPLC Reverse phase (C-18), eluting with Acetonitrile/Water+0.1% TFA, lyophilization to give title compound as a colorless solid. MS (ESI) m/z 640.1 (M+H). 1H NMR δ (ppm) ($CH_3OH$-d4): 1.64 (2H, m), 1.69 (2H, m), 1.96-1.94 (1H, m), 2.07 (2H, m), 2.41 (1H, d, J=12.57 Hz), 3.10-3.03 (2H, m), 3.25-3.19 (1H, m), 3.50 (2H, d, J=13.64 Hz), 3.72-3.77 (1H, m), 3.86 (1H, t, J=12.40 Hz), 4.13 (1H, d, J=12.88 Hz), 5.37 (1H, d, J=6.04 Hz), 7.14 (1H, d, J=15.53 Hz), 7.33-7.20 (7H, m), 7.38 (1H, d, J=7.41 Hz), 7.60 (1H, d, J=8.39 Hz), 7.69 (1H, dd, J=8.56, 2.29 Hz), 7.87 (2H, t, J=8.67 Hz), 8.18-8.15 (1H, m), 9.58 (1H, s).

| Example | Structure | IUPAC Name | LCMS [M + H]+ |
|---|---|---|---|
| 24 | 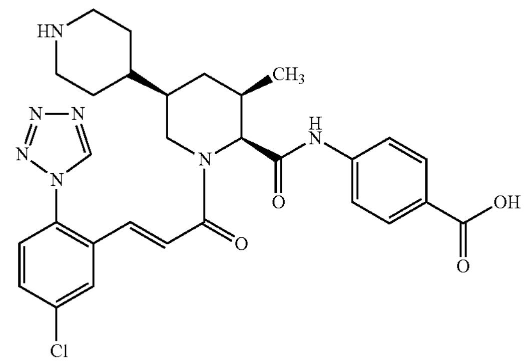 [SMILES: C[C@@H]1C[C@H](C2CCNCC2)CN(C(=O)/C=C/c2cc(Cl)ccc2-n2cnnn2)[C@@H]1C(=O)Nc1ccc(C(=O)O)cc1] | 4-((3R,5R,6S)-1-((E)-3-(5-chloro-2-(1H-tetrazol-1-yl)phenyl)acryloyl)-5-methyl-[3,4'-bipiperidine]-6-carboxamido)benzoic acid | 578.5 |
| 25 | 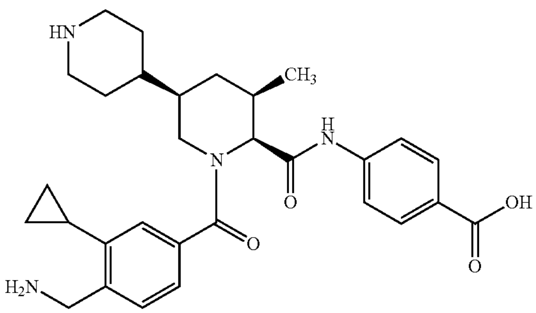 [SMILES: C[C@@H]1C[C@H](C2CCNCC2)CN(C(=O)c2ccc(CN)c(C3CC3)c2)[C@@H]1C(=O)Nc1ccc(C(=O)O)cc1] | 4-((3R,5R,6S)-1-(4-(aminomethyl)-3-cyclopropylbenzoyl)-5-methy-1-[3,4'-bipiperidine]-6-carboxamido) benzoic acid | 519.5 |
Example 26
Methyl (4-{2-[(3R,5S,6S)-1-{(2E)-3-[5-chloro-2-(1H-tetrazol-1-yl)phenyl]prop-2-enoyl}-5-cyclopropyl-3,4'-bipiperidin-6-yl]-1H-imidazol-4-yl}phenyl) carbamate
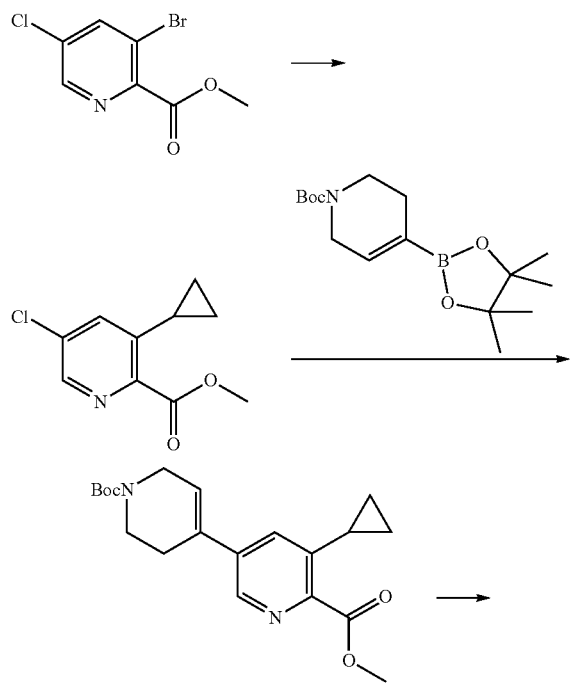

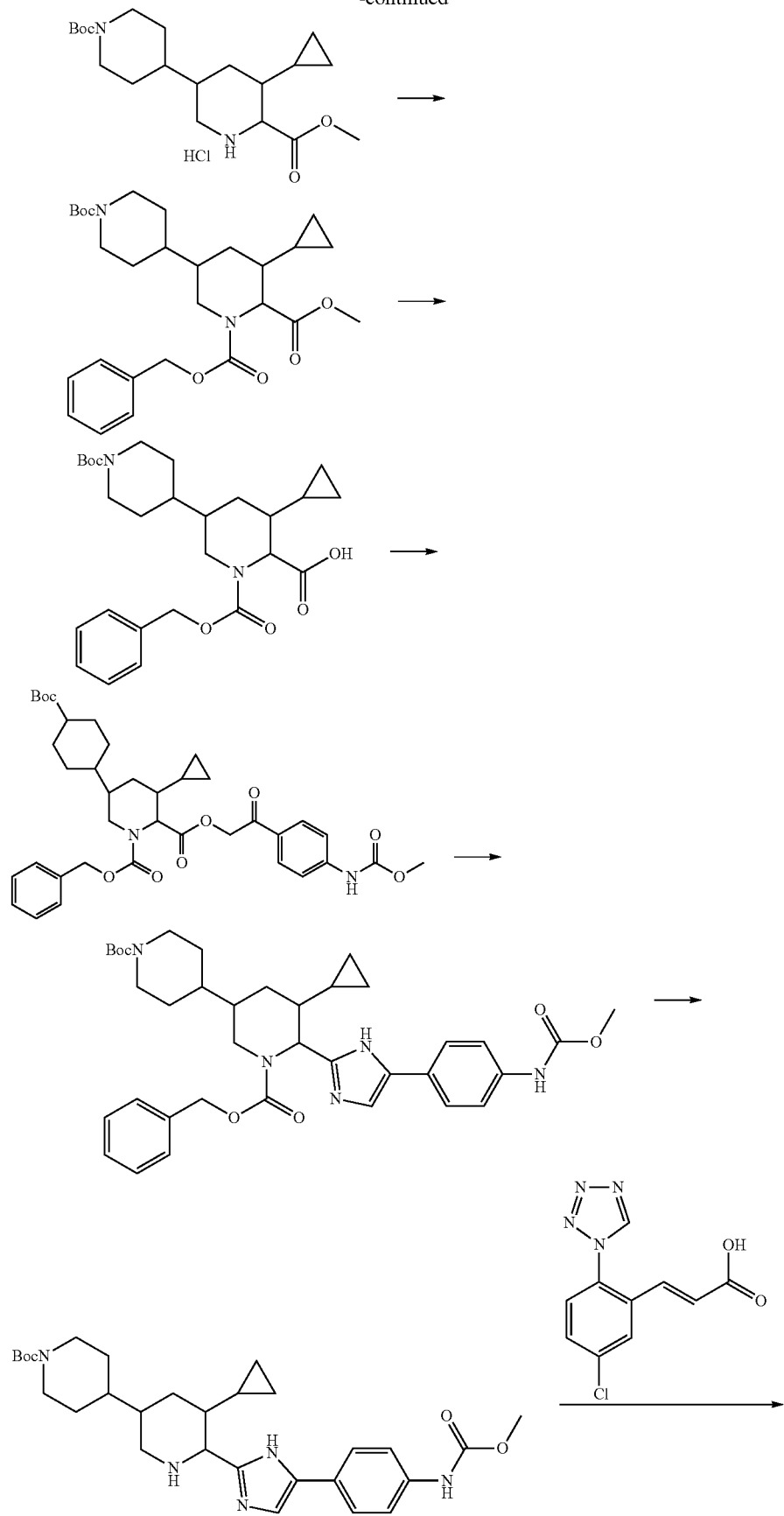

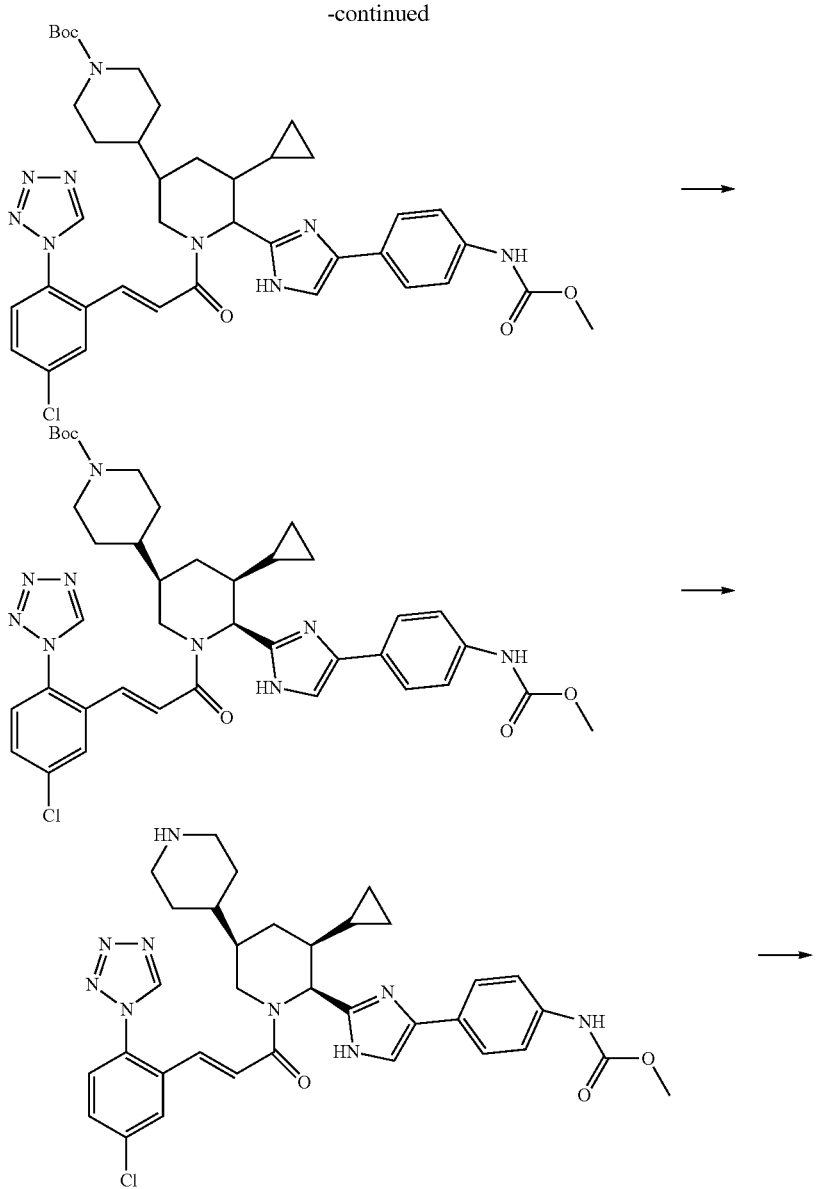

Example 26

Step 1. Methyl 5-chloro-3-cyclopropylpicolinate

A 500 mL round bottom flask was charged with methyl 3-bromo-5-chloropicolinate (6 g, 23.95 mmol), potassium cyclopropyltrifluoroborate (5 g, 33.8 mmol), Reactant 3 (2.402 g, 3.59 mmol), cesium carbonate (23.41 g, 71.9 mmol), Toluene (108 ml), and Water (11.98 ml). The reaction mixture was stirred at 100° C. for 18 hours, then cooled to room temperature. The reaction mixture was partitioned between water and ethyl acetate. The organic phase was dried over $Na_2SO_4$, filtered, and concentrated to afford the crude product. The crude product was loaded onto a 300 gram silica gel column. Flash chromatography (0-10% hexanes-ethyl acetate) was used to isolate the product as a colorless oil. MS (ESI) m/z 212.19 (M+H).

Step 2. 1'-tert-Butyl 6-methyl 5-cyclopropyl-5',6'-dihydro-[3,4'-bipyridine]-1',6(2'H)-dicarboxylate A 20 mL microwave vial was charged with methyl 5-chloro-3-cyclopropylpicolinate (0.5 g, 2.362 mmol), tert-butyl 4-(4,4,5,5-tetramethyl-1,3,2-dioxaborolan-2-yl)-5,6-dihydropyridine-1(2H)-carboxylate (913 mg, 2.95 mmol), 1,1' bis(diphenylphosphino)ferrocene-palladium(II)dichloride dichloromethane complex (386 mg, 0.472 mmol), sodium carbonate (751 mg, 7.09 mmol), dioxane (8 ml), and water (2 ml). The reaction mixture was heated in a microwave reactor at 150° C. for 30 minutes. Four identical reactions were run as above and the reaction mixtures were combined and filtered through a celite pad. The filtrate was partitioned between water and ethyl acetate. The organic phase was dried over $Na_2SO_4$, filtered, and concentrated. The crude oil was loaded onto a 120 gram silica gel column. Flash chromatography (0-100% EtOAc-hexanes) afforded the desired product at high purity. MS (ESI) m/z 359.04 (M+H).

Step 3. 1'-tert-Butyl 6-methyl 5-cyclopropyl-[3,4'-bipiperidine]-1',6-dicarboxylate hydrochloride 1'-tert-Butyl 6-methyl 5-cyclopropyl-5',6'-dihydro-[3,4'-bipyridine]-1',6(2'H)-dicarboxylate (4.5 g, 12.55 mmol) was dissolved in 20 mL of methanol. To this solution was added concentrated aqueous hydrogen chloride (1.031 ml, 12.55 mmol), degassed and added dioxoplatinum hydrate (0.308 g, 1.255 mmol) and rhodium(IV) oxide (0.373 g, 2.76 mmol). The mixture was degassed and charged with hydrogen balloon and stirred at r.t. for 6 hours. The reaction mixture was filtered through celite and washed with ethyl acetate and concentrated. Used directly for the next step. MS (ESI) m/z 367.25 (M+H).

Step 4. 1-Benzyl 1'-tert-butyl 6-methyl 5-cyclopropyl-[3,4'-bipiperidine]-1,1',6-tricarboxylate 1'-tert-Butyl 6-methyl 5-cyclopropyl-[3,4'-bipiperidine]-1',6-dicarboxylate hydrochloride (4.95 g, 12.3 mmol) was dissolved in 20 mL of DCM. Triethylamine (8.56 ml, 61.4 mmol) was added. The solution was cooled to 0° C., to this solution was added benzyl carbonochloridate (5.26 ml, 36.9 mmol) at 0° C., then stirred at 0° C. for 3 hours. The reaction mixture was then washed with water, brine, dried over sodium sulfate, filtered and concentrated, purified on flash chromatography (120 g of silica, 0-80% EOAc in hexane) to give final compound as colorless gel. MS (ESI) m/z 501.29 (M+H).

Step 5. 1-((Benzyloxy)carbonyl)-1'-(tert-butoxycarbonyl)-5-cyclopropyl-[3,4-bipiperidine]-6-carboxylic acid 1-Benzyl 1'-tert-butyl 6-methyl 5-cyclopropyl-[3,4'-bipiperidine]-1,1',6-tricarboxylate (4.05 g, 8.09 mmol) was dissolved in 10 mL of THF and 4 mL of MeOH. To this solution was added lithium hydroxide (0.969 g, 40.4 mmol) and water. The mixture was stirred at 50° C. for 4 hours until completion. The organic solvent was removed, 1M HCl was added to adjust PH to 4-5. Extracted with EtOAc, dried over sodium sulfate, filtered and dried under vacuo. Used directly for the next step. MS (ESI) m/z 487.27 (M+H).

Step 6. 1-Benzyl 1'-tert-butyl 6-(2-(4-((methoxycarbonyl)amino)phenyl)-2-oxoethyl) 5-cyclopropyl-[3,4'-bipiperidine]-1,1',6-tricarboxylate Cesium carbonate (1.231 g, 3.78 mmol) was added to a stirred mixture of 1-((benzyloxy)carbonyl)-1'-(tert-butoxycarbonyl)-5-cyclopropyl-[3,4'-bipiperidine]-6-carboxylic acid (3.83 g, 4.72 mmol) and methyl (4-(2-chloroacetyl)phenyl)carbamate (1.075 g, 4.72 mmol) were dissolved in DMF (15 mL). The mixture was stirred at room temperature for 2 h, then diluted with ethyl acetate, washed with water (2×100 mL), brine, dried (MgSO₄), filtered and the solvent was evaporated under reduced pressure. The residue was purified by column chromatography on silica gel RediSep® 120 g, eluting with EtOAc/isohexane (0-80%) to collect the product as a colorless smear. MS (ESI) m/z 678.51 (M+H).

Step 7. 1-Benzyl 1'-tert-butyl 5-cyclopropyl-6-(5-(4-((methoxycarbonyl)amino)phenyl)-1H-imidazol-2-yl)-[3,4'-bipiperidine]-1,1'-dicarboxylate 1-benzyl 1'-tert-butyl 6-(2-(4-((methoxycarbonyl)amino)phenyl)-2-oxoethyl) 5-cyclopropyl-[3,4'-bipiperidine]-1,1',6-tricarboxylate (508 mg, 0.750 mmol) was dissolved in 10 mL of toluene in 20 ml microwave vial. Acetic acid ammonia salt (289 mg, 3.75 mmol) was added and the reaction mixture was capped, prestirred for 30 sec. and then heated under microwave irradiation at 148° C. for 30 min. The mixture was concentrated. Four identical reactions were run as above and the reaction mixtures were mixed together, concentrated, extracted with EtOAc and water, purified by column chromatography on silica gel ReadySep 120 g, eluting with EtOAc/isohexane (10-80%) to give final product. MS (ESI) m/z 658.53 (M+H).

Step 8. tert-Butyl 5-cyclopropyl-6-(5-(4-((methoxycarbonyl)amino)phenyl)-1H-imidazol-2-yl)-[3,4'-bipiperidine]-1'-carboxylate 1-Benzyl 1'-tert-butyl 5-cyclopropyl-6-(5-(4-((methoxycarbonyl)amino)phenyl)-1H-imidazol-2-yl)-[3,4'-bipiperidine]-1,1'-dicarboxylate (1.05 g, 1.596 mmol) was dissolved in 20 ml of EtOAc. To this solution purged with N₂ was added palladium on carbon (0.170 g, 0.160 mmol). The mixture was stirred under hydrogen for 30 hours. Filtered through celite pad and washed with EtOAc, concentrated to give yellow solid. MS (ESI) m/z 524.44 (M+H).

Step 9. (E)-tert-Butyl 1-(3-(5-chloro-2-(1H-tetrazol-1-yl)phenyl)acryloyl)-5-cyclopropyl-6-(4-(4-((methoxycarbonyl)amino)phenyl)-1H-imidazol-2-yl)-[3,4'-bipiperidine]-1'-carboxylate N-Ethyl-N-isopropylpropan-2-amine (0.699 ml, d 0.742 g/mL, 4.01 mmol) was added to a stirred mixture of HATU (508 mg, 1.337 mmol), tert-butyl 5-cyclopropyl-6-(4-(4-((methoxycarbonyl)amino)phenyl)-1H-imidazol-2-yl)-[3,4'-bipiperidine]-1'-carboxylate (700 mg, 1.337 mmol) and (E)-3-(5-chloro-2-(1H-tetrazol-1-yl)phenyl)acrylic acid (335 mg, 1.337 mmol) in DMF (10 mL). The mixture was stirred at room temperature for 2 h. The mixture was diluted with ethyl acetate, washed with water, brine, dried (Mg₂SO₄), filtered and the solvent was evaporated under reduced pressure. The residue was purified by column chromatography on silica gel RediSep® 40 g, eluting with EtOAc/isohexane (50-100%) to give product as yellow solid. MS (ESI) m/z 756.59 (M+H).

Step 10. (3R,5S,6S)-tert-Butyl 1-((E)-3-(5-chloro-2-(1H-tetrazol-1-yl)phenyl)acryloyl)-5-cyclopropyl-6-(4-(4-((methoxycarbonyl)amino)phenyl)-1H-imidazol-2-yl)-[3,4'-bipiperidine]-1'-carboxylate (E)-tert-Butyl 1-(3-(5-chloro-2-(1H-tetrazol-1-yl)phenyl)acryloyl)-5-cyclopropyl-6-(4-(4-((methoxycarbonyl)amino)phenyl)-1H-imidazol-2-yl)-[3,4'-bipiperidine]-1'-carboxylate (144 mg, 0.187 mmol) was submitted for chiral separation, dissolved in isopropanol:DCM (3:1) at 10 mg/mL, inject 0.5 mL on OJ-H (2×25 cm) column, eluted with 35% isopropanol (0.1% DEA) at 50 mL/min under CO₂ 100 bar pressure, detected at UV 280 nm, yielded 45 mg of peak-1 (chemical purity >98%, ee>98%) and 52 mg of peak-2 (chemical purity >99%, ee>99%). The second peak was the desired compound. Retention time was at 11.13 min using the following analytical method: OJ-H (25×0.46 cm), 25% isopropanol (DEA)/CO₂, 100 bar, 3.0 mL/min, 220, 254 nm. MS (ESI) m/z 771.67 (M+H).

Step 11. Methyl (4-{2-[(3R,5S,6S)-1-{(2E)-3-[5-chloro-2-(1H-tetrazol-1-yl)phenyl]prop-2-enoyl}-5-cyclopropyl-3,4'-bipiperidin-6-yl]-1H-imidazol-4-yl}phenyl)carbamate (Example 26)

(3R,5S,6S)-tert-Butyl 1-((E)-3-(5-chloro-2-(1H-tetrazol-1-yl)phenyl)acryloyl)-5-cyclopropyl-6-(4-(4-((methoxycarbonyl)amino)phenyl)-1H-imidazol-2-yl)-[3,4'-bipiperidine]-1'-carboxylate (45 mg, 0.059 mmol) was dissolved in 1 mL of DCM, to this solution was added TFA (1 mL). the mixture was stirred at room temperature for 1 hour. Solvent was removed under pressure. The residue was purified on HPLC (10-90% acetonitrile in water with 0.05% TFA) to yield the title compound. MS (ESI) m/z 656.00 (M+H).

The following compound may be prepared by someone skilled in the art following a procedure similar to the one described above.

| Example | Structure | IUPAC Name | Exact Mass [M + H]+ |
|---|---|---|---|
| 27 | 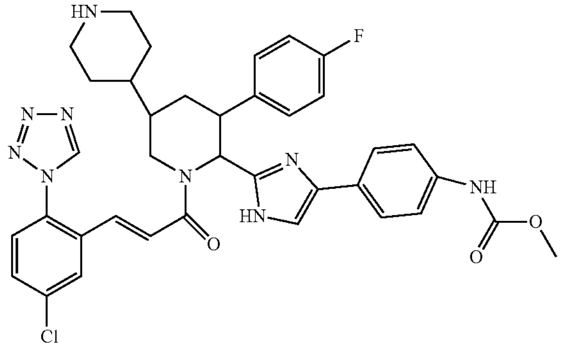 [SMILES: COC(=O)Nc1ccc(-c2c[nH]c(C3C(c4ccc(F)cc4)CC(C4CCNCC4)CN3C(=O)/C=C/c3cc(Cl)ccc3-n3cnnn3)n2)cc1] | methyl (4-{2-[1-{(2E)-3-[5-chloro-2-(1H-tetrazol-1-yl)phenyl]prop-2-enoyl}-5-(4-fluorophenyl)-3,4'-bipiperidin-6-yl]-1H-imidazol-4-yl}phenyl)carbamate | 710.07 |

Example 28

Methyl (4-{2-[(3R,5S,6S)-1-{(2E)-3-[5-chloro-2-(1H-tetrazol-1-yl)phenyl]prop-2-enoyl}-5-cyclopropyl-1'-(methylsulfonyl)-3,4'-bipiperidin-6-yl]-1H-imidazol-4yl}phenyl)carbamate

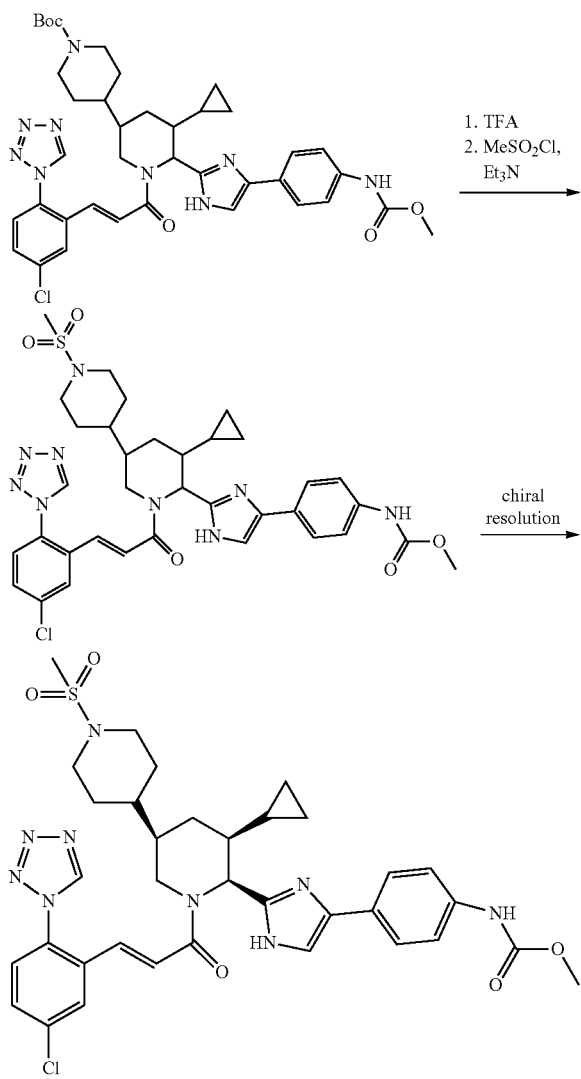

Step 1. (E)-methyl(4-(2-(1-(3-(5-chloro-2-(1H-tetrazol-1-yl)phenyl)acryloyl)-5-cyclopropyl-1'-(methylsulfonyl)-[3,4'-bipiperidin]-6-yl)-1H-imidazol-4-yl)phenyl)carbamate Step 1: (E)-tert-butyl 1-(3-(5-chloro-2-(1H-tetrazol-1-yl)phenyl)acryloyl)-5-cyclopropyl-6-(4-(4-((methoxycarbonyl)amino)phenyl)-1H-imidazol-2-yl)-[3,4'-bipiperidine]-1'-carboxylate (270 mg, 0.357 mmol) was dissolved in 4 mL of DCM and 2 mL of TFA. The mixture was stirred at room temperature for one hour. The solvent was removed and the compound was dried under vacuo.

Step 2: The material from step 1 in DCM (5 ml) at RT was combined with triethylamine (0.299 mL, 2.142 mmol). The mixture became a clear solution which was cooled to 0° C. Methanesulfonyl chloride (0.028 ml, 0.357 mmol) was added dropwise. The mixture was stirred at 0° C. for 1 h. The mixture was quenched with aq. sat'd NaHCO₃ then partitioned between water and DCM. The organic phase washed with brine, dried (MgSO₄), filtered and the solvent was evaporated under reduced pressure. The crude product was purified on ISCO (24 g, 0-10% MeOH in DCM) to give the final product. MS (ESI) m/z 734.41 (M+H).

Step 2. Methyl (4-{2-[(3R,5S,6S)-1-{(2E)-3-[5-chloro-2-(1H-tetrazol-1-yl)phenyl]prop-2-enoyl}-5-cyclopropyl-1'-(methylsulfonyl)-3,4'-bipiperidin-6-yl]-1H-imidazol-4yl}phenyl)carbamate (Example 28)

The compound from above (145 mg, 0.187 mmol) was submitted for chiral separation, dissolved in isopropanol:DCM (3:1) at 9 mg/mL, inject 0.5 mL on OJ-H (2×25 cm) column, eluted with 35% isopropanol (0.1% DEA) at 65 mL/min under CO₂ 100 bar pressure, detected at UV 280 nm, yielded 57 mg of peak-1 (chemical purity >99%, ee>98%) and 52 mg of peak-2 (chemical purity >99%, ee>99%). The second peak was the desired compound (Example 28). Retention time was at 7.09 min using the following analytical method: OJ-H (25×0.46 cm), 40% isopropanol (DEA)/CO₂, 100 bar, 3.0 mL/min, 220, 254 nm. MS (ESI) m/z 734.41 (M+H).

Example 29

(2S,3S,5S)-1'-{(2E)-3-[5-Chloro-2-(1H-tetrazol-1-yl)phenyl]prop-2-enoyl}-3-(4-fluorophenyl)-N-1H-indazol-5-yl-5-morpholin-4-ylpiperidine-2-carboxamide

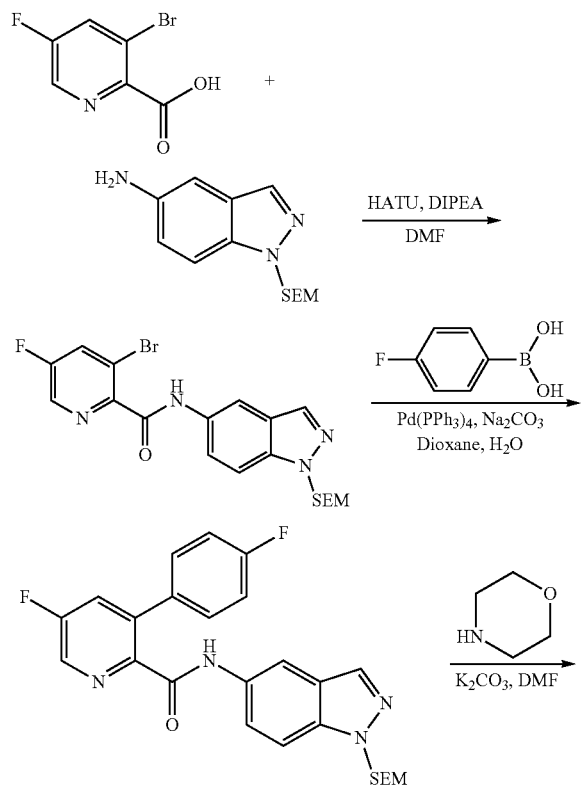

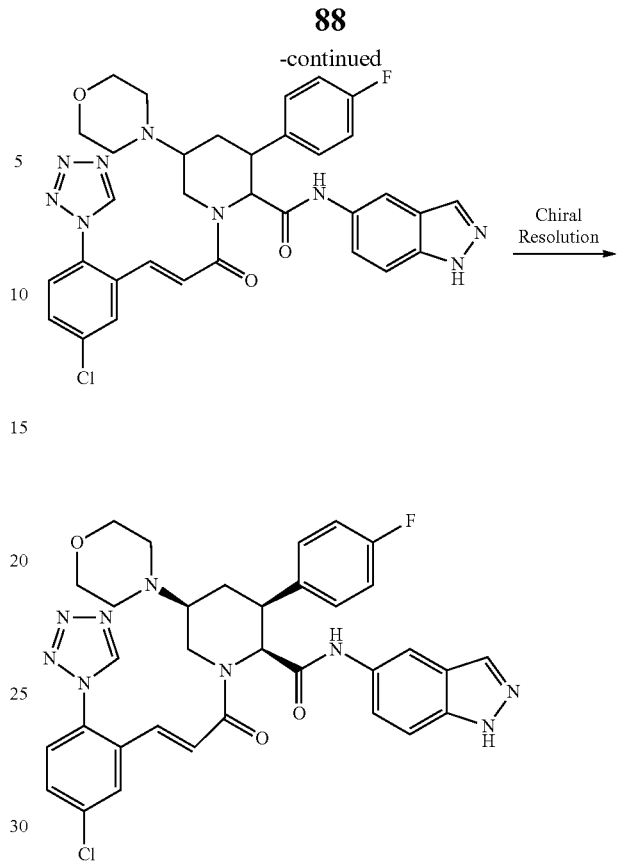

Step 1: 3-Bromo-5-fluoro-N-(1-((2-(trimethylsilyl)ethoxy)methyl)-1H-indazol-5-yl)picolinamide

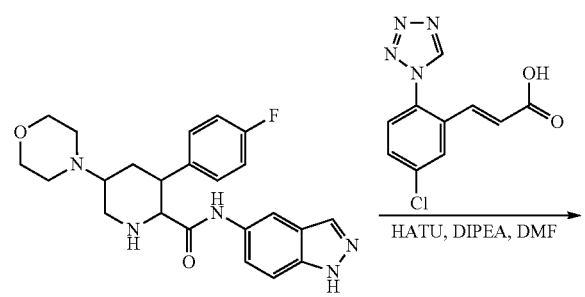

To a mixture of 3-bromo-5-fluoropicolinic acid (334 mg, 1.52 mmol) and 1-((2-(trimethylsilyl)-ethoxy)methyl)-1H-indazol-5-amine (400 mg, 1.52 mmol) in DMF (5 mL) was added DIPEA (0.80 mL, 4.6 mmol) and HATU (1.155 g, 3.04 mmol) and the mixture was stirred at room temperature for 30 h. The reaction mixture was quenched with water (50 mL) and extracted with EtOAc (2×100 mL). The combined organic layers were washed with brine (50 mL), dried over anhydrous Na₂SO₄, filtered and concentrated under reduced pressure. The residue was purified by flash chromatography (0-30% EtOAc in hexanes) to provide the title compound.

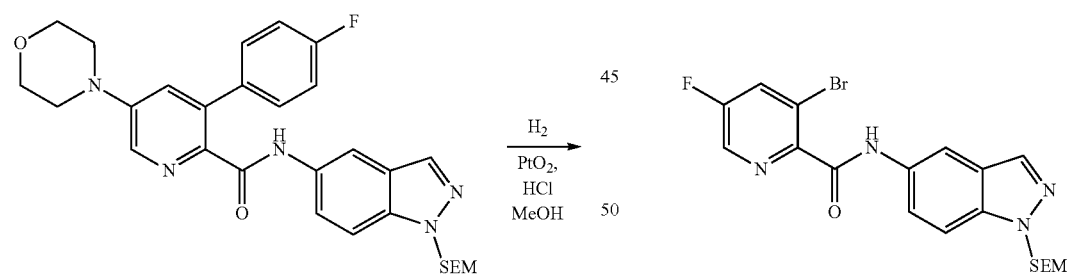

Step 2: 5-Fluoro-3-(4-fluorophenyl)-N-(1-((2-(trimethylsilyl)ethoxy)methyl)-1H-indazol-5-yl)picolinamide

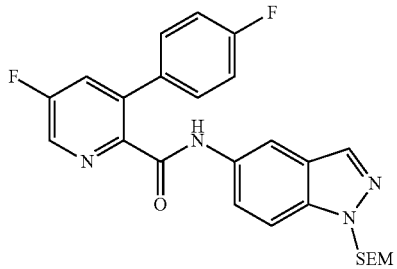 [SMILES: C[Si](C)(C)CCOCn1ncc2cc(NC(=O)c3ncc(F)cc3-c3ccc(F)cc3)ccc21]

To a stirred solution of 3-bromo-5-fluoro-N-(1-((2-(trimethylsilyl)ethoxy)-methyl)-1H-indazol-5-yl)picolinamide (600 mg, 1.289 mmol) in 1,4-dioxane/H$_2$O (4:1) (9 mL) were added 4-fluorophenylboronic acid (361 mg, 2.58 mmol), Na$_2$CO$_3$ (410 mg, 3.87 mmol) and Pd(PPh$_3$)$_4$ (298 mg, 0.258 mmol) at ambient temperature and the resulting mixture was purged with nitrogen gas bubbling for 5 minutes. The mixture was heated at 120° C. for 1 hour using microwave irradiation. The reaction mixture was cooled to room temperature and partitioned between ethyl acetate, water and saturated aqueous NaHCO$_3$. The organic phase was separated. The combined organic layers were washed with brine (100 mL), dried over anhydrous Na$_2$SO$_4$, filtered and concentrated under reduced pressure. The residue was purified by combiflash flash chromatography (0-35% EtOAc in hexanes) to provide the title compound.

Step 3: 3-(4-fluorophenyl)-5-morpholino-N-(1-((2-(trimethylsilyl)ethoxy)-methyl)-1H-indazol-5-yl)picolinamide

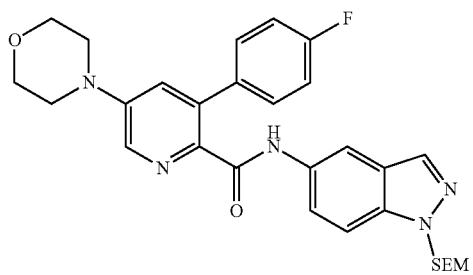 [SMILES: C[Si](C)(C)CCOCn1ncc2cc(NC(=O)c3ncc(N4CCOCC4)cc3-c3ccc(F)cc3)ccc21]

5-Fluoro-3-(4-fluorophenyl)-N-(1-((2-(trimethylsilyl)ethoxy)methyl)-1H-indazol-5-yl)picolinamide (250 mg, 0.520 mmol), morpholine (0.048 mL, 0.55 mmol), and potassium carbonate (410 mg, 3.87 mmol) were combined with 6 mL DMF. The reaction mixture was heated at 115° C. overnight. By LCMS, all the starting material was consumed. The reaction mixture was cooled to room temperature and partitioned between ethyl acetate and water. The organic phase was separated; the combined organic layers were washed with brine (100 mL), dried over anhydrous Na$_2$SO$_4$, filtered and concentrated under reduced pressure. The residue was purified by combiflash flash chromatography (0-55% EtOAc in hexanes) to provide the title compound and residual impurities. Additional purification was accomplished by prep HPLC.

Step 4: 3-(4-Fluorophenyl)-N-(1H-indazol-5-yl)-5-morpholinopiperidine-2-carboxamide

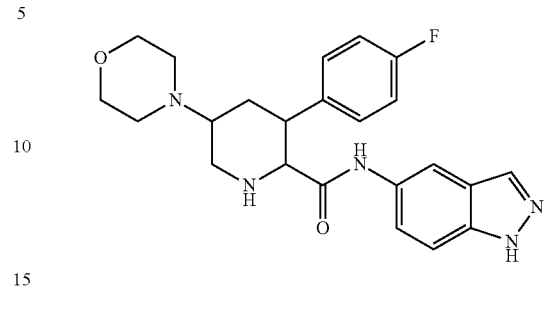

A 2 M aqueous solution of hydrogen chloride (40.0 equiv) was added to 3-(4-fluorophenyl)-N-(1H-indazol-5-yl)-5-morpholinopiperidine-2-carboxamide (70.0 mg, 0.520 mmol), MeOH (5 mL), and platinum (IV) oxide monohydrate (2.0 equiv). The resulting mixture was degassed with hydrogen gas bubbling for 1 minute. The reaction was stirred under a balloon pressure of hydrogen and reaction progress was monitored by LCMS. After 30 h, the reaction was stopped and the crude product was purified by reverse phase column chromatography to afford the title compound. MS (ESI) m/z 424 (M+H).

Step 5: (E)-1-(3-(5-chloro-2-(1H-tetrazol-1-yl)phenyl)acryloyl)-3-(4-fluorophenyl)-N-(1H-indazol-5-yl)-5-morpholinopiperidine-2-carboxamide

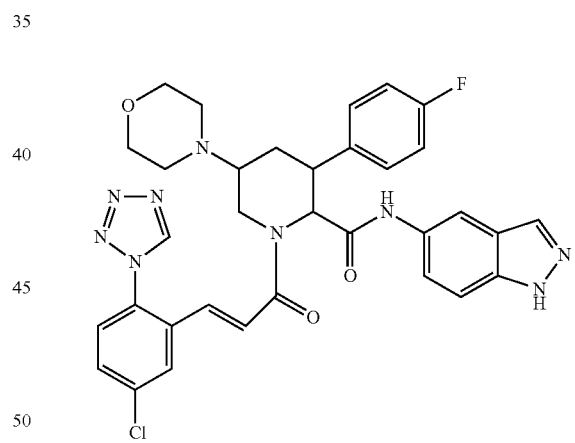

To a mixture of (E)-3-(5-chloro-2-(1H-tetrazol-1-yl)phenyl)acrylic acid (2.5 mg, 9.9 μmol) and 3-(4-fluorophenyl)-N-(1H-indazol-5-yl)-5-morpholinopiperidine-2-carboxamide (4.0 mg, 9.5 μmol) was added DIPEA (16 μL, 94 μmol) and HATU (7.2 mg, 19 μmol) and the mixture was stirred at room temperature for 15 h. The reaction mixture was quenched with water (5 mL) and extracted with EtOAc (2×25 mL). The combined organic layers were washed with brine (50 mL), dried over anhydrous Na$_2$SO$_4$, filtered and concentrated and purified by Prep HPLC using acetonitrile and water to afford the title compound. MS (ESI) m/z 656.50 (M+H).

Step 6: (2S,3S,5S)-1-{(2E)-3-[5-Chloro-2-(1H-tetrazol-1-yl)phenyl]prop-2-enoyl}3-(4-fluorophenyl)-N-1H-indazol-5-yl-5-morpholin-4-ylpiperidine-2-carboxamide (Example 29)

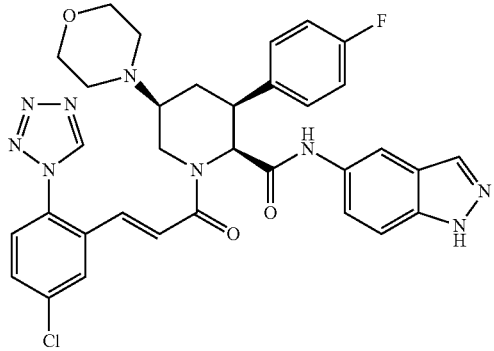 [SMILES: O=C(Nc1ccc2[nH]ncc2c1)[C@@H]1[C@H](c2ccc(F)cc2)C[C@H](N2CCOCC2)CN1C(=O)/C=C/c1cc(Cl)ccc1-n1cnnn1]

The title compound was obtained using chiral SFC (21× 250 mm OD column eluting with 60% MeOH/CO$_2$ and 0.2% NH$_4$OH at 100 bar and 35° C.) starting from the racemic sample of (E)-1-(3-(5-chloro-2-(1H-tetrazol-1-yl)phenyl)-acryloyl)-3-(4-fluorophenyl)-N-(1H-indazol-5-yl)-5-morpholinopiperidine-2-carboxamide. MS (ESI) m/z 656.51 (M+H).

The following compounds may be prepared by someone skilled in the art following a procedure similar to the one described above.

| Example | Structure | IUPAC Name | LCMS [M + H]+ |
|---|---|---|---|
| 30 | 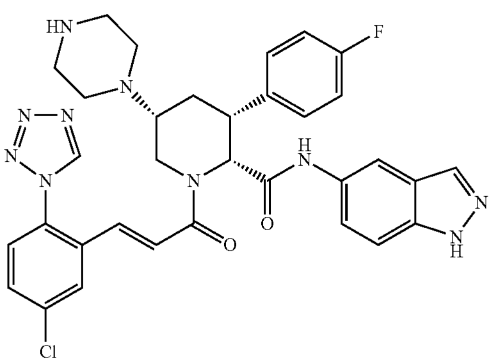 [SMILES: O=C(Nc1ccc2[nH]ncc2c1)[C@H]1[C@@H](c2ccc(F)cc2)C[C@@H](N2CCNCC2)CN1C(=O)/C=C/c1cc(Cl)ccc1-n1cnnn1] | (2R,3R,5R)-1-{(2E)-3-[5-chloro-2-(1H-tetrazol-1-yl)phenyl]prop-2-enoyl}-3-(4-fluorophenyl)-N-1H-indazol-5-yl-5-piperazin-1-ylpiperidine-2-carboxamide | 655.65 |
| 31 | 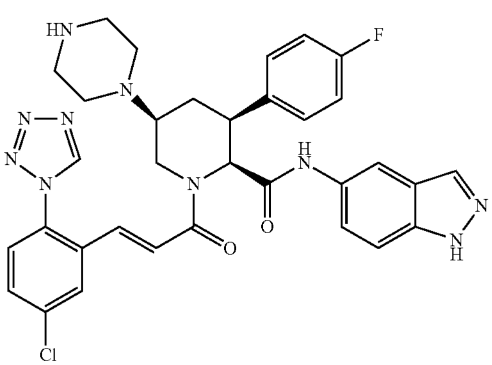 | (2S,3S,5S)-1-{(2E)-3-[5-chloro-2-(1H-tetrazol-1-yl)phenyl]prop-2-enoyl}-3-(4-fluorophenyl)-N-1H-indazol-5-yl-5-piperazin-1-ylpiperidine-2-carboxamide | 655.51 |

-continued

| Example | Structure | IUPAC Name | LCMS [M + H]+ |
|---|---|---|---|
| 32 | 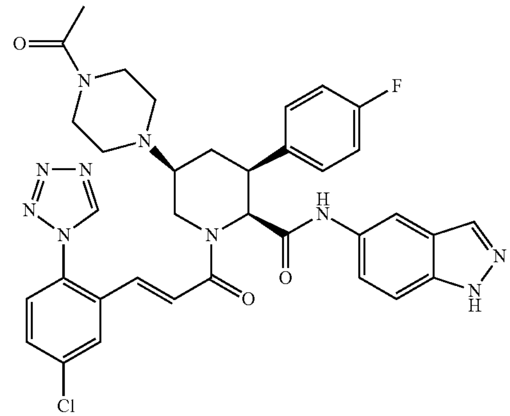 [SMILES: CC(=O)N1CCN([C@H]2C[C@@H](c3ccc(F)cc3)[C@@H](C(=O)Nc3ccc4[nH]ncc4c3)N(C(=O)/C=C/c3cc(Cl)ccc3-n3cnnn3)C2)CC1] | (2S,3S,5S)-5-(4-acetylpiperazin-1-yl)-1-{(2E)-3-[5-chloro-2-(1H-tetrazol-1-yl)phenyl]prop-2-enoyl}-3-(4-fluorophenyl)-N-1H-indazol-5-ylpiperidine-2-carboxamide | 697.62 |

Preparation of Intermediates

Preparation of (E)-3-(5-chloro-2-(1H-tetrazol-1-yl)phenyl)acrylic acid

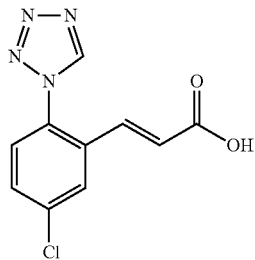 [SMILES: O=C(O)/C=C/c1cc(Cl)ccc1-n1cnnn1]

Step 1: 5-Chloro-2-(1H-tetrazol-1-yl)benzoic acid

A suspension of 2-amino-5-chlorobenzoic acid (5.0 g, 29.1 mmol) and sodium azide (5.41 g, 83 mmol) in trimethyl orthoformate (9.12 ml, 83 mmol) was cooled to 0° C. Acetic acid (100 mL) was added, and the mixture was stirred at 0° C. for 3 hours. The reaction was warmed to room temperature and then stirred at room temperature overnight. The mixture was concentrated in vacuo, and the residue was partitioned between ethyl acetate and 3 N HCl. The organic phase was dried over MgSO$_4$, filtered and the solvent was evaporated under reduced pressure to give 5-chloro-2-(1H-tetrazol-1-yl)benzoic acid.

Step 2: 5-Chloro-N-methoxy-N-methyl-2-(1H-tetrazol-1-yl)benzamide

A mixture of 5-chloro-2-(1H-tetrazol-1-yl)benzoic acid (6.28 g, 28.0 mmol), PyBOP (14.55 g, 28.0 mmol), N,O-dimethylhydroxylamine hydrochloride (2.73 g, 28.0 mmol), N,N-diisopropylethylamine (14.65 mL, 84 mmol), and DCM (200 mL) was stirred at room temperature over the weekend. After this time, the reaction mixture was concentrated in vacuo. The residue was diluted with ethyl acetate, washed with water, 10% aqueous KHSO$_4$, saturated aqueous NaHCO$_3$, and brine. The organic phase was dried over MgSO$_4$, filtered and the solvent was evaporated under reduced pressure. The residue was purified by column chromatography on silica gel (Biotage® 65i), eluting with ethyl acetate to give 5-chloro-N-methoxy-N-methyl-2-(1H-tetrazol-1-yl)benzamide as an off white solid.

Step 3: 5-Chloro-2-(1H-tetrazol-1-yl)benzaldehyde

A solution of 5-chloro-N-methoxy-N-methyl-2-(1H-tetrazol-1-yl)benzamide (2.25 g, 8.41 mmol) in 30 mL of THF was added dropwise to a stirred, −78° C. 1 M solution of LiAlH$_4$ (16.81 mL, 16.81 mmol) in THF. Dropwise addition occurred over a period of 30 minutes, and the mixture was stirred at −78° C. for 1 hour. After this time, 6.5 mL of cool water was added carefully. The resulting mixture was diluted with ethyl acetate, and washed with 1 M hydrochloric acid followed by brine. The organic phase was dried over MgSO$_4$, filtered and the solvent was evaporated under reduced pressure to give 5-chloro-2-(1H-tetrazol-1-yl)benzaldehyde as a light green solid.

Step 4: (E)-methyl 3-(5-chloro-2-(1H-tetrazol-1-yl)phenyl)acrylate

Methyl 2-(dimethoxyphosphoryl)acetate (1.402 ml, 9.72 mmol) was added dropwise to a stirred, 0° C. suspension of sodium hydride (0.359 g, 8.97 mmol) in THF (60 mL). The reaction mixture was allowed to warm up to room temperature and the stirred for 1 hour. A solution of 5-chloro-2-(1H-tetrazol-1-yl)benzaldehyde (1.56 g, 7.48 mmol) in THF (10 mL) was then added. The mixture was stirred vigorously for 30 minutes. The mixture was poured into a cold saturated NH$_4$Cl solution. The resulting mixture was extracted with ethyl acetate and the combined organic fractions were washed with brine, dried over MgSO$_4$, filtered and the solvent was evaporated under reduced pressure. The residue was recrystallized from ethyl acetate. The solid was collected and dried in vacuo to give (E)-methyl 3-(5-chloro-2-(1H-tetrazol-1-yl)phenyl)acrylate as an off white solid.

Step 5: (E)-3-(5-chloro-2-(1H-tetrazol-1-yl)phenyl)acrylic acid

A suspension of (E)-methyl 3-(5-chloro-2-(1H-tetrazol-1-yl)phenyl)acrylate (1.27 g, 4.80 mmol), 1 M aqueous sodium hydroxide (14.4 mL, 14.4 mmol) was stirred at room temperature vigorously for 2.5 hours. The mixture was neutralized with 1 N hydrochloric acid and then concentrated to give a beige solid. The solid was partitioned between 1 N hydrochloric acid and ethyl acetate. The organic layer was washed with brine, dried and concentrated to give (E)-3-(5-chloro-2-(1H-tetrazol-1-yl)phenyl)acrylic acid as an off white solid. MS (ESI) m/z 251.03 (M+H), 292.11 (M+CH$_3$CN).

Preparation of methyl (4-(2-chloroacetyl)phenyl)carbamate

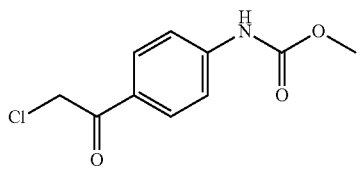

Step 1: Methyl phenylcarbamate

To a reaction mixture of aniline (500 g, 5.37 mol) in dioxane (2 L) and H$_2$O (2 L) was added NaOH (236 g, 5.91 mol). After stirring for 1 hour, methyl chloroformate (550 g, 5.91 mol) was added and the reaction mixture was stirred for 16 hours. The reaction mixture was concentrated and diluted with EA and H$_2$O. The organic layer was dried over Na$_2$SO$_4$ and concentrated to provide the title compounds as an oil. $^1$H NMR (400 MHz, CDCl$_3$) δ (ppm): 3.79 (s, 3H), 6.66 (m, 1H), 7.06-7.09 (m, 1H), 7.30-7.34 (m, 2H), 7.38-7.40 (m, 2H).

Step 2: Methyl (4-(2-chloroacetyl)phenyl)carbamate

A reaction mixture of methyl phenylcarbamate (500 g, 3.3 mol), 2-chloroacetyl chloride (556 g, 5 mol) and AlCl$_3$ (1.3 kg, 10 mol) in 1,2-dichloroethane (5 L) was heated at 70° C. for 2 hours. The reaction mixture was allowed to cool down and poured onto ice-H$_2$O. The aqueous layer was extracted with DCM three times. The combined organic layers were washed with H$_2$O, dried over Na$_2$SO$_4$ and concentrated. The residue was purified by column chromatography to provide the title compound as an off-white solid. $^1$H NMR (400 MHz, DMSO-d$_6$) δ (ppm): 3.71 (s, 3H), 5.09 (s, 2H), 7.62 (d, J=8.8 Hz, 2H), 7.94 (d, J=8.8 Hz, 2H), 10.12 (s, 1H).

Preparation of tert-butyl 6-((4-(tert-butoxycarbonyl)phenyl)carbamoyl)-5-phenyl-5',6'-dihydro-[3,4'-bipyridine]-1'(2'H)-carboxylate

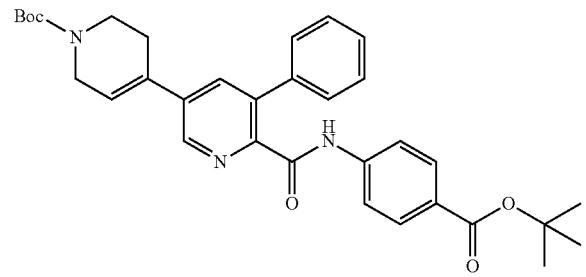 [SMILES: CC(C)(C)OC(=O)c1ccc(NC(=O)c2ncc(C3=CCN(C(=O)OC(C)(C)C)CC3)cc2-c2ccccc2)cc1]

Step 1: tert-butyl 4-(3-bromo-5-chloropicolinamido)benzoate

A 500 mL round bottom flask was charged with 3-bromo-5-chloropicolinic acid (5 g, 21.2 mmol), tert-butyl 4-aminobenzoate (4.29 g, 22.2 mmol), HATU (8.04 g, 21.2 mmol), THF (100 ml), and finally DIPEA (11.08 ml, 63.4 mmol). The resulting mixture was stirred at room temperature over the weekend. After this time, the reaction mixture was a yellowish suspension. LCMS shows complete conversion to the desired product. The reaction mixture was partitioned between ethyl acetate and saturated aqueous NaHCO$_3$. The organic phase was dried over Na$_2$SO$_4$ and then filtered and concentrated to give the title compound as 12.08 grams of a yellow solid. MS (ESI) m/z 412.94 (M+H).

Step 2: tert-butyl 4-(5-chloro-3-phenylpicolinamido)benzoate

A 20 mL microwave vial was charged with tert-butyl 4-(3-bromo-5-chloropicolinamido)-benzoate (500 mg, 1.215 mmol), phenylboronic acid (160 mg, 1.31 mmol), Pd(PPh$_3$)$_4$ (105 mg, 0.091 mmol), sodium carbonate (322 mg, 3.04 mmol), dioxane (7.2 ml) and water (800 µl). The reaction mixture was heated in the microwave at 120° C. for 45 minutes. A second reaction was set up using twice the amounts described above. The crude product was purified using silica gel flash chromatography to afford the title compound. MS (ESI) m/z 409.07 (M+H).

Step 3: tert-butyl 6-((4-(tert-butoxycarbonyl)phenyl) carbamoyl)-5-phenyl-5',6'-dihydro-[3,4'-bipyridine]-1'(2'H)-carboxylate A 20 mL microwave vial was charged with tert-butyl 4-(5-chloro-3-phenylpicolinamido)benzoate (0.2 g, 0.489 mmol), tert-butyl 4-(4,4,5,5-tetramethyl-1,3,2-dioxaborolan-2-yl)-5,6-dihydropyridine-1(2H)-carboxylate (0.19 g, 0.614 mmol), 1,1'-bis(diphenyl-phosphino)ferrocene-palladium(II) dichloride dichloromethane complex (0.100 g, 0.122 mmol), sodium carbonate (0.16 g, 1.510 mmol), dioxane (3.91 ml), and water (0.978 ml). The reaction mixture was heated in a microwave reactor at 150° C. for 45 minutes. The reaction mixture was partitioned between ethyl acetate and water. The organic phase was dried over Na$_2$SO$_4$, filtered, and concentrated to afford a purple oil which was loaded onto a 80 gram silica gel column. Flash chromatography (0%-40% EtOAc in hexanes) was used to isolated the title compound. MS (ESI) m/z 556.33 (M+H).

Factor XIa Assay

The effectiveness of compounds of the present invention as inhibitors of Coagulation Factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, K$_i$.

Factor XIa determinations were made in 50 mM HEPES buffer at pH 7.4 containing 150 mM NaCl, 5 mM $CaCl_2$, and 0.1% PEG 8000 (polyethylene glycol; JT Baker or Fisher Scientific). Determinations were made using purified human Factor XIa at a final concentration of 40 pM (Sekisui Diagnostics) and the synthetic substrate, Z-Gly-Pro-Arg-AFC, TFA salt (Sigma #C0980) at a concentration of 100 µM.

Activity assays were performed by diluting a stock solution of substrate at least tenfold to a final concentration $\leq 0.1$ $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m/[S]$, $[I]/e$, and $[I]/e$ (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in the following equation.

$$V_o/V_i = 1 + [I]/K_i$$

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

Factor XIa Inhibition ($IC_{50}$ (nM))

| | |
|---|---|
| 1 | 0.8 |
| 2 | 11.4 |
| 3 | 27.2 |
| 4 | 2.2 |
| 5 | 104.8 |
| 6 | 141.8 |
| 7 | 0.4 |
| 8 | 4.7 |
| 9 | 2.5 |
| 10 | 306.5 |
| 11 | 6.1 |
| 12 | 154.8 |
| 13 | 1.7 |
| 14 | 139 |
| 15 | 82.1 |
| 16 | 35.6 |
| 17 | 889 |
| 18 | 16.5 |
| 19 | 67.8 |
| 20 | 128.3 |
| 21 | 407.1 |
| 22 | 671.2 |
| 23 | 640.1 |
| 24 | 578.5 |
| 25 | 519.4 |
| 26 | 656.2 |
| 27 | 710.2 |
| 28 | 651.9 |
| 29 | 81.1 |
| 30 | 767.5 |
| 31 | 40.9 |
| 32 | 72.2 |

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

Compounds of the Formula (I) can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIa inhibitors can also be co-administered with suitable anticoagulants, including, but not limited to, other Factor XIa inhibitors, thrombin inhibitors, thrombin receptor antagonists, Factor VIIa inhibitors, Factor Xa inhibitors, Factor IXa inhibitors, Factor XIIa inhibitors, adenosine diphosphate antiplatelet agents (e.g., P2Y12 antagonists), fibrinogen receptor antagonists (e.g., to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)-N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, freebase, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XIa inhibitors of the invention in combination with other suitable anti-platelet agents, anticoagulation agents, or thrombolytic agents may be the same as those doses of Factor XIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds in preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

What is claimed is:
1. A compound of Formula I

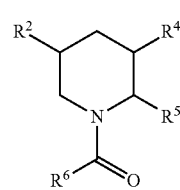

I or a pharmaceutically acceptable salt thereof, wherein $R^2$ is
1) phenyl,
2) $R^{21}$, 3) 4-7-membered saturated carbocycle,
4) —OR$^{21}$, or 5) 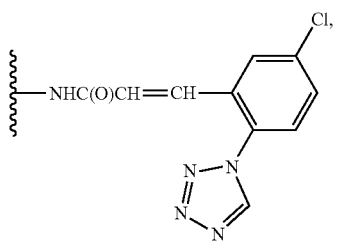

wherein R$^{21}$ is 4-7-membered unsaturated or saturated heterocycle containing one or two heteroatoms independently selected from the N, O and S, wherein phenyl is unsubstituted or monosubstituted with CF$_3$, and heterocycle is unsubstituted or monosubstituted with NH$_2$, SO$_2$CH$_3$ or COCH$_3$;

R$^6$ is
1) —CH=CH—R$^{63}$,
2) —CH$_2$CH$_2$—R$^{63}$,
3) 4-7-membered monocyclic saturated heterocycle having one or two heteroatoms independently selected from N, O and S,
4) R$^{62}$,
5) 7-9-membered bicyclic unsaturated carbocycle, wherein R$^{63}$ is phenyl which is mono, di or trisubstituted with a substituent independently selected from halogen, CF$_3$ and tetrazole, saturated heterocycle is unsubstituted or substituted at the nitrogen atom with —C(NH)NH$_2$, and R$^{62}$ is unsaturated or saturated carbocycle unsubstituted or independently substituted with one or two of —CH$_2$NH$_2$, NH$_2$, C(CH$_3$)$_2$NH$_2$, C$_{1-6}$ alkyl, or C$_{3-8}$ cycloalkyl, or 6) 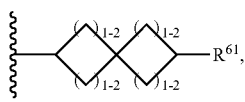

wherein R$^{61}$ is —(CH$_2$)$_{0-1}$NH$_2$;

R$^4$ is
1) —CH$_2$OR$^{41}$, wherein R$^{41}$ is hydrogen or —Si(C$_{1-6}$ alkyl)(C$_{1-6}$ alkyl)(C$_{1-6}$ alkyl),
2) phenyl,
3) 3-7-membered monocyclic saturated carbocycle,
4) C$_{1-6}$ alkyl, or
5) —O—R$^{42}$, wherein R$^{42}$ is a 4-7-membered monocyclic saturated heterocycle having one or two heteroatoms independently selected from N, O and S, wherein phenyl is unsubstituted or substituted with one or two substituents independently selected from CF$_3$, halogen, NH$_2$, OCF$_3$, C(O)NH$_2$, C$_{1-6}$ alkyl or

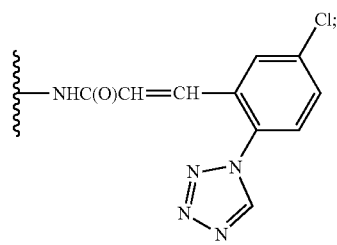

R$^5$ is
1) —C(O)NHR$^{51}$ wherein
R$^{51}$ is
a) 3-7-membered monocyclic saturated or unsaturated carbocycle,
b) 8-membered bicyclic saturated carbocycle, or
c) 9-membered bicyclic unsaturated heterocycle
wherein carbocycle is unsubstituted or substituted with one or two substituents independently selected from C(O)OC(C$_{1-6}$ alkyl)(C$_{1-6}$ alkyl)(C$_{1-6}$ alkyl) or C(O)OH, and wherein heterocycle containing one or two heteroatoms selected from N, O and S, is unsubstituted or substituted with methyl, 2) 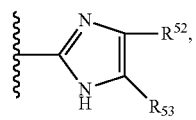

wherein
R$^{52}$ is
a) 3-7-membered monocyclic saturated or unsaturated carbocycle,
b) 6-membered unsaturated heterocycle containing 1 nitrogen atom, or
c) 9-membered bicyclic unsaturated heterocycle containing 1 or 2 heteroatoms, selected from N and O
wherein carbocycle is unsubstituted or substituted with one or two substituents independently selected from CN, halogen, OC$_{1-6}$ alkyl, SO$_2$C$_{1-6}$ alkyl, CF$_3$, C(O)OC$_{1-6}$ alkyl, NH$_2$, NHC(O)OC$_{1-6}$ alkyl, NHC(O)C$_{1-6}$ alkyl, C(O)OC(CH$_3$)$_2$, C(O)OH, PO$_3$H$_2$, or PO$_3$(C$_{1-6}$ alkyl)$_2$, wherein heterocycle is unsubstituted or substituted with methyl, and wherein bicyclic heterocycle is unsubstituted or substituted with a =O, and R$^{53}$ is hydrogen, halogen or C$_{1-6}$ alkyl, and 3) 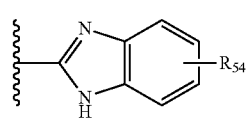

wherein
R$^{54}$ is hydrogen or halogen.

2. A compound of claim 1, or a pharmaceutically acceptable salt thereof, wherein $R^2$ is
1) phenyl
2) $R^{21}$,
3) 5-6-membered saturated carbocycle,
4) —$OR^{21}$, or
5) 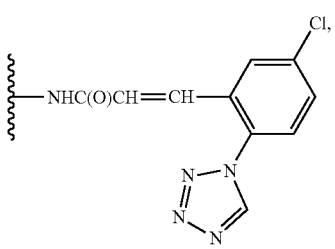

wherein $R^{21}$ is 5-6-membered saturated heterocycle containing one or two N heteroatoms,
wherein phenyl is unsubstituted or monosubstituted with $CF_3$, and saturated heterocycle is unsubstituted or monosubstituted with $NH_2$, $SO_2CH_3$ or $COCH_3$;

$R^6$ is
1) —CH=CH—$R^{63}$, or
2) $R^{62}$,
wherein $R^{63}$ is phenyl which is mono, di or trisubstituted with a substituent independently selected from halogen, $CF_3$ and tetrazole, and $R^{62}$ is unsaturated carbocycle unsubstituted or substituted with one or two substituents independently selected from —$CH_2NH_2$, $NH_2$, $C(CH_3)_2NH_2$, $C_{1-6}$ alkyl, or $C_{3-8}$ cycloalkyl;

$R^4$ is
1) phenyl,
2) cyclohexyl,
3) $C_{1-6}$ alkyl, or
4) —$OR^{42}$, wherein $R^{42}$ is a 6-membered monocyclic saturated heterocycle having one or two N atoms,
wherein phenyl is unsubstituted or substituted with one or two substituents independently selected from $CF_3$, halogen, $NH_2$, $OCF_3$, $C(O)NH_2$, $C_{1-6}$ alkyl or

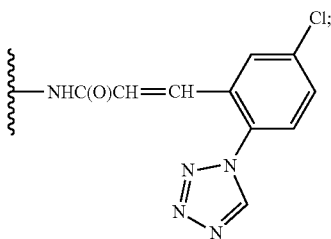

$R^5$ is
—$C(O)NHR^{51}$ wherein
$R^{51}$ is
a) 3-7 membered monocyclic saturated or unsaturated carbocycle,
b) 8 membered bicyclic saturated carbocycle, or
c) 9 membered bicyclic unsaturated heterocycle,
wherein carbocycle is unsubstituted or unsubstituted with with one or two substituents independently selected from $C(O)OC(C_{1-6}$ alkyl)($C_{1-6}$ alkyl) or $C(O)OH$, wherein heterocycle contains one or two heteroatoms selected from N, O and S, and wherein heterocycle is unsubstituted or substituted with methyl.

3. A compound of claim 1, or a pharmaceutically acceptable salt thereof, wherein $R^4$ is
1) phenyl,
2) cyclohexyl,
3) methyl or ethyl, or
4) —O—$R^{42}$, herein $R^{42}$ is piperidinyl,
wherein phenyl is unsubstituted or substituted with one or two substituents independently selected from $CF_3$, halogen, $NH_2$, $OCF_3$, $C(O)NH_2$, $C_{1-6}$ alkyl or

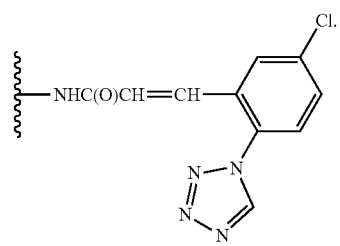

4. A compound of claim 1, or a pharmaceutically acceptable salt thereof, wherein
$R^6$ is
1) —CH=CH—$R^{63}$, or
2) $R^{62}$,
wherein $R^{63}$ is phenyl substituted with chloro and tetrazole, and $R^{62}$ is phenyl unsubstituted or substituted with one or two substituents independently selected from —$CH_2NH_2$, or cyclopropyl.

5. A compound of claim 1, or a pharmaceutically acceptable salt thereof, wherein
$R^6$ is

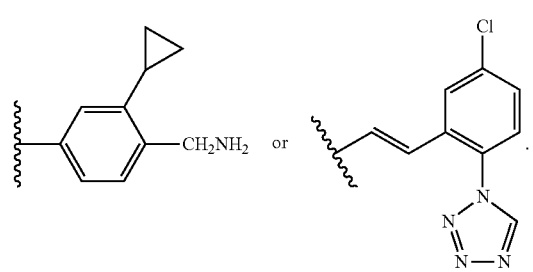

6. A compound of claim 1, or a pharmaceutically acceptable salt thereof, wherein $R^4$ is
1) phenyl, or
2) cyclohexyl,
3) methyl or ethyl, or
4) —O—$R^{42}$.

7. A compound of claim 1, or a pharmaceutically acceptable salt thereof, wherein R⁴ is

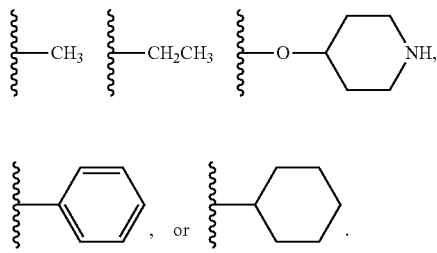

, or

8. A compound of claim 1, or a pharmaceutically acceptable salt thereof, wherein
R⁵ is
—C(O)NHR⁵¹, wherein R⁵¹ is
a) phenyl, or
b) 9 membered bicyclic unsaturated, unsubstituted heterocycle containing one or two N atoms,
wherein phenyl is unsubstituted or unsubstituted with one or two of C(O)OH.

9. A compound of claim 1, or a pharmaceutically acceptable salt thereof, wherein
R⁵ is

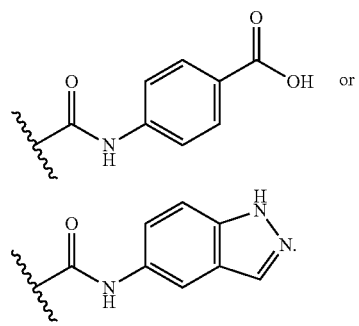

10. A compound of claim 1, or a pharmaceutically acceptable salt thereof, wherein
R² is
1) phenyl
2) R²¹,
3) cyclohexyl,
4) —OR²¹, or
5)

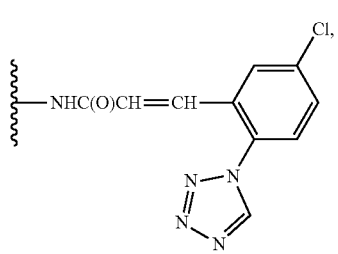

wherein R²¹ is 6-membered saturated heterocycle containing one or two N heteroatoms,
wherein phenyl is unsubstituted or monosubstituted with CF₃, and saturated heterocycle is unsubstituted or monosubstituted with NH₂, SO₂CH₃ or COCH₃.

11. A compound of claim 1, or a pharmaceutically acceptable salt thereof, wherein
R² is

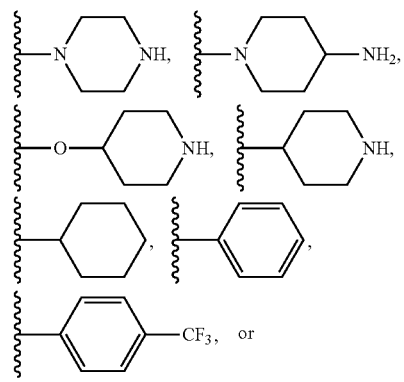

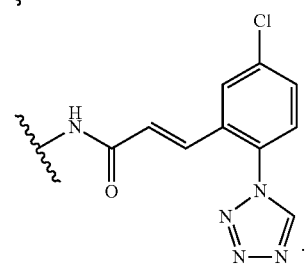

12. A compound of claim 1, or a pharmaceutically acceptable salt thereof, which is
(E)-4-(4-amino-1'-(3-(5-chloro-2-(1H-tetrazol-1-yl)phenyl)acryloyl)-5'-phenyl-[1,3'-bipiperidine]-6'-carboxamido)benzoic acid,
(E)-4-(1-(3-(5-chloro-2-(1H-tetrazol-1-yl)phenyl)acryloyl)-3-phenyl-5-(piperazin-1-yl)piperidine-2-carboxamido)benzoic acid,
4-({[4-amino-1'-{(2E)-3-[5-chloro-2-(1H-tetrazol-1-yl)phenyl]prop-2-enoyl}-5'-(1-methylethyl)-1,3'-bipiperidin-6'-yl]carbonyl}amino)benzoic acid,
4-{[(4-amino-1'-{(2E)-3-[5-chloro-2-(1H-tetrazol-1-yl)phenyl]prop-2-enoyl}-5'-cyclopropyl-1,3'-bipiperidin-6'-yl)carbonyl]amino}benzoic acid,
4-{[(4-amino-1'-{(2E)-3-[5-chloro-2-(1H-tetrazol-1-yl)phenyl]prop-2-enoyl}-5'-methyl-1,3'-bipiperidin-6'-yl)carbonyl]amino}benzoic acid,
4-({[(3'S,5'S,6'S)-4-amino-1'-{(2E)-3-[5-chloro-2-(1H-tetrazol-1-yl)phenyl]prop-2-enoyl}-5'-phenyl-1,3'-bipiperidin-6'-yl]carbonyl}amino)benzoic acid,
4-({[(3'R,5'R,6'R)-4-amino-1'-{(2E)-3-[5-chloro-2-(1H-tetrazol-1-yl)phenyl]prop-2-enoyl}-5'-phenyl-1,3'-bipiperidin-6'-yl]carbonyl}amino)benzoic acid,
4-(4-((E)-3-(5-chloro-2-(1H-tetrazol-1-yl)phenyl)acrylamido)-1'-((E)-3-(5-chloro-2-(1H-tetrazol-1-yl)phenyl)acryloyl)-5'-phenyl-[1,3'-bipiperidine]-6'-carboxamido)benzoic acid,
4-((2S,3S,5S)-1-((E)-3-(5-chloro-2-(1H-tetrazol-1-yl)phenyl)acryloyl)-3-phenyl-5-(piperidin-4-yloxy)piperidine-2-carboxamido)benzoic acid,
4-((2R,3R,5R)-1-((E)-3-(5-chloro-2-(1H-tetrazol-1-yl)phenyl)acryloyl)-3-phenyl-5-(piperidin-4-yloxy)piperidine-2-carboxamido)benzoic acid,
(E)-4-(1-(3-(5-chloro-2-(1H-tetrazol-1-yl)phenyl)acryloyl)-3-phenyl-5-(piperidin-4-yloxy)piperidine-2-carboxamido)benzoic acid, 4-(1-((E)-3-(5-chloro-2-(1H-tetrazol-1-yl)phenyl)acryloyl)-5-phenyl-3-(piperidin-4-yloxy)piperidine-2-carboxamido)benzoic acid, methyl (4-{2-[4-amino-1'-{(2E)-3-[5-chloro-2-(1H-tetrazol-1-yl)phenyl]prop-2-enoyl}-5'-(4-fluorophenyl)-1,3'-bipiperidin-6'-yl]-1H-imidazol-4-yl}phenyl)carbamate, 1'-{(2E)-3-[5-chloro-2-(1H-tetrazol-1-yl)phenyl]prop-2-enoyl}-5'-(4-fluorophenyl)-6'-(4-pyridin-3-yl-1H-imidazol-2-yl)-1,3'-bipiperidin-4-amine, (3'S,5'S,6'S)-1'-{(2E)-3-[5-chloro-2-(1H-tetrazol-1-yl)phenyl]prop-2-enoyl}-5'-(4-fluorophenyl)-6'-(4-pyridin-3-yl-1H-imidazol-2-yl)-1,3'-bipiperidin-4-amine, 4-{2-[4-amino-1'-{(2E)-3-[3-chloro-2-fluoro-6-(trifluoromethyl)phenyl]prop-2-enoyl}-5'-(4-fluorophenyl)-1,3'-bipiperidin-6'-yl]-1H-imidazol-5-yl}benzonitrile, 4-{2-[4-amino-1'-{(2E)-3-[3-chloro-2-fluoro-6-(trifluoromethyl)phenyl]prop-2-enoyl}-5'-(4-fluorophenyl)-1,3'-bipiperidin-6'-yl]-1H-imidazol-5-yl}benzonitrile, 4-{2-[4-amino-1'-{(2E)-3-[5-chloro-2-(1H-tetrazol-1-yl)phenyl]prop-2-enoyl}-5'-(4-fluorophenyl)-1,3'-bipiperidin-6'-yl]-1H-imidazol-5-yl}benzonitrile, methyl (4-{2-[4-amino-1'-{(2E)-3-[3-chloro-2-fluoro-6-(trifluoromethyl)phenyl]prop-2-enoyl}-5'-(4-fluorophenyl)-1,3'-bipiperidin-6'-yl]-1H-imidazol-5-yl}phenyl)carbamate, methyl (4-{2-[4-amino-1'-{(2E)-3-[3-chloro-2-fluoro-6-(trifluoromethyl)phenyl]prop-2-enoyl}-5'-(4-fluorophenyl)-1,3'-bipiperidin-6'-yl]-1H-imidazol-5-yl}phenyl)carbamate, methyl [4-(2-{4-amino-1'-[(2E)-3-(3-chloro-2,6-difluorophenyl)prop-2-enoyl]-5'-(4-fluorophenyl)-1,3'-bipiperidin-6'-yl}-1H-imidazol-4-yl)phenyl]carbamate, methyl (4-{2-[(3'S,5'S,6'S)-4-amino-1'-{(2E)-3-[5-chloro-2-(1H-tetrazol-1-yl)phenyl]prop-2-enoyl}-5'-cyclopropyl-1,3'-bipiperidin-6'-yl]-1H-imidazol-4-yl}phenyl)carbamate, 4-((3R,5S,6S)-1-((E)-3-(5-chloro-2-(1H-tetrazol-1-yl)phenyl)acryloyl)-5-phenyl-[3,4'-bipiperidine]-6-carboxamido)benzoic acid trifluoroacetic acid salt, 4-((3R,5R,6S)-1-((E)-3-(5-chloro-2-(1H-tetrazol-1-yl)phenyl)acryloyl)-5-methyl-[3,4'-bipiperidine]-6-carboxamido)benzoic acid, 4-((3R,5R,6S)-1-(4-(aminomethyl)-3-cyclopropylbenzoyl)-5-methy-1-[3,4'-bipiperidine]-6-carboxamido)benzoic acid, methyl (4-{2-[(3R,5S,6S)-1-{(2E)-3-[5-chloro-2-(1H-tetrazol-1-yl)phenyl]prop-2-enoyl}-5-cyclopropyl-3,4'-bipiperidin-6-yl]-1H-imidazol-4-yl}phenyl)carbamate, methyl (4-{2-[1-{(2E)-3-[5-chloro-2-(1H-tetrazol-1-yl)phenyl]prop-2-enoyl}-5-(4-fluorophenyl)-3,4'-bipiperidin-6-yl]-1H-imidazol-4-yl}phenyl)carbamate, methyl (4-{2-[(3R,5S,6S)-1-{(2E)-3-[5-chloro-2-(1H-tetrazol-1-yl)phenyl]prop-2-enoyl}-5-cyclopropyl-1'-(methylsulfonyl)-3,4'-bipiperidin-6-yl]-1H-imidazol-4-yl}phenyl)carbamate, (2S,3S,5S)-1-{(2E)-3-[5-chloro-2-(1H-tetrazol-1-yl)phenyl]prop-2-enoyl}-3-(4-fluorophenyl)-N-1H-indazol-5-yl-5-morpholin-4-ylpiperidine-2-carboxamide, (2R,3R,5R)-1-{(2E)-3-[5-chloro-2-(1H-tetrazol-1-yl)phenyl]prop-2-enoyl}-3-(4-fluorophenyl)-N-1H-indazol-5-yl-5-piperazin-1-ylpiperidine-2-carboxamide, (2S,3S,5S)-1-{(2E)-3-[5-chloro-2-(1H-tetrazol-1-yl)phenyl]prop-2-enoyl}-3-(4-fluorophenyl)-N-1H-indazol-5-yl-5-piperazin-1-ylpiperidine-2-carboxamide, (2S,3S,5S)-5-(4-acetylpiperazin-1-yl)-1-{(2E)-3-[5-chloro-2-(1H-tetrazol-1-yl)phenyl]prop-2-enoyl}-3-(4-fluorophenyl)-N-1H-indazol-5-ylpiperidine-2-carboxamide.

13. A composition for inhibiting thrombus formation in blood comprising a compound of claim 1, or a pharmaceutically acceptable salt thereof, and a pharmaceutically acceptable carrier.

14. A method for inhibiting thrombin in blood comprising adding to the blood a composition of claim 13.

15. A method for inhibiting formation of blood platelet aggregates in blood comprising adding to the blood a composition of claim 13.

16. A method for inhibiting thrombus formation in blood comprising adding to the blood a composition of claim 13.

17. A method for treating or preventing venous thromboembolism and pulmonary embolism in a mammal comprising administering to the mammal a composition of claim 13.

18. A method for treating or preventing deep vein thrombosis in a mammal comprising administering to the mammal a composition of claim 13.

19. A method for treating or preventing thromboembolic stroke in humans and other mammals comprising administering to the mammal a composition of claim 13.

* * * * *